(12) United States Patent
Mootha et al.

(10) Patent No.: US 9,399,032 B2
(45) Date of Patent: Jul. 26, 2016

(54) METHODS AND COMPOSITIONS FOR TREATING DEGENERATIVE AND ISCHEMIC DISORDERS

(75) Inventors: Vamsi K. Mootha, Boston, MA (US); Vishal Gohil, College Station, TX (US); Sunil Sheth, San Mateo, CA (US); Yuhua Ji, Redwood City, CA (US)

(73) Assignee: The General Hospital Corporation, Boston, MA (US)

( * ) Notice: Subject to any disclaimer, the term of this patent is extended or adjusted under 35 U.S.C. 154(b) by 581 days.

(21) Appl. No.: 13/320,348

(22) PCT Filed: May 14, 2010

(86) PCT No.: PCT/US2010/034985
§ 371 (c)(1),
(2), (4) Date: Jan. 17, 2012

(87) PCT Pub. No.: WO2010/132821
PCT Pub. Date: Nov. 18, 2010

(65) Prior Publication Data
US 2012/0136007 A1  May 31, 2012

Related U.S. Application Data

(60) Provisional application No. 61/178,191, filed on May 14, 2009, provisional application No. 61/234,788, filed on Aug. 18, 2009.

(51) Int. Cl.
| | | |
|---|---|---|
| A61K 31/495 | (2006.01) | |
| A61P 9/10 | (2006.01) | |
| A61K 31/382 | (2006.01) | |
| A61K 31/496 | (2006.01) | |
| A61K 31/5415 | (2006.01) | |
| A61K 31/55 | (2006.01) | |

(52) U.S. Cl.
CPC ............. *A61K 31/382* (2013.01); *A61K 31/496* (2013.01); *A61K 31/5415* (2013.01); *A61K 31/55* (2013.01)

(58) Field of Classification Search
CPC .................................................. A61K 31/495
USPC ...................................... 514/255.04; 544/396
See application file for complete search history.

(56) References Cited

U.S. PATENT DOCUMENTS

| | | |
|---|---|---|
| 7,160,865 B2 | 1/2007 | Lampidis et al. |
| 7,338,940 B2 | 3/2008 | Lampidis et al. |
| 2003/0013692 A1* | 1/2003 | Gullans et al. ............ 514/179 |
| 2003/0181393 A1 | 9/2003 | Lampidis et al. |
| 2005/0043250 A1 | 2/2005 | Lampidis et al. |
| 2006/0025351 A1 | 2/2006 | Lampidis et al. |
| 2008/0194652 A1 | 8/2008 | Smilkstein |
| 2011/0189310 A1* | 8/2011 | Hempstead ................ 424/722 |

FOREIGN PATENT DOCUMENTS

| | | | |
|---|---|---|---|
| WO | 01/82926 | 11/2001 | |
| WO | WO 2006/010283 | * 2/2006 | ............. A61K 31/00 |
| WO | 2006/128670 | 12/2006 | |
| WO | 2007/025613 | 3/2007 | |
| WO | 2010/042728 | 4/2010 | |

OTHER PUBLICATIONS

Galluzzi et al. Cell Death and Differentiation 2007, 14, 1237-1243.*
Aksenova et al. Current Neurovascular Research 2005, 2, 73-89.*
Definition of Prevent, Princeton University "About WordNet." WordNet. Princeton University. 2010. <http://wordnet.princeton.edu>; retrieved from internet Sep. 18, 2012.*
Saito et al. Molecular Neurobiology 2005, 31, 105-116.*
Singh et al. J. Cardiovasc. Pharmacol. Ther. 2003, 8 (2), 135-148.*
Aragones et al., "Deficiency or inhibition of oxygen sensor Phd1 induces hypoxia tolerance by reprogramming basal metabolism," Nat. Genet., 40:170 (2008).
Bonnet et al., "A mitochondria-K+ channel axis is suppressed in cancer and its normalization promotes apoptosis and inhibits cancer growth," Cancer Cell, 11:37 (2007).
Brunton and Parker, Goodman and Gilman's The Pharmacological Basis of Therapeutics, The McGraw-Hill Companies, ed. 11, p. 1889 (2006).
Buttner et al., "Functional mitochondria are required for alpha-synuclein toxicity in aging yeast," J. Biol. Chem., 283:7554-7560 (2008).
Chen et al., "Modulation of electron transport protects cardiac mitochondria and decreases myocardial injury during ischemia and reperfusion," Am. J. Physiol. Cell. Physiol., 292:C137-C147 (2007).
Clemo et al., "The Optical Rotatory Powers of Some 4-Substituted Benzhydrylamines," in The Optical Rotatory Powers, pp. 1958-1960 (1939).
DeBerardinis et al., "Beyond aerobic glycolysis: transformed cells can engage in glutamine metabolism that exceeds the requirement for protein and nucleotide synthesis," PNAS USA, 104:19345 (2007).

(Continued)

*Primary Examiner* — Sreeni Padmanabhan
*Assistant Examiner* — Irina Neagu
(74) *Attorney, Agent, or Firm* — Fish & Richardson P.C.

(57) ABSTRACT

Model systems have shown that shifting a cell's reliance from oxidative phosphorylation (OXPHOS) to glycolysis can protect against cell death. Exploiting the therapeutic potential of this strategy, however, has been limited by the lack of clinically safe agents that remodel energy metabolism. The present invention identifies non-toxic small molecules (e.g., drug-like compounds) that are capable of modulating oxidative metabolism. One identified compound comprises meclizine. As described herein, meclizine, and its enantiomer S-meclizine, redirects OXPHOS to glycolysis. Such compounds could be protective or therapeutic in degenerative disorders such as diabetes, Huntington's, Parkinson's, and Alzheimer's disease and/or ischemic disorders including, but not limited to, stroke, heart attack, or reperfusion injuries.

9 Claims, 54 Drawing Sheets

(56) References Cited

OTHER PUBLICATIONS

Ellison et al., "Phosphoethanolamine and ethanolamine are decreased in Alzheimer's disease and Huntington's disease," Brain Res., 417:389-392 (1987).
Food and Drug Administration, Federal Register, 52:15866 (1987).
Fukui et al., "Cytochrome c oxidase deficiency in neurons decreases both oxidative stress and amyloid formation in a mouse model of Alzheimer's disease," Proc. Natl. Acad. Sci. USA, 104:14163 (2007).
Fullerton et al., "Developmental and metabolic effects of disruption of the mouse CTP:phosphoethanolamine cytidylyltransferase gene (Pcyt2)," Mol. Cell. Biol., 27(9):3327-3336 (2007).
Fullerton et al., "The development of a metabolic disease phenotype in CTP:phosphoethanolamine cytidylyltransferase-deficient mice," J. Biol. Chem., 18; 284(38):25704-27513 (2009).
Giaccia et al., "HIF-1 as a target for drug development," Nat. Rev. Drug. Discov., 2:803 (2003).
Gohil et al., "Nutrient-sensitized screening for drugs that shift energy metabolism from mitochondrial respiration to glycolysis," Nature Biotechnology, published online at doi:10.1038/nbt.1606 on Feb. 14, 2010.
Golenser et al., "Current perspectives on the mechanism of action of artemisinins," Int. J. Parasitol., 36:1427 (2006).
Gusella et al., "A polymorphic DNA marker genetically linked to Huntington's disease," Nature, 306:234 (1983).
Hochberg et al., "More powerful procedures for multiple significance testing," Stat. Med., 9:811 (1990).
Huber et al., "Graded reoxygenation with chemical inhibition of oxidative phosphorylation improves posthypoxic recovery in murine hippocampal slices," J. Neurosci. Res., 75:441 (2004).
Huber et al., "Improved posthypoxic recovery in vitro on treatment with drugs used for secondary stroke prevention," Neuropharmacology, 48:558 (2005).
Hunter et al., "Can radiation-induced apoptosis be modulated by inhibitors of energy metabolism?" Int. J. Radiat. Biol., 83:105-114 (2007).
International Search Report as issued in PCT/US2010/034985 on Feb. 25, 2011.
Jackson et al., "Polyglutamine-Expanded Human Huntingtin Transgenes Induce Degeneration of Drosophila Photoreceptor Neurons," Neuron, 21:633-642 (1998).
Jeong et al., "Modification of glycolysis affects cell sensitivity to apoptosis induced by oxidative stress and mediated by mitochondria," Biochem. Biophys. Res. Commun., 313:984 (2004).
Johnson et al., "Characterization of transcription factors and cis-acting elements that regulate human CTP: phosphoethanolamine cytidylyltransferase (Pcyt2)," Biochim. Biophys. Acta., 1735(3):230235 (2005).
Knott et al., "Mitochondrial fragmentation in neurodegeneration," Nat. Rev. Neurosci., 9:505 (2008).
Leikin et al., Poisoning and Toxicology Handbook (Informa Health Care), pp. 430 (2008).
Leverve et al., "Mitochondrial metabolism and type-2 diabetes: a specific target of metformin," Diab. Metab., 29:6S88-94 (2003).
Lin et al., "Induction of apoptosis and cell-cycle arrest in human colon cancer cells by meclizine," Food and Chemical Toxicology, 45:935-944 (2007).
Lu et al., "Induction of pyruvate dehydrogenase kinase-3 by hypoxia-inducible factor-1 promotes metabolic switch and drug resistance," J. Biol. Chem., 283:28106 (2008).
Marroquin et al., "Circumventing the Crabtree effect: replacing media glucose with galactose increases susceptibility of HepG2 cells to mitochondrial toxicants," Tox. Sciences, 97(2):539-547 (2007).
Martins et al., "Plasmodium berghei-infected mice: lack of effect of meclizine and cimetidine on the development of pulmonary oedema," Ann. Trop. Med. Parasitol., 80(5):491-499 (1986).
Miyazaki et al., "Effects of thioperamide, a histamine H3-receptor antagonist, on a scopolamine-induced learning deficit using an elevated plus-maze test in mice," Life Sci., 57:2137 (1995).
Modica-Napolitano et al., "Ethanolamine and phosphoethanolamine inhibit mitochondrial function in vitro: implications for mitochondrial dysfunction hypothesis in depression and bipolar disorder," Biol. Psychiatry, 55:273 (2004).
Mootha et al., "En-alpha and Gabpa/b specify PGC-1 alpha-dependent oxidative phosphorylation gene expression that is altered in diabetic muscle," PNAS USA, 101:6570 (2004).
Mootha et al., "Maximum oxidative phosphorylation capacity of the mammalian heart," Am. J. Physiol., 272:H769 (1997).
Moyes et al., "Control of muscle bioenergetic gene expression: implications for allometric scaling relationships of glycolytic and oxidative enzymes," J. Exp. Biol., 208:1601 (2005).
Nadtochiy et al., "Different mechanisms of mitochondrial proton leak in ischaemia/reperfusion injury and preconditioning: implications for pathology and cardioprotection," Biochem. J., 395:611-618 (2006).
Nakashima et al., "Cloning of a human cDNA for CTP-phosphoethanolamine cytidylyltransferase by complementation in vivo of a yeast mutant," J. Biol. Chem., 272(14):9567-9572 (1997).
Opalka et al., "A Novel Synthesis of the Enantiomers of an Antihistamine Drug by Piperazine Formation from a Primary Amine," Synthesis, 766-768 (1994).
Parikh et al., "TXNIP regulates peripheral glucose metabolism in humans," PLoS Medicine, 4:e158 (2007).
Parker et al., "Expanded polyglutamines in Caenorhabditis elegans cause axonal abnormalities and severe dysfunction of PLM mechanosensory neurons without cell death," Proc. Natl. Acad. Sci. USA, 98:13318 (2001).
Parker et al., "Resveratrol rescues mutant polyglutamine cytotoxicity in nematode and mammalian neurons," Nat. Genet., 37:349 (2005).
Poloumienko et al., "Genomic organization and differential splicing of the mouse and human Pcyt2 genes," Gene 21; 325:145-155 (2004).
Reitzer et al., "Evidence that glutamine, not sugar, is the major energy source for cultured HeLa cells," J. Biol. Chem., 254:2669 (1979).
Robinson et al., "Nonviability of cells with oxidative defects in galactose medium: a screening test for affected patient fibroblasts," Biochem. Med. Metab. Biol., 48:122 (1992).
Rossignol et al., "Energy substrate modulates mitochondrial structure and oxidative capacity in cancer cells," Cancer Research, 64:985-993 (2004).
Sarang et al., "Discovery of molecular mechanisms of neuroprotection using cell-based bioassays and oligonucleotide arrays," Physiol. Genomics, 11:45-52 (2002).
Tijburg et al., "Ethanolamine-phosphate cytidylyltransferase," Methods Enzymol., 209:258-263 (1992).
Toyota et al., "Behavioral characterization of mice lacking histamine H(3) receptors," Mol. Pharmacol., 62:389 (2002).
Trettel et al., "Dominant phenotypes produced by the HD mutation in STHdh(Q111) striatal cells," Hum. Mol. Genet., 9:2799 (2000).
Varma et al., "Inhibitors of metabolism rescue cell death in Huntington's disease models," Proc. Natl. Acad. Sci. USA, 104:14525 (2007).
Vincent et al., "Can drug screening lead to candidate therapies for testing in diabetic neuropathy?," Antioxidants & Redox Signaling, 10(2):387-393 (2008).
Wagner et al., "Large-scale chemical dissection of mitochondrial function," Nat. Biotechnol., 26:343 (2008).
Wang et al, "Inhibitors of cytochrome c release with therapeutic potential for Huntington's disease," The Journal of Neuroscience, 28(38):9473-9485 (2008).
Warburg, "On the origin of cancer cells," Science, 123:309 (1956).
Wheeler et al., "Long glutamine tracts cause nuclear localization of a novel form of huntingtin in medium spiny striatal neurons in HdhQ92 and HdhQ111 knock-in mice," Hum. Mol. Genet., 1(9):503 (2000).
Wojtovich and Brookes, "The complex II inhibitor atpenin A5 protects against cardiac ischemiareperfusion injury via activation of mitochondrial KATP channels," Basic Res. Cardiol., 104:121-129 (2009).
Zhu et al., "Regulation of the mouse CTP: phosphoethanolamine cytidylyltransferase gene Pcyt2 during myogenesis," Gene, 447(I):51-59 (2009).
Zhu et al., "Stimulation of the human CTP:phosphoethanolamine cytidylyltransferase gene by early growth response protein 1," J. Lipid Res., 49:2197 (2008).

(56) References Cited

OTHER PUBLICATIONS

Supplementary European Search Report issued in EP 10775629 on Sep. 25, 2012.

Adachi, "Cerebral ischemia and brain histamine," Brain Res. Brain Res. Rev., 2005;50(2):275-86.

Brodeur et al. (Eds.), Principles and practice of pediatric oncology (5th edn.), J B Lippincott Company, Philadelphia (2006), pp. 933-970.

Chang et al., "Effectiveness and safety of extracranial carotid stent placement: A nationwide self-controlled case-series study," J. Formos Med. Assoc., 2014; pii: S0929-6646(14)00153-3.

Gohil et al., "Meclizine inhibits mitochondrial respiration through direct targeting of cytosolic phosphoethanolamine metabolism," J. Biol. Chem., 2013;288(49):35387-95.

Gohil et al., "Nutrient-sensitized screening for drugs that shift energy metabolism from mitochondrial respiration to glycolysis," Nat. Biotechnol., 2010;28(3):249-55.

Gross et al., "Evidence for a role of opioids in epoxyeicosatrienoic acid-induced cardioprotection in rat hearts," Am. J. Physiol. Heart Circ. Physiol., 2010;298(6):H2201-7.

Hu and Chen, "Role of histamine and its receptors in cerebral ischemia," ACS Chem Neurosci., 2012;3(4):238-47.

Labiche and Grotta, "Clinical trials for cytoprotection in stroke," NeuroRx, 2004;1(1):46-70.

Maslov et al., "Opioid peptide deltorphin II simulates the cardioprotective effect of ischemic preconditioning: role of $\delta_2$-opioid receptors, protein kinase C, and K(ATP) channels," Bull. Exp. Biol. Med., 2010;149(5):591-3.

Ristow et al., "Antioxidants prevent health-promoting effects of physical exercise in humans," Proc. Natl. Acad. Sci. USA, 2009;106(21):8665-70.

Shuaib et al., "NXY-059 for the treatment of acute ischemic stroke," N. Eng. J. Med., 2007; 357:562-71.

Sundaresan et al., "Requirement for generation of $H_2O_2$ for platelet-derived growth factor signal transduction," Science, 1995;270(5234):296-9.

Office Action issued in EP10775629.8 on Mar. 25, 2015 (7 pages).

* cited by examiner

→ 10 μM Meclizine
→ 25 μM Meclizine
→ 50 μM Meclizine

| Gene Symbol | Fold change |
|---|---|
| LOC401805 | 1.66 |
| DUSP6 | 1.49 |
| ERRFI1 | 1.46 |
| VEGFA | 1.34 |
| PVR | 1.27 |
| HIF3A | 1.20 |
| TUBB3 | 1.04 |
| UGP2 | 0.86 |
| RAPGEF6 | 0.85 |
| SLC38A6 | 0.79 |
| TXNIP | 0.60 |
| ➡ GLS | 0.58 |
| INSIG1 | 0.52 |
| LDLR | 0.46 |

Ommatidia of mutant Htt
(Q128/128) expressing fly at day 0

FIG. 24A
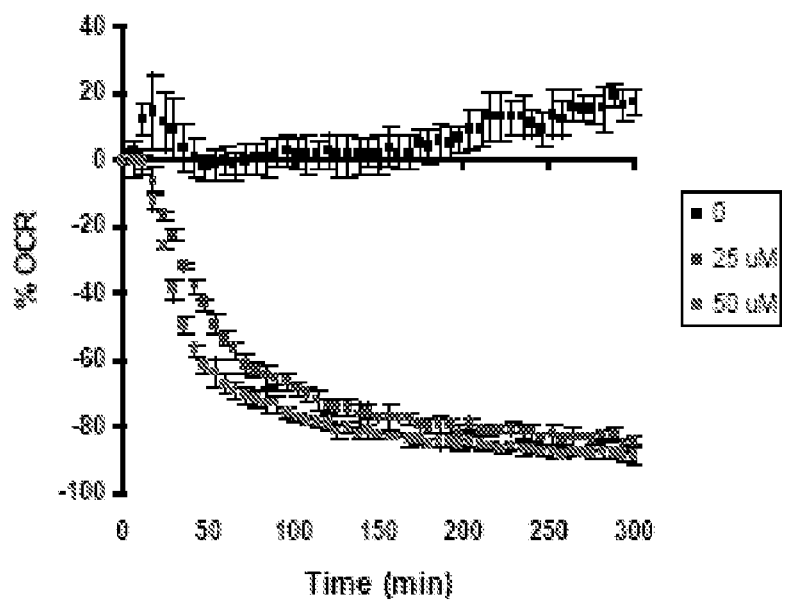
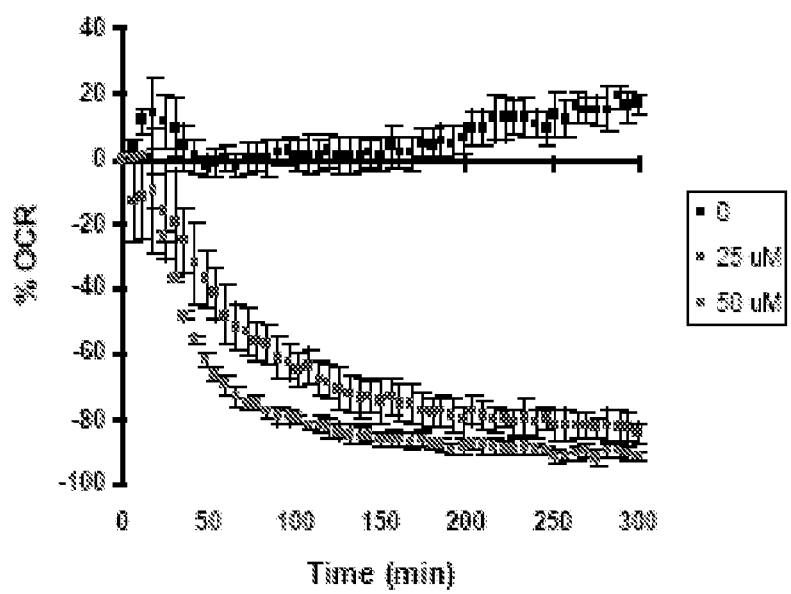
FIG. 24B

FIG. 27B

| | Compound | R1 | R2 | Cn | -N(R3)(R4) | Sglu/gal | FcAvg glu/gal |
|---|---|---|---|---|---|---|---|
| Subclass III | thiethylperazine | 2-CH₃CH₂S- | H | -(CH₂)₃- | ~N\_/N- | 0.15 | 1.41 |
| | Sufenazine | 2-CF₃- | H | | ~N\_/N-\_OH | -0.01 | 0.57 |
| | Promethazine | H | H | -CH₂CH- / CH₃ | ~N(CH₃)(CH₃) | 0.30 | 1.01 |
| | Trimeprazine | H | H | -CH₂CHCH₂- / CH₃ | | -0.07 | 0.35 |

FIG. 28

| Chem BankID | PubChem _SID | Pub chem | Compound | Structure | FcAvg glu/gal |
|---|---|---|---|---|---|
| 801 | 11488673 | 2729 | Chlorprothixene hydrochloride | 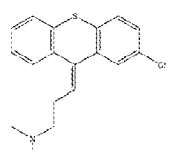 | 1.55; 0.85 |
| 927 | 11488505 | 26987 | Clemastine fumarate | C* = R 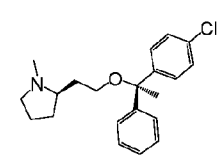 | 1.54; 0.84 |
| 1035 | 11487926 | 4034 | Meclizine | 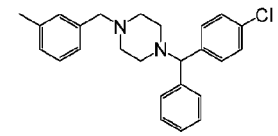 | 1.43; 1.08 |
| 3188276 | 11468216 | 3085006 | Thiethylperazine malate | 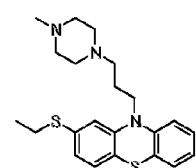 | 1.41 |
| 809 | 11488813 | 4543 | Nortriptyline hydrochloride | 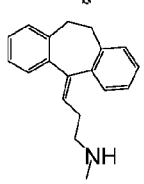 | 1.27 |

| Chem BankID | PubChem_SID | Pubchem | Compound | Structure | FcAvg glu/gal |
|---|---|---|---|---|---|
| 1431 | 11489412 | 2805 | cloperastine hydrochloride | 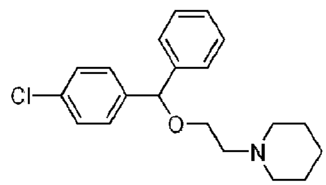 | 1.26; 1.17 |
| 1510 | 11489802 | 4098 | methapyrilene hydrochloride | 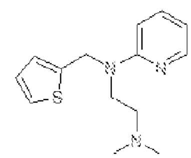 | 1.2; 1.01 |
| 884 | 11489093 | 4761 | pheniramine maleate | 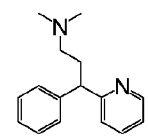 | 1.16; 0.94 |
| 1060 | 11467442 | 4822 | Pimethixene maleate | 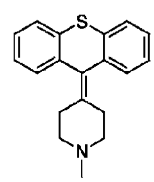 | 1.15 |
| 1537011 | 11489426 | 6834 | Brompheniramine maleate | 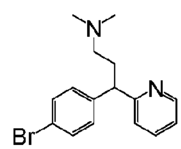 | 1.12; 1.03 |
| 3480341 | 11488465 | 2267 | azelastine hydrochloride | 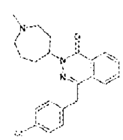 | 1.1 |
| 746 | 11489075 | 2200 | antazoline phosphate | 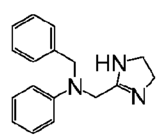 | 1.1; 0.97 |
| 1443 | 11488854 | 4601 | Orphenadrine hydrochloride | 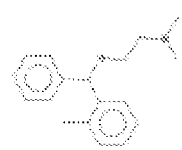 | 1.1; 1.05 |

| Chem BankID | PubChem_SID | Pub chem | Compound | Structure | FcAvg glu/gal |
|---|---|---|---|---|---|
| 1434 | 11489019 | 4184 | Mianserine hydrochloride | 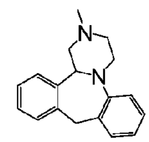 | 1.09; 0.96 |
| 938 | 11488661 | 5588 | Triprolidine hydrochloride | 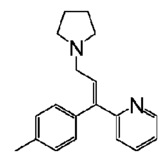 | 1.08; 0.84 |
| 1152 | 11488773 | 5587 | tripelennamine citrate | 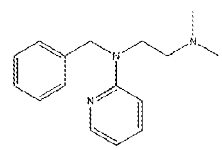 | 1.08 |
| 1000807 | 11488990 | 6726 | cyclizine | 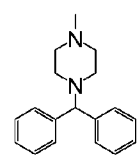 | 1.04; 1.02 |
| 3174102 | 11488816 | 25096 | hydroxyzine pamoate | 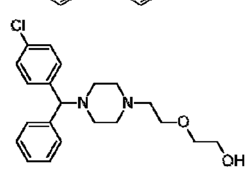 | 1.04; 0.97 |
| 1590 | 11467286 | 5405 | Terfenadine | 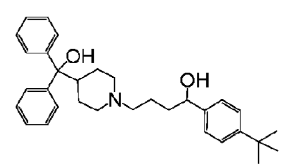 | 1.04 |
| 3045799 | 11488852 | 3325 | famotidine | 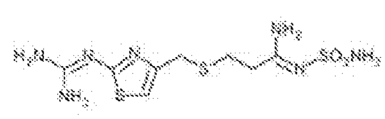 | 1.02 |
| 709 | 11489548 | 2247 | Astemizole | 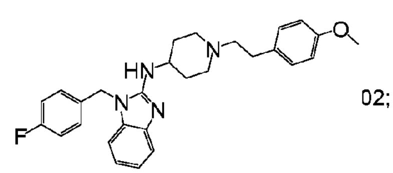 | 02; 0.69 |

| Chem BankID | PubChem _SID | Pub chem | Compound | Structure | FcAvg glu/gal |
|---|---|---|---|---|---|
| 1389 | 11489400 | 3957 | loratadine | 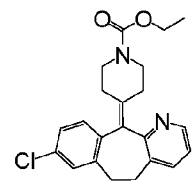 | 1.02 |
| 681 | 11488656 | 4927 | Promethazine hydrochloride | 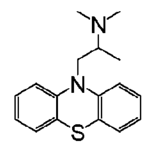 | 1.01; 0.89 |
| 1412 | 11488943 | 2564 | carbinoxamine maleate | 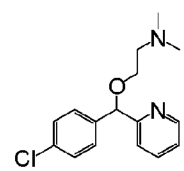 | 1.01 |
| 1059 | 11487949 | 3158 | doxepin hydrochloride | 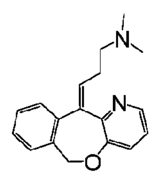 | 0.99 |
| 771 | 11489014 | 3827 | Ketotifen fumarate | 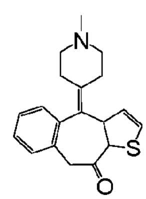 | 0.99; 0.97 |
| 1141 | 11487922 | 2344 | benztropine | 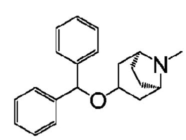 | 0.98 |
| 3174101 | 11488496 | 5702169 | mebhydrolin naphthalenesulfonate | 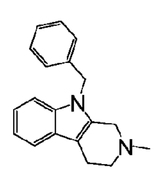 | 0.98 |
| 1432 | 11487931 | 3162 | Doxylamine succinate | 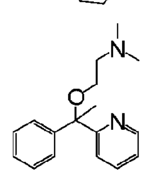 | 0.98; 0.89 |

| Chem BankID | PubChem_SID | Pub chem | Compound | Structure | FcAvg glu/gal |
|---|---|---|---|---|---|
| 1130 | 11489015 | 3372 | flufenazine hydrochloride | 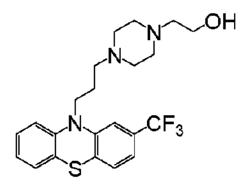 | 0.97 |
| 1068 | 11489241 | 5039 | ranitidine | 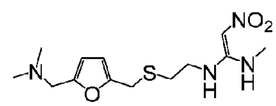 | 0.96; 0.92 |
| 885 | 11489061 | 2170 | Amoxapine (amoxepine) | 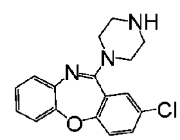 | 0.96; 0.9 |
| 3173092 | 11488808 | 10660 | dimenhydrinate | 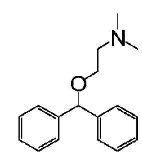 | 0.95 |
| 3480106 | 11488995 | 3348 | fexofenadine | 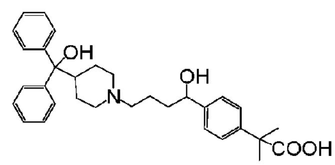 | 0.95 |
| 2069230 | 11487972 | 716121 | chlorpheniramine (s) maleate | 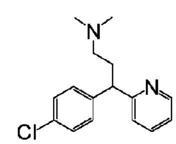 | 0.93; 0.84 |
| 1002 | 11488777 | 3100 | Diphenhydramine hydrochloride | 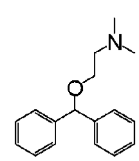 | 0.93; 0.91 |
| 1441 | 11488798 | 3103 | diphenylpyraline hydrochloride | 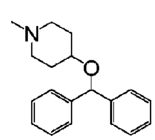 | 0.92; 0.91 |
| 830 | 11489122 | 4992 | Pyrilamine maleate | 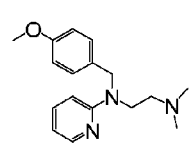 | 0.91; 0.80 |

FIG. 28 (cont.)

| Chem BankID | PubChem_SID | Pub chem | Compound | Structure | FcAvg glu/gal |
|---|---|---|---|---|---|
| 809 | 11488813 | 4543 | nortriptyline | 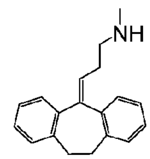 | 0.9 |
| 3044756 | 11488774 | 5702128 | trimeprazine tartrate | 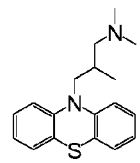 | 0.85 |
| 1052338 | 11488356 | 46695 | salsoline | 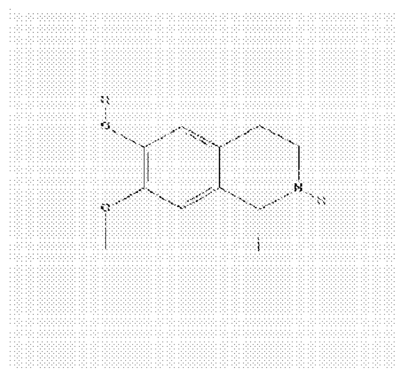 | 0.85 |

FIG. 29

| Chem BankID | PubChem_SID | Pubchem | Compound | Structure (Diphenylpiperazine) | FcAvg glu/gal | Average FcAvg glu/gal |
|---|---|---|---|---|---|---|
| 1035 | 11487926 | 4034 | Meclizine | | .43; 1.08 | Ave = 1.26 |
| | | | chlorcyclizine | | 1.4 | |

FIG. 29 (cont.)

| Chem BankID | Pub Chem_SID | Pubchem | Compound | Structure (Diphenylpiperazine) | FcAvg glu/gal | Average FcAvg glu/gal |
|---|---|---|---|---|---|---|
| | | | flunarizine | | 1.33 | |
| | | | cinnarazine | | 1.02, 1.2 | Ave = 1.11 |
| 1000807 | 11488990 | 6726 | cyclizine | | 1.04; 1.02 | Ave = 1.03 |
| 3174102 | 11488816 | 25096 | hydroxyzine pamoate | | 1.04; 0.97 | Ave = 1.01 |
| | | | homochlorcyclizine | | 1 | |
| | | | cetirizine | | 0.93 | |
| | | | SDZ- 201106 | | | |

| Chem BankID | Pub Chem_SID | Pub chem | Compound | Structure | FcAvg$_{glu/gal}$ (AVG) |
|---|---|---|---|---|---|
| | | | |  Diphenylalkyl | |
| | | | Pimozide |  | 1.31 |
| | | | Lidoflazine |  | 1.16 |
| | | | Fluspirilen |  | 1.1.2 |
| 884 | 11489093 | 4761 | pheniramine maleate | 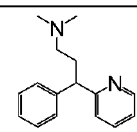 | 1.16; 0.94 (1.05) |
| 2069230 | 11487972 | 716121 | chlorpheniramine (s) maleate | 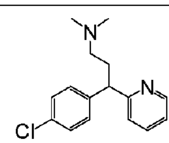 | 0.93; 0.84 (0.885) |
| 1537011 | 11489426 | 6834 | Brompheniramine maleate | 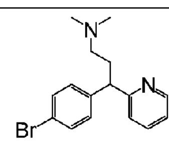 | 1.12; 1.03 (1.075) |
| 938 | 11488661 | 5588 | Triprolidine hydrochloride | 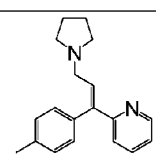 | 1.08; 0.84 (0.96) |

| Chem BankID | Pub Chem_SID | Pub chem | Compound | Structure | FcAvg glu/gal (AVG) |
|---|---|---|---|---|---|
| 1590 | 11467286 | 5405 | Terfenadine | 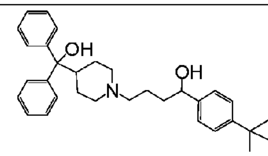 | 1.04 |
| 3480106 | 11488995 | 3348 | fexofenadine | 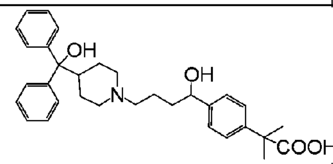 | 0.95 |
|  |  |  | Azacyclonol |  | 0.83 |
|  |  |  | Diphenidol |  | 1.067 |
|  |  |  | Protriptyline |  | 0.98 |

| Chem BankID | Pub Chem_SID | Pub chem | Compound | Structure | FcAvg glu/gal (Avg) |
|---|---|---|---|---|---|
|  |  |  |  | <br>Diphenylalkoxyl |  |
| 1431 | 11489412 | 2805 | cloperastine hydrochloride | 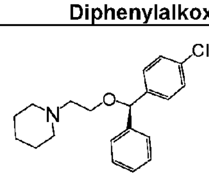 | 1.26; 1.17 (1.22) |

FIG. 31 (cont.)

| Chem BankID | Pub Chem _SID | Pub chem | Compound | Structure | FcAvg glu/gal (Avg) |
|---|---|---|---|---|---|
| 927 | 11488505 | 26987 | Clemastine fumarate | C* = R | 1.54; 0.84 (1.19 |
| 1443 | 11488854 | 4601 | Orphenadrine hydrochloride | 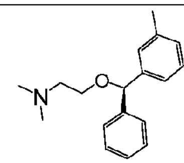 | 1.1; 1.05 (1.08) |
| 1412 | 11488943 | 2564 | carbinoxamine maleate | 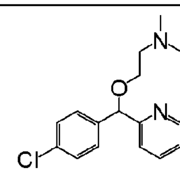 | 1.01 |
| 1141 | 11487922 | 2344 | benztropine | 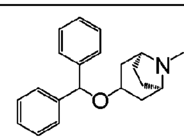 | 0.98 |
| 1432 | 11487931 | 3162 | Doxylamine succinate | 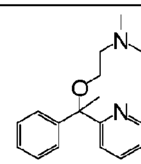 | 0.98; 0.89 (0.935) |
| 3173092 | 11488808 | 10660 | dimenhydrinate | 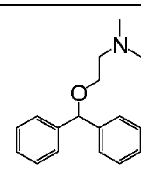 | 0.95 |
| 1002 | 11488777 | 3100 | Diphenhydramine hydrochloride | 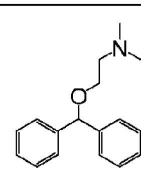 | 0.93; 0.91 (0.92) |
| 1441 | 11488798 | 3103 | diphenylpyraline hydrochloride | 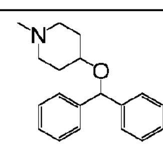 | 0.92; 0.91 (0.92) |

FIG. 32

| Chem BankID | Pub Chem_SID | Pub chem | Compound | Structure | FcAvg glu/gal (Avg) |
|---|---|---|---|---|---|
| | | | | Tricyclic | |
| 801 | 11488673 | 2729 | Chlorprothixene hydrochloride | 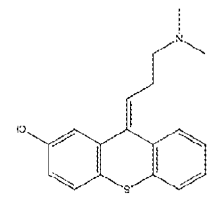 | 1.55; 0.85 (1.2) |
| 1060 | 11467442 | 4822 | Pimethixene maleate | 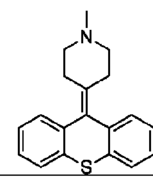 | 1.15 |
| 809 | 11488813 | 4543 | Nortriptyline hydrochloride | 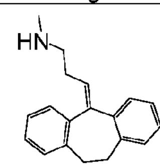 | 1.27; 0.9 (1.9) |
| 1389 | 11489400 | 3957 | loratadine | 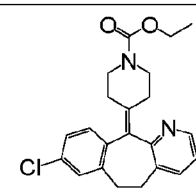 | 1.02 |
| 1059 | 11487949 | 3158 | doxepin hydrochloride | 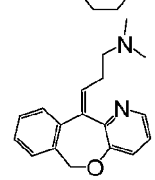 | 0.99 |
| 771 | 11489014 | 3827 | Ketotifen fumarate | 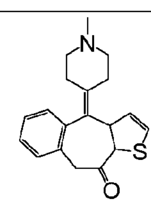 | 0.99; 0.97 |
| 3188276 | 11468216 | 3085006 | Thiethyl-perazine malate | 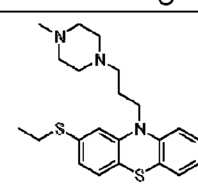 | 1.41 |

FIG. 32 (cont.)

| Chem BankID | Pub Chem_SID | Pub chem | Compound | Structure | FcAvg glu/gal (Avg) |
|---|---|---|---|---|---|
| 681 | 11488656 | 4927 | Promethazine hydrochloride | 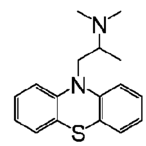 | 1.01; 0.89 |
| 3044756 | 11488774 | 5702128 | trimeprazine tartrate | 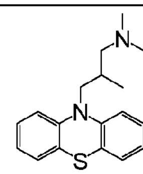 | 0.85 |
| 1130 | 11489015 | 3372 | flufenazine hydrochloride | 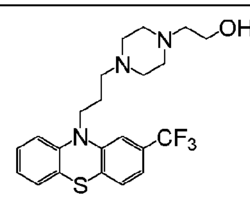 | 0.97 |
| 1434 | 11489019 | 4184 | Mianserine hydrochloride | 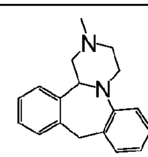 | 1.09; 0.96 |
| 885 | 11489061 | 2170 | Amoxapine (amoxepine) | 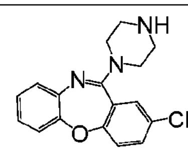 | 0.96; 0.9 |
| 3174101 | 11488496 | 5702169 | mebhydrolin naphthalenesulfonate | 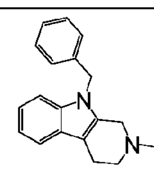 | 0.98 |

FIG. 33B  FIG. 33C

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 1
gcacagacat ggttggtata t                                      21

<210> SEQ ID NO 2
<211> LENGTH: 54
<212> TYPE: DNA
<213> ORGANISM: Artificial Sequence
<220> FEATURE:
<223> OTHER INFORMATION: synthetically generated oligonucleotide

<400> SEQUENCE: 2
ggggacaagt ttgtacaaaa aagcaggctc caccatgatg cggctgcgag gctc      54

<210> SEQ ID NO 3
<211> LENGTH: 50
<212> TYPE: DNA
<213> ORGANISM: Artificial Sequence
<220> FEATURE:
<223> OTHER INFORMATION: synthetically generated oligonucleotide

<400> SEQUENCE: 3
ggggaccact ttgtacaaga aagctgggtc caacaatcca tcaagattct            50

METHODS AND COMPOSITIONS FOR TREATING DEGENERATIVE AND ISCHEMIC DISORDERS

CLAIM OF PRIORITY

This application is a 371 application of International Application No. PCT/US2010/034985, filed on May 14, 2010, and claims the benefit of U.S. Provisional Patent Application Ser. Nos. 61/178,191, filed on May 14, 2009, and 61/234,788, filed on Aug. 18, 2009, the entire contents of which are hereby incorporated by reference.

FIELD OF THE INVENTION

This invention is related to modulation of energy metabolism. Energy metabolism modulators have been identified using a chemical screening strategy to identify small molecule suppressors of mitochondrial metabolism (e.g., of oxidative phosphorylation). For example, such suppressors of mitochondrial metabolism may have use to prevent and/or treat neurodegenerative and/or ischemic diseases, diabetes, and parasitic infection. For example, meclizine has been identified as an inhibitor of mitochondrial respiration (i.e., a high $S_{glu/gal}$ inhibitor of oxidative phosphorylation in the mitochondria) and protects against neurodegenerative disease-induced cell death, ischemic injury, and diabetes, e.g., type 2 diabetes.

Also provided are methods of treating a subject who is afflicted with parasites, e.g., protozoan parasites that rely solely on the Kennedy pathway for synthesis of phosphatidylethanolamine, including species *trypanosoma* and *plasmodia*.

BACKGROUND

Virtually all cells have the capacity to shift their relative reliance on glycolysis versus oxidative phosphorylation (OXPHOS), based on nutrient availability, environmental conditions, or stages of growth and differentiation. Additionally, some have suggested that shifts in energy metabolism can contribute to disease pathogenesis. For example, it has long been recognized that cancer cells exhibit higher rates of glycolysis (Warburg, *Science* 123:309 (1956)), perhaps to promote survival under hypoxic conditions or to support rapid cell proliferation. Recent studies have demonstrated that redirecting metabolism towards OXPHOS, using dichloroacetate, can actually retard tumor growth (Bonnet et al., *Cancer Cell* 11:37 (2007)).

Conversely, recent studies in cellular and animal models have shown that partial inhibition of OXPHOS via genetic or pharmacologic means can suppress the toxicity of disease alleles associated with neurodegenerative disorders (Buttner et al., *J Biol Chem* 283:7554 (2008); Fukui et al, *Proc Natl Acad Sci USA* 104:14163 (2007); and Varma et al., *Proc Natl Acad Sci USA* 104:14525 (2007)) as well as in suppressing the cell death observed in animal models of stroke (Huber et al., *J Neurosci Res* 75:441 (2004)) and cardiac ischemia reperfusion (Chen et al., *Am J Physiol Cell Physiol* 292:C137 (2007)). The underlying mechanism of protection is unclear but it has been suggested that flux through a damaged or compromised mitochondrial respiratory chain may contribute to the pathology, and that by redirecting energy metabolism towards glycolysis, it may be possible to minimize oxidative damage and suppress apoptosis (Jeong et al., *Biochem Biophys Res Commun* 313:984 (2004); and Hunter et al., *Int J Radiat Biol* 83:105 (2007)).

Clinically useful agents with which to shift a cell's reliance from OXPHOS to glycolysis are currently unavailable. For example, classic poisons of OXPHOS, such as rotenone, antimycin, cyanide, and oligomycin, have many disadvantages by: i) acting quickly and directly to interrupt respiration with extremely high potency and efficacy; ii) acutely depleting ATP in oxidative tissues, thereby stalling the numerous biochemical pathways coupled to the respiratory chain; iii) causing rapid cell toxicity; and iv) causing death in humans, at even at low doses.

SUMMARY

The present invention is based, at least in part, on the identification of small molecule suppressors of mitochondrial metabolism. The suppressors of mitochondrial metabolism identified herein may be useful to prevent and/or treat neurodegenerative and/or ischemic diseases For example, meclizine has been identified as a disrupter of mitochondrial metabolism and protects against neurodegenerative disease and induced cell death, ischemic injury, and diabetes, e.g., type 2 diabetes.

Thus, in a first aspect, the invention provides methods for treating subjects who have a condition associated with cell death associated with ischemic insult or a cellular degenerative disease. The methods include selecting a subject who has a condition associated with cell death associated with ischemic insult or cellular degenerative disease (e.g., selecting them on the basis that they have the condition); and administering to the subject a composition comprising a therapeutically effective amount of a compound identified as an OXPHOS inhibitor as described herein, e.g., a compound listed in table 1 or 3, e.g., meclizine or an S-enantiomer thereof. In general, where meclizine is mentioned herein, the use of S-meclizine can be inferred, except where S-meclizine is specifically excluded. Thus in the methods described herein either S-meclizine or meclizine (racemate) can be used, though in some situations one will be preferred over the other for reasons discussed herein.

In a second aspect, the invention features methods for reducing the risk of developing a condition associated with cell death associated with ischemic insult or a cellular degenerative disease in subjects. The methods include selecting a subject who has or is at risk of developing a condition associated with cell death associated with ischemic insult or cellular degenerative disease ((e.g., selecting them on the basis that they have or are at risk of developing the condition); and administering to the subject a therapeutically effective amount of a compound identified as an OXPHOS inhibitor as described herein, e.g., a compound listed in table 1 or 3, e.g., meclizine or an S-enantiomer thereof.

In a further aspect, the invention provides methods for treating diabetes in a subject. The methods include selecting a subject who has or is at risk of developing type 2 diabetes e.g., a subject who has the metabolix syndrome, is obese, or is insulin resistant, or has any of the other known identified risk factors for type 2 diabetes; and administering to the subject a composition comprising a therapeutically effective amount of a compound identified as an OXPHOS inhibitor as described herein, e.g., a compound listed in table 1 or 3, e.g., meclizine or an S-enantiomer thereof.

Also described herein are the use of meclizine or an S-enantiomer thereof in the treatment or prevention of a condition associated with cell death associated with ischemic insult or a cellular degenerative disease, and the use of meclizine or an S-enantiomer thereof in the treatment or prevention of type 2 diabetes.

In addition, the present invention includes methods of administering S-meclizine for treating or preventing nausea, vomiting, and dizziness caused by motion sickness, or for vertigo (or dizziness) caused by certain inner ear problems, e.g., for the treatment of conditions that are presently treated with the meclizine racemate.

Subjects, as used herein, are mammalian subjects, e.g., human subjects.

In some embodiments, the methods described herein include administering a therapeutically effective amount of S-meclizine, e.g., a composition a composition consisting essentially of S-meclizine.

In some embodiments, the methods described herein include administering a composition that is substantially free of the R-enantiomer of meclizine, e.g., that is at least about 92% pure, 95% pure, 97% pure, 99% pure; e.g., has a ratio of 99:1, 98:2, 97:3, 95:5, 96:4, 94:6, 93:7, 92:8, 91:9, 90:10, 85:15, 80:20 S-meclizine to R-meclizine.

In some embodiments, the cellular degenerative disease is a neurodegenerative disease, e.g., Parkinson's Disease, Alzheimer's Disease, Amyotrophic Lateral Sclerosis (ALS), Friedreich's ataxia, or Huntington's disease.

In some embodiments, the condition is an ischemia-reperfusion injury, e.g., myocardial ischemic injury, renal ischemic injury, or stroke.

In some embodiments, the methods include administering a dose of meclizine sufficient to produce a serum level of about 100 nM to 1 µM, e.g., at least a peak concentration of 100 nM, 500 nM, 750 nM, 1 µM.

In some embodiments, the meclizine is administered parenterally.

In some embodiments, the meclizine is administered in a daily dose of about 25 mg/day or more.

In a further aspect, the invention features methods for treating a subject who has or is at risk of having an infection with a parasite, e.g., a parasite in which phosphatidylethanolamine synthesis requires functional PCYT2 enzyme activity, e.g., in which phosphatidylethanolamine is synthesized predominantly via the Kennedy pathway. The methods include selecting a subject who has or is at risk of being exposed to the parasite; and administering to the subject a composition including a therapeutically effective amount of meclizine or an S-enantiomer thereof. In some embodiments, the methods include administering a therapeutically effective amount of S-meclizine, e.g., a composition a composition consisting essentially of S-meclizine. In some embodiments, the methods include administering a composition that is substantially free of the R-enantiomer of meclizine, e.g., that is at least about 92% pure, 95% pure, 97% pure, 99% pure; e.g., has a ratio of 99:1, 98:2, 97:3, 95:5, 96:4, 94:6, 93:7, 92:8, 91:9, 90:10, 85:15, 80:20 S-meclizine to R-meclizine. Also provided is the use of meclizine or S-meclizine in the treatment of an infection with a parasite.

In some embodiments, the parasite is selected from the group consisting of *Trypanosoma brucei*, *Trypanosoma cruzi*, and *Plasmodium falciparum*.

In yet another aspect, the invention features methods for identifying compounds for the treatment of a condition associated with cell death associated with ischemic insult or a cellular degenerative disease, e.g., as described herein. The methods include providing a sample comprising enzymatically active CTP:phosphoethanolamine cytidylyltransferase 2 (PCYT2); contacting the sample with a test compound; and determining activity of the PCYT2 in the sample in the presence and the absence of the test compound. A test compound that decreases activity of PCYT2 in the sample is a candidate compound for the treatment of the condition. In some embodiments, the sample is a living cell, and the method further includes determining phosphoethanolamine (PEA) levels in the cell in the presence and absence of the test compound, wherein a test compound that increases levels of PEA in the cell is selected as a candidate compound for treatment of the condition.

In some embodiments, the methods and compositions described herein comprise or use a compound having a benzhydrylamine-based structure. In some embodiments, the benzhydrylamine-based structure comprises a Substructure A1 (diphenylpiperazine) or A2. In some embodiments, the methods and compositions described herein comprise or use a compound having a tricyclic ring-based structure. In some embodiments, the tricyclic ring-based structure comprises Substructure E1, E2, F1, F2, G1, or G2. In some embodiments, the tricyclic ring-based structure comprises thiethylperazine. In some embodiments, the tricyclic ring-based structure comprises a compound including, but not limited to, those listed in FIG. 32.

In one aspect, the present invention contemplates a therapeutic composition comprising a meclizine enantiomer, e.g., the S-enantiomer, and a pharmaceutically acceptable carrier.

In some embodiments, the present invention contemplates a method, comprising: a) providing; i) a candidate compound, wherein said compound is suspected of modulating mitochondrial energy production; ii) a cell culture capable of growing in a plurality of carbon sources; b) screening the compound by switching the cell culture from a first carbon source to a second carbon source, and c) measuring a first cell culture growth rate and a second cell culture growth rate. In some embodiments, the first cell growth rate is measured with the first carbon source. In some embodiments, the second cell growth rate is measured with the second carbon source. In some embodiments, the first cell growth rate is less than the second cell growth rate, thereby identifying the compound as a glycolytic inhibitor. In some embodiments, the second cell growth rate is less than the first cell growth rate, thereby identifying the compound as an oxidative phosphorylation inhibitor. In some embodiments, the first carbon source comprises glucose. In some embodiments, the second carbon source comprises galactose. In some embodiments, the method further comprises determining a ratio of the first cell growth rate and the second cell growth rate. In some embodiments, the ratio comprises a log 10 transformation of the first cell growth rate. In some embodiments, the ratio comprises a log 10 transformation of the second cell growth rate. In some embodiments, the ratio comprises a log 10 transformation of the first cell growth rate and the second cell growth rate. In some embodiments, the ratio comprises a numerical value of between approximately 1.00 to (−) 1.00. In some embodiments, the compound is selected from the group consisting of a small organic molecule, a pharmaceutical, a nutraceutical, a nucleic acid, and a protein.

In some embodiments, the present invention contemplates a method, comprising: a) providing; i) a candidate compound, wherein said compound is suspected of being a selective inhibitor of OXPHOS; ii) a first cell culture grown in a glucose-rich media; iii) a second cell culture grown in a galactose-rich media; b) incubating said first cell culture in the presence of said candidate compound, wherein a glucose growth score is determined; c) incubating said second cell culture in the presence of said candidate compound, wherein a galactose growth score is determined; and d) identifying said compound as a selective inhibitor of OXPHOS by calculating a glucose/galactose growth score ratio, wherein said ratio ranges between approximately 0.01 and 1.00. In some embodiments, the compound is selected from the group consisting of a small organic molecule, a pharmaceutical, a nutraceutical, a nucleic acid, and a protein. In some embodiments, the compound comprises an anti-neoplastic compound.

In some embodiments, the present invention contemplates a method, comprising: a) providing; i) a compound, wherein said compound comprises a glu/gal growth score ratio ranging between approximately 1.00 and (−) 1.00; ii) a patient exhibiting at least one symptom of a disease; and b) administering said compound to said patient under conditions such that said at least one symptom of said patient is reduced. In some embodiments, the compound is selected from the group consisting of a small organic molecule, a pharmaceutical, a nutraceutical, a nucleic acid, and a protein. In some embodiments, the disease is selected from the group consisting of a degenerative disease, a hyperproliferative disease (e.g., a tumor or cancer), diabetes, an ischemic disease, or a parasitic infection.

In some embodiments, the present invention contemplates a method, comprising: a) providing; i) a compound, wherein said compound comprises a glu/gal growth score ratio ranging between approximately 0.01 and 1.00; ii) a patient exhibiting at least one symptom of a disease; and b) administering said compound to said patient under conditions such that said at least one symptom of said patient is reduced. In some embodiments, the disease is selected from the group consisting of a neurodegenerative disease, an ischemic disease, diabetes, and a parasite infection. In some embodiments, the compound comprises meclizine. In some embodiments, the compound is selected from the group consisting of a small organic molecule, a pharmaceutical, a nutraceutical, a nucleic acid, and a protein.

In some embodiments, the present invention contemplates a method, comprising: a) providing; i) a compound, wherein said compound comprises a glu/gal growth score ratio ranging between approximately (−) 0.01 and (−) 1.00; ii) a patient exhibiting at least one symptom of a hyperproliferative disease (e.g., a tumor or cancer); and b) administering said compound to said patient under conditions such that said at least one symptom of said patient is reduced. In some embodiments, the compound is selected from the group consisting of a small organic molecule, a pharmaceutical, a nutraceutical, a nucleic acid, and a protein.

In some embodiments, the present invention contemplates a kit comprising: a) a solid substrate comprising a cell culture media; b) a first container comprising a first carbon source; c) a second container comprising a second carbon source; and d) a set of instructions explaining how to identify a candidate compound as a non-toxic modulator of mitochondrial energy metabolism. In some embodiments, the solid substrate comprises a plurality of testing wells. In some embodiments, the testing wells comprise a cell culture. In some embodiments, the solid substrate is frozen. In some embodiments, the first carbon source comprises glucose. In some embodiments, the second carbon source comprises galactose. In some embodiments, the set of instructions provide for the determination of a cell growth ratio comparing the first carbon source with the second carbon source.

DEFINITIONS

The term "candidate compound" as used herein, refers to any compound (e.g., small organic molecule, peptide, hormone, nucleic acid) that may be screened for modulating mitochondrial energy production.

The term "carbon source" as used herein, refers to any compound that may be utilized by a cell biochemical pathway to produce energy (e.g., to produce adenosine triphosphate or nicotinamide adenine diphosphate). Carbon sources are usually a sugar compound (e.g., glucose, galactose, fructose, and hexose).

The term "growth rate" as used herein, refers to the cellular proliferation of a tissue, organ, or organism. For example, the growth rate of a cell culture may be determined by comparing the number of cells in a first sample to the number of cells in a second sample, wherein the samples are temporally separated. Alternatively, growth may be measured by assessing dimensional changes (i.e., shape, width, density etc) of a tissue, tissue culture, or organ.

The term "glycolytic inhibitor" as used herein, refers to any compound capable of interfering with glycolysis.

The term "oxidative phosphorylation inhibitor" as used herein, refers to any compound capable of interfering with the electron transport chain (e.g., an OXPHOS inhibitor).

The term "$S_{glu/gal}$ score" refers to any ratio that compares cell growth when glucose (glu) is used as a sole sugar source (e.g., a glucose-rich media) to cell growth when galactose (gal) is used as a sole sugar source (i.e, for example, a galactose-rich media). For example, the $S_{glu/gal}$ scores may be expressed as a log 10 transformation ranging between approximately 1.00 to (−) 1.00. A high $S_{glu/gal}$ score would be expected to have a value greater than 0 and may be useful in identifying OXPHOS inhibitors. A low $S_{glu/gal}$ score would be expected to have a value less than 0 and may be useful in identifying inhibitors of rapid cell proliferation.

The term "a galactose growth score" as used herein, refers to any quantitation of cell proliferation when galactose is used as the sole sugar source.

The term "a glucose growth score" as used herein, refers to any quantitation of cell proliferation when glucose is used as the sole sugar source.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, genetic, biochemical, or environmental influences.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In some embodiments, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" or "inhibitor" as used herein, refers to any compound capable of interacting with (e.g., attaching or binding to) a binding partner (e.g., a glycolytic or oxidative phosphorylation pathway enzyme) under conditions such that the binding partner becomes unresponsive to its natural ligands. Inhibitory compounds may include, but are not limited to, small organic molecules, antibodies, oligonucleotides, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is e.g., impregnated, incorporated, coated, in suspension with, in solution with, or mixed with the medium.

The term "drug" or "compound" as used herein, refers to any pharmacologically active substance capable of being administered that achieves a desired effect. Drugs or compounds can be synthetic or naturally occurring, non-peptide, proteins or peptides, oligonucleotides or nucleotides, polysaccharides or sugars.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to, a catheter, applicator gun, or syringe. A second exemplary method of administering is by a direct mechanism such as local tissue administration (e.g., extravascular placement), oral ingestion, transdermal patch, topical, inhalation, or by suppository.

The term "patient", as used herein, is a human or animal subject and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "effective amount" as used herein, refers to a particular amount of a pharmaceutical composition comprising a therapeutic agent (e.g., an OXPHOS inhibitor) that achieves a clinically beneficial result.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable," as used herein, refer to molecular entities and compositions that do not produce adverse, allergic, or other untoward reactions when administered to an animal or a human.

The term, "pharmaceutically acceptable carrier," as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated," as used herein, may refer to a peptide composition that has been subjected to treatment (e.g., fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (e.g., weight/weight and/or weight/volume). The term "purified to homogeneity" is used to include compositions that have been purified to "apparent homogeneity" such that there is single protein species (e.g., based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The terms "specific binding" or "specifically binding" when used in reference to the interaction of a small molecule and a protein or peptide means that the interaction is dependent upon the presence of a particular structure (e.g., a 2-or-3-dimensional structure) on a protein; in other words a small molecule is recognizing and binding to a specific protein structure rather than to proteins in general. For example, if a molecule is specific for structure "A", the presence of a compound containing structure "A" (or free, unlabelled "A") in a reaction containing labeled "A" and the molecule will reduce the amount of labeled "A" bound to the molecule.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE FIGURES

FIG. 18A: p-ERK; Thr$^{202}$ or Tyr$^{204}$ phosphorylation detection. FIG. 18B: p-AKT; Thr$^{308}$; phosphorylation detection.

FIG. 19A: Western blot analysis of protein extract from Htt-Q128 expressing *C. elegans*. FIG. 19B: Western blot analysis performed on lysates from elav-GAL4>UAS-Htt-Q128 adult *D. melanogaster* (ten day feeding period).

FIG. 22 presents exemplary data showing the expression of mutant Htt (Q128/128) in the photoreceptors of *Drosophila melanogaster*. Images were obtained by light microscopy using the pseudopupil technique.

FIGS. 24A-B present exemplary data showing the effectiveness of (R) and (S) meclizine on cellular oxygen consumption in human embryonic kidney 293 cells.

FIG. 25A: Control IR data as a function of glucose and oxygen. FIG. 25B: Protected IR data as a function of meclizine, glucose and oxygen.

FIG. 27B presents exemplary representative compounds of Subclass III phenothiazine structures.

FIG. 29 presents exemplary representative compounds of a diphenylpiperazine structure.

FIG. 32 presents exemplary representative compounds of a tricyclic ring structure.

FIGS. 33A-33C include data showing the protective effect of meclizine in isolated cardiomyocytes exposed to ischemia-reperfusion (I/R). FIG. 33A is a schematic showing experimental design. FIG. 33B is a histogram showing cardiomyocyte viability post I/R in control, untreated and drug treated cells (Mec, meclizine; Atrop, atropine; Phenir, pheniramine; Pyril, pyrilamine; Scopo, scopolamine FIG. 33C is a histogram showing $VO_2$ in cardiomyocytes post FR in control, untreated and meclizine treated cells.

FIG. 34A is a line graph showing percent rate pressure pre and post FR in cells vehicle (open circle) and meclizine treated (solid circle) hearts. FIG. 34B shows a line graph showing measured infarct size in vehicle (open circle) and meclizine treated (solid circle) hearts.

DETAILED DESCRIPTION OF THE INVENTION

Figure 1A:
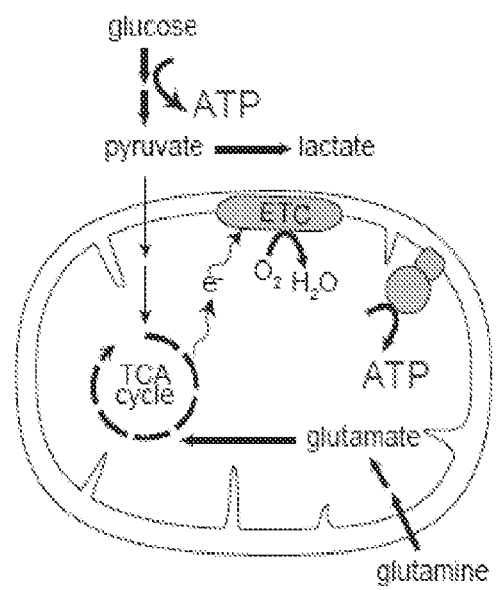
FIG. 1A illustrates a cell grown in glucose rich media deriving ATP from glycolysis and from oxidative metabolism.

As described herein, energy metabolism modulators were identified using a chemical screening strategy to identify small molecule suppressors of mitochondrial metabolism (e.g., oxidative phosphorylation and/or glycolysis). Meclizine was identified as a disrupter of mitochondrial metabolism that protects against cell death, e.g., cell death associated with ischemic insult or cellular degenerative disease, e.g., neurodegenerative disease or diabetes.

A chemical screening strategy aimed at identifying small molecules that induce metabolic switches, from mitochondrial respiration to aerobic glycolysis, or vice versa was performed. One small molecule identified by this screening strategy, meclizine, inhibited mitochondrial respiration and activated aerobic glycolysis, apparently via a novel metabolic mechanism, i.e., the inhibition of PCYT2. This representative drug was also shown to suppress a neurodegenerative disease phenotype in a cellular and animal model. In some embodiments, the present invention may utilized the plasticity of cellular metabolism for the development of novel therapeutics for a broad range of human diseases with links to energy homeostasis.

Although it is not necessary to understand the mechanism of an invention, it is believed that the described screening strategy involves metabolic state-dependent lethality and exploits the metabolic plasticity of mammalian cells. Most cells have the capacity to perform aerobic glycolysis or oxidative phosphorylation based on the available nutrients. Longer-term, adaptive switches between OXPHOS and glycolysis can take place during differentiation and development and can be driven by transcriptional and post-transcriptional mechanisms; see e.g., Moyes et al., *J. Exp Biol.* 208:1601 (2005).

Cells grown in the presence of glucose as a sole sugar source derive their ATP both from glycolysis as well as from mitochondrial oxidation of glutamine, with only a small fraction of the glucose carbon skeleton actually entering the TCA cycle (Reitzer et al., *J Biol Chem* 254:2669 (1979); and DeBerardinis et al., *PNAS USA* 104:19345 (2007). Cells grown in the presence of galactose, however, draw virtually all of their ATP from mitochondrial oxidation of glutamine, and the galactose carbon skeleton utilized for reductive biosynthesis. Metabolic-state dependent lethality screens may function as the mammalian version of the classic yeast growth assay in fermentable versus non-fermentable media. The approach has also been used to diagnose mitochondrial respiratory chain defects in humans. Robinson et al., *Biochem Med Metab Biol.*, 48:122 (1992).

The disclosed screening assays can be used to identify compounds, e.g., small molecules, that shift cellular metabolism towards OXPHOS and blunt growth and survival of cells growing rapidly (such compounds could have utility in treating cancer), as well as novel inhibitors of OXPHOS. The screening can be performed in intact cells, e.g., following 72 hours of drug treatment, and thereby identify agents that blunt OXPHOS via novel mechanisms, including agents that are relatively non-toxic in that they do not influence growth or survival when glucose is the sole sugar source.

Cellular Energy Metabolism and Disease

Mitochondria are cellular power plants that convert the food we eat into ATP, the cellular energy currency. A growing body of evidence suggests that inhibition of mitochondrial respiration can actually be protective in a variety of settings, including diabetes, Alzheimer's disease (AD), Parkinson's disease (PD), Huntington's disease (HD), and ischemic conditions such as stroke and myocaradial infarction.

How could shifting OXPHOS to glycolysis be protective? It has been suggested that mutated gene products in HD, AD, PD and ALS might physically interact with different components of the electron transport chain thereby leading to altered mitochondrial calcium handling, oxidative damage, and necrotic or apoptotic cell death. Knott et al., Nat Rev Neurosci 9:505 (2008). A functional mitochondrial respiratory chain may exacerbate the toxicity of a mutant protein. Modulating electron transport chain activity thus provides a potential means of reducing disease pathology, as has been suggested by genetic and chemical manipulation studies in cellular and animal models. See, e.g., Buttner et al., J Biol Chem 283, 7554 (2008); Fukui et al., Proc Natl Acad Sci USA 104, 14163 (2007); and Varma et al., Proc Natl Acad Sci USA 104:14525 (2007). Studies in models of AD, PD, and HD have shown that genetic or pharmacological inhibition of mitochondrial respiratory chain can suppress disease pathology. Mice deficient in neuron specific cytochrome c oxidase (complex IV) demonstrated fewer amyloid plaques and reduced oxidative damage when expressing the amlyoid precursor protein or presenilin 1. Fukui et al., *PNAS USA* 104: 14163 (2007). In yeast expressing α-synuclein, eliminating mitochondrial respiration by depleting mtDNA reduced reactive oxygen species (ROS) formation and apoptotic cell death; thus, suppression of mitochondrial function can suppress the toxicity arising from disease causing alleles. Buttner et al., *JBC* 283:7554-7560 (2008). The pharmacological inhibition of the respiratory chain by rotenone and oligomycin can prevent apoptotic cell death in cell culture as well as in vivo models of HD. Varma et al., *PNAS USA* 104:14525 (2007).

Metformin, an effective treatment for type diabetes, is believed to act in part by inhibiting the mitochondrial respiratory chain, thereby activating several adaptive pathways including enhancing AMP Kinase (AMPK) activity, which promotes glucose uptake in the periphery and suppress gluconeogenesis in the liver. Leverve et al., Diab. Metab. 29:6 S88-94 (2003). Metformin is presently one of the most widely-prescribed treatments for type 2 diabetes. Other compounds that act to inhibit OXPHOS, e.g., identified by a method described herein, e.g., meclizine or S-meclizine, are also candidate therapeutic agents for the treatment of diabetes.

Moreover, others have suggested that agents that block mitochondrial respiration can offer prophylaxis against the cell injury and death that follows ischemia and reperfusion in the heart, or in the brain. Chen et al., Am J Physiol Cell Physiol 292:C137 (2007), and Huber et al., Neuropharmacology 48:558 (2005), respectively. The neuroprotective effect of statins and other drugs used for secondary prevention of stroke could be due to their ability to cause mild inhibition of the mitochondrial respiratory chain. See, e.g., Huber et al., *Neuropharmacol* 48:558 (2005). Pretreatment with complex II inhibitor 3-nitropropionic acid (3-NPA) induced tolerance in mice subjected to focal, as well as global cerebral ischemia.

Figure 9:
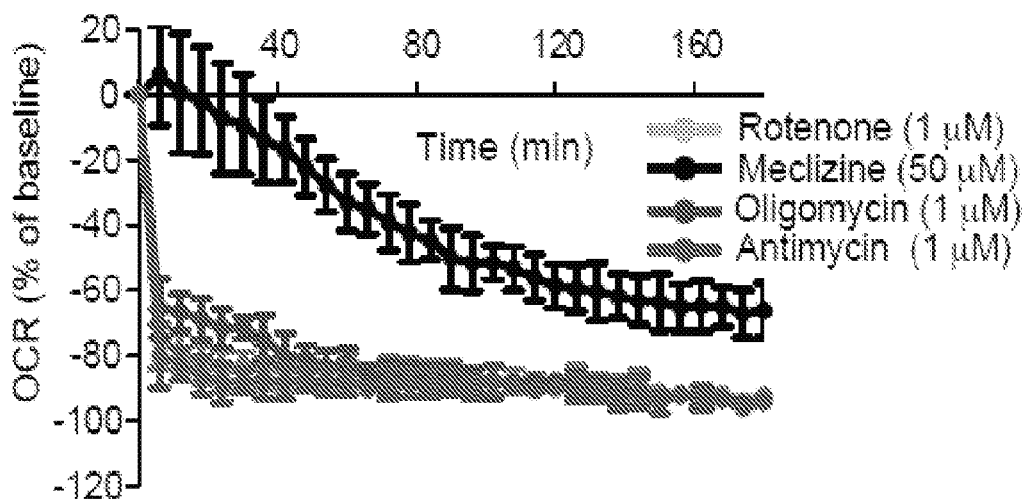
FIG. 9 is a line graph showing the time course of meclizine-mediated oxygen consumption rate (OCR) reduction over DMSO baseline compared to classical inhibitors of OXPHOS in 293 cells. Data are expressed as mean+/−SD (n≥3).

A major limitation to translating these previously reported findings for therapeutic benefit of OXPHOS inhibitors is the lack of clinically acceptable strategies for shifting the cell's reliance on mitochondrial respiration in humans. Currently available OXPHOS inhibitors directly interrupt the respiratory chain, exhibit a poor therapeutic index, and are poisonous. Given their rapid action, OXPHOS inhibitors tend to acutely interrupt active respiratory chains to generate free radical damage and acutely deplete cellular ATP, especially in oxidative cells. See, e.g., FIG. 9. Although the activation of the hypoxia-inducible factor pathway provide an alternate means of providing therapeutic potential by redirecting energy metabolism towards glycolysis, there are few clinically acceptable strategies to activate the pathway. Lu et al., *J Biol Chem* 283:28106 (2008); Aragones et al., *Nat Genet* 40:170 (2008); and Giaccia et al., *Nat Rev Drug Discov* 2:803 (2003).

In some embodiments, the present invention contemplates methods that allow titration of the amount or level of the reduction in OXPHOS, i.e., to partially attenuate rather than completely inhibit mitochondrial OXPHOS, such that toxic side effects associated with complete inhibition of OXPHOS are not produced or are minimized. (The ability to titrate can be assayed using a dose-response analysis; compounds that have an all-or-nothing response (e.g., a step-function response) are not suitable, as they are not titratable, whereas those agents that have a smooth dose-response curve are generally considered to be titratable). These agents are expected to have an improved therapeutic index.

In contrast, cells that are growing rapidly (such as tumor cells) rely primarily on glycolysis for energy. Thus, compounds identified as having a low Sglu/gal (e.g., compounds having a Sglu/gal ratio below zero, e.g., between −0.33 and −0.75) can be used as treatments for cancer or as adjuvants to other cancer treatments known in the art.

Lampidis et al., U.S. Pat. No. 7,338,940, discloses compositions and methods for cancer treatment by inhibiting glycolysis in anaerobically growing tumor cells (i.e., those cells at the tumor core) alone and/or in combination with inhibition of oxidative phosphorylation for the aerobically growing tumors cells (i.e., those cells at the tumor periphery) of the same tumor. The reference focuses upon six (6) classes of glycolysis inhibitors: i) 2 deoxy-D-glucose analogs; ii) D-hexopyranose analogs: iii) C-2 G-6P analogs; iv) C-3, C-4 G-6P analogs; v) glyceraldehyde analogs; and vi) lactate dehydrogenase inhibitors. Nevertheless, the reference discloses that oxidative phosphorylation inhibitors (i.e., rhodamine 123) causes an increase in lactic acid because the cells convert from aerobic to anaerobic metabolism. This condition increases their sensitivity to inhibitors of glycolysis. Further, the reference teaches that traditionally used anticancer agents (i.e., doxorubicin, vincristine, paclitaxel) are effective in an aerobic environment without lactic acid build-up (i.e., not reflecting an inhibition of oxidative phosphorylation). Consequently, the reference suggests that by using a method measuring lactic acid buildup may be used to screen extensive libraries of structurally diverse compounds to identify compounds that inhibit oxidative phosphorylation, thereby making the tumors sensitive to glycolysis inhibitors. Nonetheless, the reference does not teach comparing cell growth between glucose and galactose media to identify non-toxic glycolysis inhibitors that are effective anti-cancer agents. (dated Mar. 4, 2008; See also U.S. Pat. No. 7,160,865 (dated Jan. 9, 2007); U.S. Patent Application No. US 2006/0025351, 2005/0043250 and 2003/0181393; and WIPO Publication No. WO/2001/082926 selected parts.)

Rossignol et al., Cancer Research, 64:985-993, 2004 discloses use of glucose and galactose to investigate cancer cell adaptation to either glycolysis or oxidative phosphorylation depending upon the available energy source. Further the reference discloses that cancer cells can utilize glutaminolysis, oxidation of glutamine, when glucose is not available and cancer cells are specialized to generate energy by glycolysis. The reference does not teach comparing cell growth between glucose versus galactose media to identify non-toxic inhibitors of either oxidative phosphorylation or glycolysis.

Methods of Treatment

Because of their ability to modulate oxidative phosphorylation (OXPHOS) in mitochondria, the compositions identified by a method described herein, e.g., the compounds described herein, can be used to treat or delay development of human diseases where OXPHOS activity may contribute to pathogenesis, or where the inhibition of OXPHOS may activate cellular adaptive programs that can help prevent disease. For example, diseases associated wherein mitochondrial OXPHOS activity contributes to pathogenesis; these diseases include, but are not limited to, diabetes, e.g., type 2 diabetes; neurodegenerative diseases; and ischemic-reperfusion injuries, e.g., stroke, renal ischemic injury and, ischemic heart disease. In addition, conditions associated with parasitic infection with certain protozoan parasites can also be treated, as describe below. All of these conditions can be treated using a compound identified as an inhibitor of OXPHOS, e.g., a compound having a high Sglu/gal score, e.g., meclizine.

For example, screened drugs having a Sglu/gal score above zero may have potential therapeutic use for neurodegenerative or ischemic diseases, diabetes, or parasitic infections, as a non-toxic OXPHOS inhibitor. Identified compounds, exemplified herein by meclizine, can be used as or developed into therapeutics for diseases the pathogenesis of which stems from mitochondrial OXPHOS activity, e.g., as described herein. Alternatively, screened drugs having an Sglu/gal score below zero may have potential therapeutic use for cancer.

As described herein, meclizine targets PCYT2 and thus disrupts synthesis of phosphatidylethanolamine, a major phospholipid class in all eukaryotic cells. phosphatidylethanolamine can be synthesized by (i) the CDP-ethanolamine branch of the Kennedy pathway; (ii) decarboxylation of phosphatidylserine; or (iii) base exchange with phosphatidylserine. In mammals including humans, all three pathways are available. However, in certain protozoan pathogens including *Trypanosoma brucei*, the causative agent of human and animal African Trypanosomiasis (sleeping sickness), *Trypanosoma cruzi*, a parasite that causes Chagas disease, and *Plasmodium falciparum*, the human malaria parasite, phosphatidylethanolamine is predominantly synthesized via the Kennedy pathway. Thus, compounds like meclizine that disrupt this pathway by targeting PCYT2 can be used as therapeutic agents for the treatment of diseases associated with these parasites that rely on a PCYT2-mediated pathway for phosphatidylethanolamine synthesis.

Cellular Degenerative Diseases

The methods described herein include the treatment of disorders associated with cellular degeneration, e.g., neurodegeneration. The methods can include administration of a compound with a high Sglu/gal score, e.g., meclizine, to subject who have or are at risk of developing a degenerative disease. Diseases that can be treated by these methods include, e.g., Alzheimer's Disease (AD), Parkinson's Disease (PD), Huntington's Disease (HD), amyotrophic lateral sclerosis (ALS), and Freidreich's ataxia. Inhibitors of mitochondrial metabolism have been shown to rescue cell death in Huntington's disease models (see, e.g., Varma et al, Proc Natl Acad Sci USA. 2007), and functional mitochondria have been shown to be required for alpha-synuclein toxicity in aging yeast (see, e.g., Buttner et al., J Biol Chem. 2008). As shown herein, meclizine confers protection against neuronal cell death and dystrophy in three different models of HD.

Diabetes

In addition, the methods described herein can be used to treat diabetes. Inhibiting the mitochondrial respiratory chain activated several adaptive pathways including enhancing AMP Kinase (AMPK) activity, which promotes glucose uptake in the periphery and suppress gluconeogenesis in the liver. Leverve et al., Diab. Metab. 29:6 S88-94 (2003). Metformin, which acts at least partly by this mechanism, is presently one of the most widely-prescribed treatments for type 2 diabetes. As described herein, meclizine and S-meclizine are capable of inhibiting OXPHOS and activating AMPK in cultured muscle cells (see FIG. 24C) and promote glucose uptake in cultured muscle cells (FIG. 36), and reduces blood glucose levels in R6 mice (FIG. 37).

Ischemic Disorders

The methods described herein include the treatment of ischemia-reperfusion associated diseases including myocardial ischemia, cerebral ischemia, and renal ischemia. For example, in subjects with or at risk of myocardial ischemia, the methods can be used to reduce myocardial damage during a cardiac procedure, e.g., cardiac transplant, percutaneous coronary intervention (PCI), or coronary artery bypass graft (CABG), and for acute protection against myocardial damage during periods of unstable angina. The methods can include administration of a compound with a high Sglu/gal score, e.g., meclizine, as an anti-anginal agent in patients with established coronary artery disease. In subjects with or at risk of kidney ischemia, compounds with a high Sglu/gal score, e.g., meclizine, can be used to reduce acute kidney injury (AKI) during CABG, and to reduce transplant injury. In subjects with or at risk of cerebral ischemia, compound with a high Sglu/gal score, e.g., meclizine, can be used to reduce risk of or damage from a stroke, e.g., during a carotid endarterectomy (CEA) or CABG, and for protection against secondary ischemia following a subarachnoid hemorrhage (SAH). In particular, the compounds can be used in patients presenting with a transient ischemic attack (TIA) or a minor stroke, or who are at high risk for a stroke or recurrent stroke within 30 days (e.g., individuals who have just had a hemorrhagic stroke, or are about to undergo a procedure that carries a risk of ischemia-reperfusion damage, e.g., an organ transplant, PCI, CABG, or CEA). When a subject is about to undergo a procedure that carries a risk of ischemia-reperfusion damage the compound can be administered prior to, during, or after the procedure.

Thus the compositions identified by a method described here as having a high Sglu/gal score, e.g., meclizine, are suitable for treating ischemic disorders including, but not limited to, stroke, ischemic heart disease (e.g., heart attack or angina pectoris), reperfusion injury.

Ischemic Heart Disease

Ischemic heart disease is a term that doctors use to describe patients who have congestive heart failure due to coronary artery disease. "Ischemic" means that an organ (such as the heart) is not getting enough blood and oxygen. Ischemic heart disease results when the arteries that bring blood and oxygen to the heart are blocked. There may be a build-up of cholesterol and other substances, called plaque, in the arteries that bring oxygen to heart muscle tissue. Ischemic heart disease is a common cause of congestive heart failure. Patients with this condition may at one time have had a heart attack, angina, or unstable angina. A few patients may not have noticed any previous symptoms. Ischemic heart disease is a common type of cardiomyopathy in the United States and affects approximately 1 out of 100 people, most often middle-aged to elderly men.

Risks for ischemic heart disease include, but are not limited to, personal or family history of heart attack, angina, unstable angina, atherosclerosis, or other coronary artery diseases, high blood pressure, smoking, diabetes, high fat diet, high cholesterol, and obesity.

Symptoms of ischemic heart disease include, but are not limited to, chest pain that is localized under the chest bone but may move (radiate) to the neck, jaw, back, shoulder, arm accompanied by a tight, pressure, crushing, and/or squeezing feelings (the pain may or may not be relieved by rest or nitroglycerin), palpitations, irregular or rapid pulse, shop mess of breath, cough, fatigue, weakness, faintness, decreased alertness or concentration, decreased daytime urine output, excessive urination at night, and overall swelling Tests measuring ejection fraction may be used to diagnose ischemic heart disease that includes, but are not limited to, echocardiogram, ventriculogram performed during a cardiac catheterization, gated SPECT, MRI of chest, ECG, or heart biopsy.

The goal of current treatments is to relieve symptoms and treat the cause of the condition. Several types of medications are currently prescribed, including, but not limited to, angiotensin converting enzyme inhibitors (e.g., captopril or lisinopril), beta-adrenergic blockers (e.g., metoprolol or carvedilol), or diuretics (e.g., furosemide (Lasix), spironolactone, or eplerenone. The methods described herein can include the use of such treatments in combination with meclizine, administering separately or in a single composition.

Cerebral Ischemia/Stroke

A stroke is an interruption of the blood supply to any part of the brain. A stroke is sometimes called a "brain attack." Approximately every 40 seconds, someone in the United States has a stroke. A stroke can happen when: i) a blood vessel that supplies blood to the brain is blocked by a blood clot (e.g., an ischemic stroke) or ii) a blood vessel breaks open, causing blood to leak into the brain (e.g., a hemorrhagic stroke). If blood flow is stopped for longer than a few seconds, the brain cannot get blood and oxygen. Brain cells can die, causing permanent damage.

Ischemic stroke is a common type of stroke. Usually this type of stroke results from clogged arteries, a condition called atherosclerosis. Fat, cholesterol, and other substances collect on the wall of the arteries, forming a sticky substance called plaque. Over time, the plaque builds up. This often makes it hard for blood to flow properly, which can cause the blood to clot. Other causes of clot-related ischemic stroke include, but are not limited to, an abnormal heart valve, endocarditis, or the presence of a mechanical heart valve. For example, a clot can form on a heart valve, break off, and travel to the brain. For this reason, those with mechanical or abnormal heart valves often are prescribed anti-coagulant drugs (e.g., coumadin).

Hemorraghic stroke is also a common type of stroke. Usually this type of stroke results from bleeding in the brain. It can occur when small blood vessels in the brain become weak and burst. Some people have defects in the blood vessels of the brain that make this more likely. The flow of blood that occurs after the blood vessel ruptures damages brain cells.

Ischemic stroke risk factors include, but are not limited to, high blood pressure, diabetes, family history, heart disease, high cholesterol, or increased age. Certain medications that make blood clots more likely can increase stroke risk (e.g., some oral contraceptives).

Hemorraghic stroke risk factors include, but are not limited to, alcohol use, bleeding disorders, cocaine use, or head injury.

The symptoms of stroke depend on what part of the brain is damaged. In some cases, a person may not even be aware that he or she has had a stroke. Symptoms usually develop suddenly and without warning. They may be episodic (occurring and then stopping) or they may slowly get worse over time. In general stroke symptoms can include, but are not limited to, change in alertness, coma, lethargy, sleepiness, stupor, unconsciousness, emotional withdrawal, difficulty speaking or understanding others, difficulty swallowing, difficulty writing or reading, headache, loss of coordination, loss of balance, unilateral motor difficulties, nausea or vomiting, seizure, unilateral sensation alterations, sudden confusion, weakness of any body part, or vision problems.

Testing to diagnose stroke can include, but is not limited to, performing a cerebral angiogram, complete blood count, prothrombin time, partial thromboplastin time, electrocardiogram (ECG) echocardiogram, carotid duplex ultrasound, head CT, head MRI, magnetic resonance angiography (MRA), CT angiography, or heart monitoring.

Current treatment usually involves immediate (i.e., within three hours of an ischemic stroke event) administration of a thrombolytic drug (e.g., tPA). It is important to note that if the stroke is hemorrhagic rather than ischemic, thrombolytics can make the damage worse. For hemorrhagic stroke, surgery may be required to remove pooled blood from the brain and to repair damaged blood vessels.

In other circumstances, anticoagulants such as heparin and Coumadin are used to treat strokes due to blood clots. Aspirin may also be used. Other medications may be needed to control other symptoms, including high blood pressure. Painkillers may be given to control severe headache. The goal of long-term treatment is to help the patient recover as much function as possible and prevent future strokes. The recovery time and need for long-term treatment differs from person to person. Depending on the symptoms, rehabilitation may include, but is not limited to, occupational therapy, physical therapy, or speech therapy.

Renal Ischemia

Figure 7A:
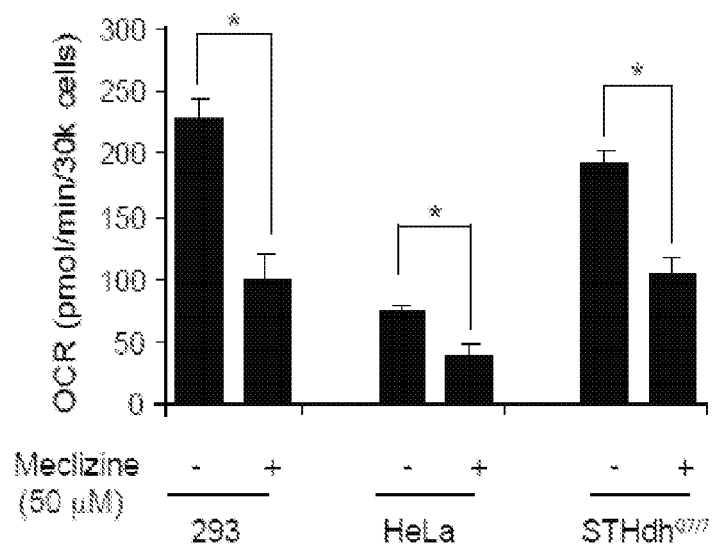
FIGS. 7A and 7B are bar graphs presenting exemplary data showing change in OCR and ECAR in multiple cell types after exposure to 50 μM meclizine or DMSO control for 200 minutes. Data expressed as mean+/−SD (n≥3). 7A, Change in oxygen consumption rate (OCR), and 7B, extracellular acidification rate (ECAR) in multiple cell types after exposure to 50 μM meclizine or DMSO control for 200 minutes in glucose containing media. Data are expressed as mean+/−SD (n≥3). * indicates P<0.05; p-values calculated by two-sided t-test.
Figure 7B:
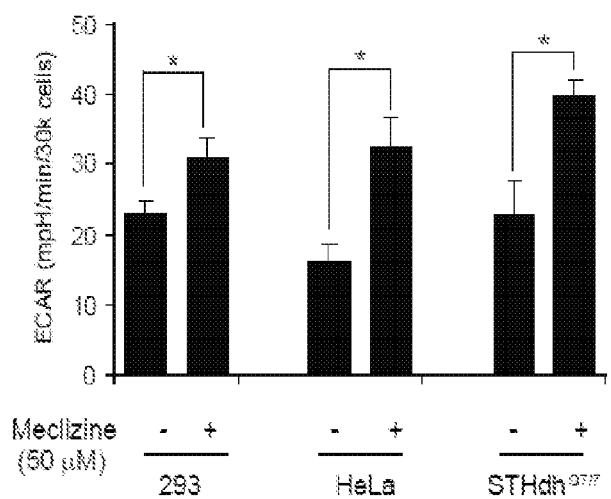
Figure 8A:
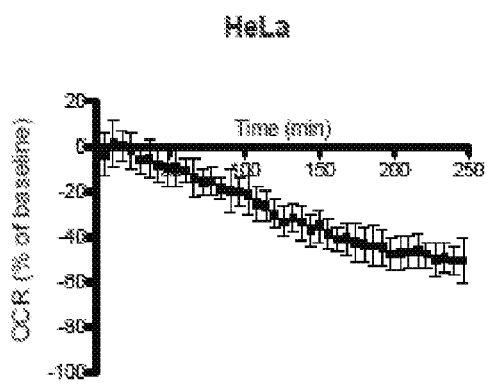
FIGS. 8A-F present exemplary data showing the effect of 50 μM meclizine on oxygen consumption rate (OCR) and extracelluar acidification rate (ECAR) in HeLa cells (FIGS. A and B), HEK 293 cells (FIGS. 8C and 8D), and in mouse immortalized striatal cells STHdhQ$^{7/7}$ (FIGS. 8E and 8F). Data is normalized to DMSO control; data is expressed as mean+/−SD (n≥3).
Figure 8B:
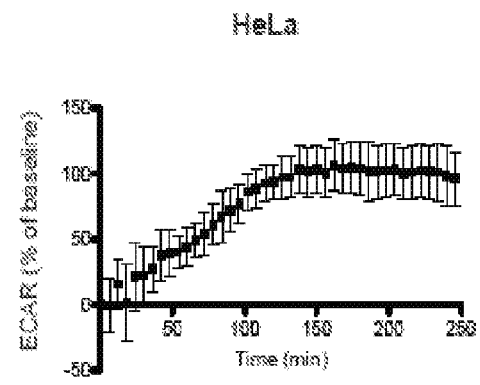
Figure 8C:
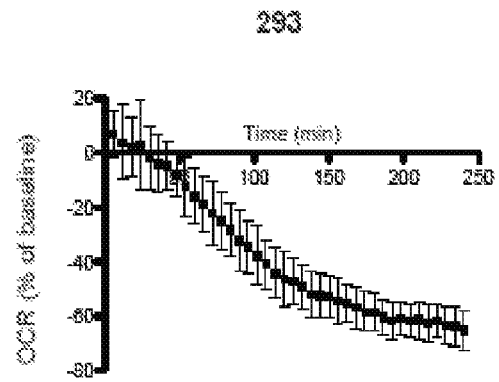
Figure 8D:
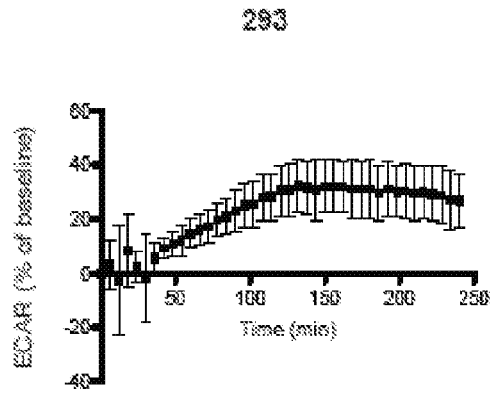
Figure 8E:
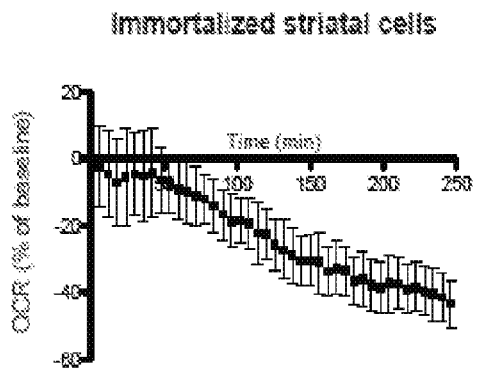
Figure 8F:
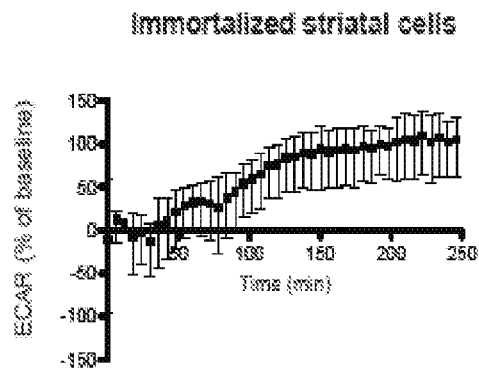

Acute kidney injury (AKI) can result from ischemic events in the kidney. For example, AKI occurs in up to 5% of all high risk surgeries such as coronary artery bypass graft (CABG) surgeries. Pretreatment with meclizine or S-meclizine may help prevent or reduce the damage associated with acute kidney injury. As shown herein, meclizine is capable of shifting respiration to glycolysis in human kidney-derived 293 cells (see FIGS. 7A and 7B).

Present Indications

In addition, the present invention proS-meclizine or a pharmaceutically acceptable salt thereof, e.g., S-meclizine hydrochloride, for indications for which the racemate is presently prescribed or administered (e.g., over the counter). Such conditions include those listed in the Merck Manual, e.g., nausea and vomiting associated with motion sickness (including chronic and acute motion sickness) and terminal diseases (e.g., in dying patients); and vertigo or dizziness caused by certain inner ear problems, e.g., benign positional vertigo, Meniere's disease, vestibular neuronitis, labyrinthitis; otitis media; trauma (e.g., tympanic membrane rupture, labyrinthine contusion, perilymphatic fistula, temporal bone fracture, postconcussion); acoustic neuroma; administration of ototoxins, e.g., ototoxic drugs; Herpes zoster oticus (Ramsay Hunt syndrome); and other central and peripheral nervous conditions.

Dizziness is generally used to describe various related sensations, including faintness (a feeling of impending syncope); light-headedness; feelings of imbalance or unsteadiness; or a vague spaced-out or swimmy-headed feeling. Vertigo is a false sensation of movement of the self or the environment. See Tucci, "Dizziness and Vertigo," in Ear, Nose, Throat, and Dental Disorders Approach to the Patient With Ear Problems, the Merck Manual, January 2009.

In some embodiments, the dosage of the S-meclizine administered for these indications is the same as that of the racemate.

Contraindication in Mitochondrial Disease/Inborn Errors of Mitochondrial Metabolism The term "mitochondrial diseases" (MD) refers to a group of disorders related to respiratory chain dysfunction; these disorders are known in the art. It is believed that compounds identified as having a high Sglul/gal score, e.g., as described herein, are likely to be toxic in subjects having mitochondrial disease; therefore, the methods can include determining if a subject has a mitochondrial disease and not administering such a compound to that subject, e.g., not administering meclizine to those subjects, and/or selecting a drug for treatment that does not have a high Sglu/gal.

Methods of Screening for Metabolic Modulator Compounds

A variety of organisms can switch between glycolytic and oxidative metabolism. This plasticity has been classically studied in yeast, which undergo a di-auxic shift when fermentable carbon sources are depleted from the growth media. In some embodiments, the methods described herein exploit this metabolic switching capability to discover safe and clinically effective drugs. Described herein is a cell-based assay strategy to identify compounds that selectively blunt the growth and survival of cells when they are reliant on OXPHOS versus glycolysis.

Figure 1B:
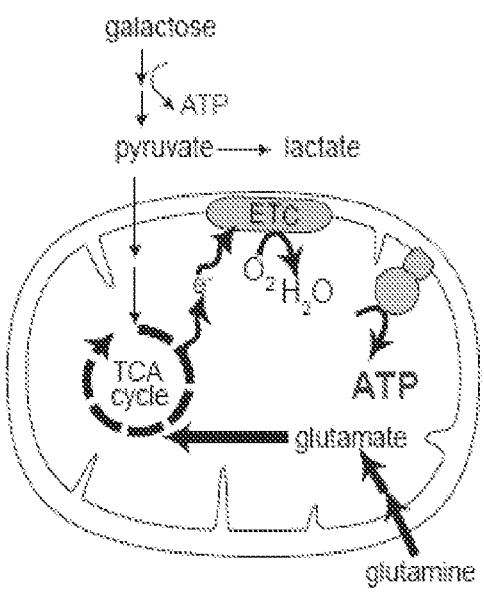
FIG. 1B illustrates a cell grown in galactose rich media deriving the majority of ATP from oxidative metabolism.
Figure 1C:
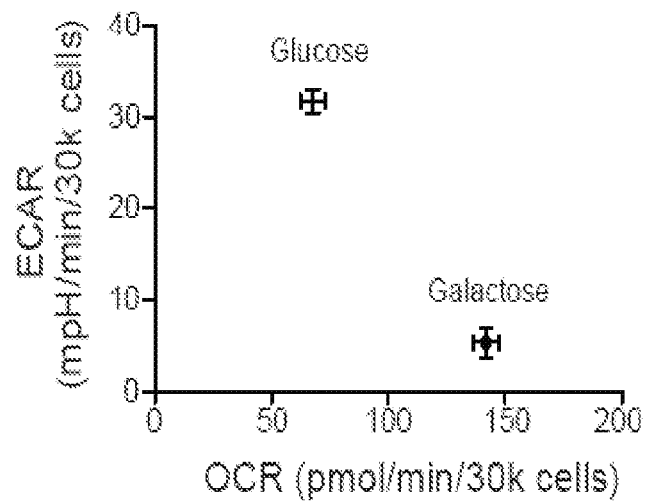
FIG. 1C provides exemplary data measuring extra-cellular acidification rate (ECAR) and oxygen consumption rate (OCR) of fibroblasts grown in 10 mM glucose or 10 mM galactose for three days. Data expressed as mean±SD (n=5).

Consistent with previous studies, the data presented herein shows that when human fibroblasts are grown in glucose as the sole sugar source, they derive energy from aerobic glycolysis as well as glutamine oxidation in the mitochondrion. For example, when mammalian cells are cultured, the presence of glucose inhibits oxidative metabolism (e.g., the Crabtree effect), and isotope labeling experiments in HeLa cells have revealed that replacing glucose with galactose forces the cells to utilize glutamine-driven respiration to produce >98% of cellular ATP. See, e.g., DeBerardinis et al., *Proc Natl Acad Sci USA* 104:19345 (2007); and Reitzer et al., *JBC* 254:2669 (1979). See FIGS. 1A & 1B Immortalized human fibroblasts can switch between glycolytic and oxidative metabolism by changing the sugar source in their media by monitoring at least two measures of cellular physiology (e.g., extracellular acidification rate (ECAR) and oxygen consumption rate (OCR)). When grown in glucose as the sole sugar source, they derive energy from aerobic glycolysis as well as glutamine oxidation in the mitochondrion. However, when these cells are grown in galactose as the sole sugar source there is an almost complete switch to glutamine oxidation as evidenced by a 5-6 fold decrease in glycolytic rate, producing 3-4 fold less acid, and a 2 fold increase in oxygen consumption compared to when they are grown in glucose. See FIG. 1C.

Figure 1D:
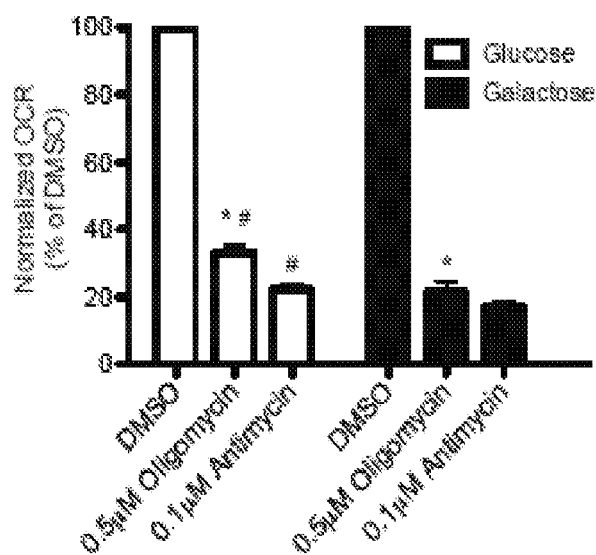
FIG. 1D presents exemplary data measuring OCR in fibroblasts grown in glucose and galactose after exposure to the oxidative inhibitors 0.5 µM oligomycin (complex V) and 0.1 µM antimycin (complex III). Data are expressed as mean±SD. * and # indicate p<0.05; p-values calculated by two-sided t-test (n=5).
Figure 1E:
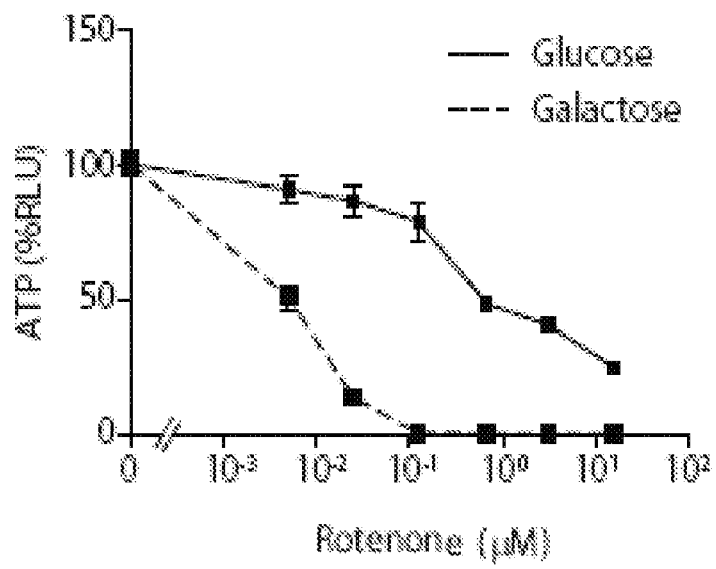
FIG. 1E presents exemplary data showing total cellular ATP levels (CellTiter-Glo®) in fibroblasts grown in either glucose rich media or galactose rich media in various concentrations of rotenone. Data expressed as mean±SD (n=5).
Figure 1F:
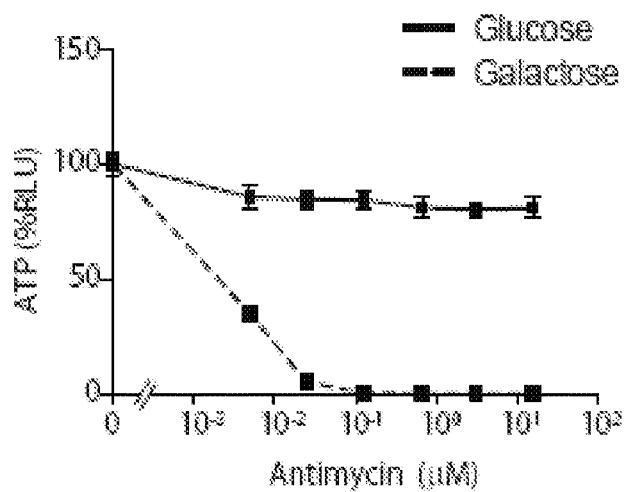
FIG. 1F presents exemplary data showing total cellular ATP levels (CellTiter-Glo®) in fibroblasts grown in either glucose rich media (10 mM) or galactose rich media (10 mM) in various concentrations of antimycin. Data expressed as mean±SD (n=5).
Figure 1G:
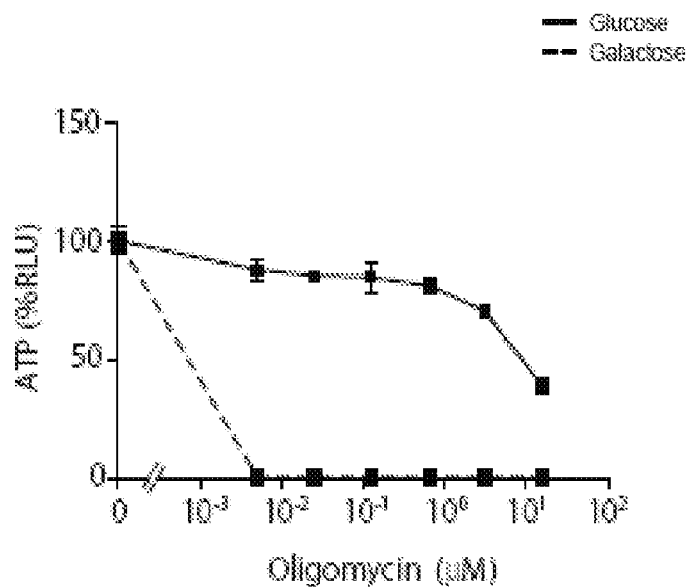
FIG. 1G presents exemplary data showing total cellular ATP levels (CellTiter-Glo®) in fibroblasts grown in either glucose rich media (10 mM) or galactose rich media (10 mM) in various concentrations of oligomycin. Data expressed as mean±SD (n=5).
Figure 1H:
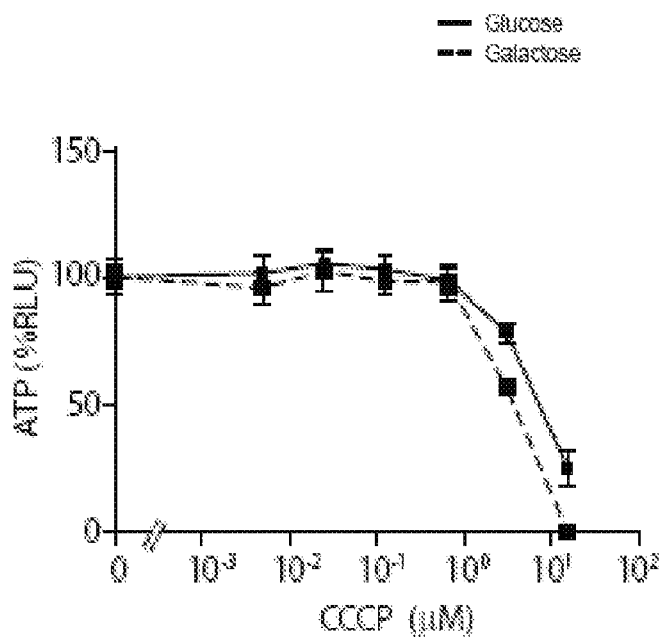
FIG. 1H presents exemplary data showing total cellular ATP levels (CellTiter-Glo®) in fibroblasts grown in either glucose rich media (10 mM) or galactose rich media (10 mM) in various concentrations of the uncoupler CCCP. Data expressed as mean±SD (n=5).

Additional data is shown describing mitochondrial bioenergetics under these two nutrient conditions. Treatment with antimycin and oligomycin can be used to quantify the level of total as well as uncoupled mitochondrial respiration. Using these agents, almost all mitochondrial respiration is coupled in the presence of galactose, whereas only approximately 15% of respiration is uncoupled in the presence of glucose. Treatment with oligomycin alone reveals that 60% of respiration in glucose is used for ATP production, whereas 80% of respiration is used for ATP production in galactose. See, e.g., FIG. 1D. Taken together, these results indicate that cells optimize the efficiency of OXPHOS for ATP generation in galactose media to compensate for reduced ATP synthesis coming from glycolysis.

A screening strategy described herein can be used for identifying small molecules that shift cellular energy metabolism. In some embodiments, the compounds may stimulate an endogenous inhibitor of OXPHOS; in some embodiments, the compounds decrease phosphoethanolamine cytidylyltransferase (PCYT2) activity. As described herein, meclizine inhibits the activity of PCYT2.

Thus, described herein are methods of screening small molecules in vitro to identify compounds that specifically inhibit PCYT2 activity; these compounds are identified as candidate compounds for the treatment of diseases and conditions described herein, e.g., ischemic and degenerative disorders. In some embodiments, a test compound is applied to a test sample, e.g., a cell or living tissue or organ, that expresses functional PCYT2, or a test sample comprising functional PCYT2, e.g., purified or recombinant PCYT2, and an effect of the test compound on PCYT2 activity is evaluated. In a cultured or primary cell for example, the ability of the test compound to inhibit PCYT2. In some embodiments, the methods can also include a screening step of identifying compounds that bind directly to PCYT2, e.g., to isolated PCYT2 using known binding assays.

PCYT2 genomic sequences have been described (Gene 21; 325:145-55 (2004)); the *homo sapiens* PCYT2 mRNA sequence can be found at GenBank Acc. No. NM_002861.2; the full-length protein can be found at GenBank Acc. No. NP_002852.1. See also Nakashima et al., J. Biol. Chem. 272 (14), 9567-9572 (1997) and Johnson et al., Biochim Biophys Acta. 1735(3):230-5 (2005).

Assays for PCYT2 activity are known in the art, including assays using $^{14}$C-phosphoethanolamine as a substrate. Commercially available assays such as the biochemical assays by Invitrogen, Millipore, Sigma-Aldrich, R&D Systems, Cell Signaling Technology, and/or Enzo Life Sciences. See also Zhu et al., Gene 447(1):51-59 (2009); Tijburg et al., Methods Enzymol 209:258-63 (1992); and Fullerton et al., Mol Cell Biol. 2007 May; 27(9):3327-36. Antibodies to human PCYT2 are available from Invitrogen, Millipore, Sigma-Aldrich, R&D Systems, Cell Signaling Technology, Abeam, Abnova, Novus Biologicals, and/or Epitomics.

In some embodiments, the small molecules are screened separately on cells grown in the presence of either glucose or galactose. Although it is not necessary to understand the mechanism of an invention, it is believed that the glucose assay assesses cell growth resulting from glycolysis. It is further believed that the galactose assay assesses cell growth resulting from mitochondrial oxidative phosphorylation activity.

In some embodiments, the present invention contemplates evaluating the effectiveness of screened small molecules by comparing the glucose cell growth data to the galactose cell growth data. In some embodiments, the comparison comprises a glucose/galactose ratio (e.g., a glu/gal score). In some embodiments, a high glu/gal score indicates selective inhibition of oxidative metabolism. In some embodiments, a low glu/gal score indicate a selective inhibition of glycolysis. In some embodiments, a glu/gal score is useful to identify effective inhibitors of either pathway that are non-toxic to the mitochondria. In some embodiments, the method comprising identifying a plurality of different compounds that are selective inhibitors of oxidative phosphorylation. In some embodiments, the method contemplates identifying activators of glycolysis (i.e., shown by increased cell growth in the presence of glucose) or drugs that simultaneously inhibit oxidative phosphorylation and activate glycolysis.

In some embodiments, clinically used drugs (e.g., FDA approved) are identified that target cellular energy metabolism having broad-based therapeutic implications for a spectrum of human diseases.

One such small molecule (e.g., meclizine), an over the counter antiemetic medication, with excellent penetration across the blood:brain barrier, inhibits mitochondrial respiration. Although it is not necessary to understand the mechanism of an invention, it is believed that meclizine may inhibit mitochondrial respiration via a novel metabolic mechanism, e.g., inhibition of PCYT2. Furthermore, meclizine is shown to suppress disease pathology in cellular and animal models of neurodegenerative and ischemic disease and diabetes, demonstrating the therapeutic potential for this and other mitochondrial respiratory inhibitor compounds identified by the methods described herein.

In some embodiments, the screening strategy described herein can be used to identify small molecules that selectively inhibit mitochondrial oxidative phosphorylation (OXPHOS). Mammalian cells are able to generate adenosine triphosphate (ATP) either from glycolysis or from respiration (e.g., OXPHOS), depending on the sugar source that is provided in the culture media. Rietzer et al., *JBC* 254:2669 (1979); and Rossignol et al., *Cancer Res* 64:985 (2004). This flexibility was exploited and a small molecule viability screening method designed to discover compounds that are not overtly toxic to cells. In some embodiments, the screen can be used to identify compounds that are conditionally lethal to cells depending on which ATP biosynthetic pathway that is operative in the cell (i.e., OXPHOS versus glycolysis), e.g., metabolic state-dependent lethality. Some of the compounds identified may induce a switch in cellular metabolism—either from aerobic glycolysis to mitochondrial OXPHOS or vice versa.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, In some embodiments, a general library of small molecules is screened, e.g., using the methods described herein.

In some embodiments, a test compound is applied to a test sample, e.g., a cell or living tissue or organ, and one or more effects of the test compound is evaluated. In a cultured or primary cell for example, the ability of the test compound to modulate mitochondrial respiration is evaluated.

In some embodiments, the test sample is, or is derived from (e.g., a sample taken from) an in vivo model of a disorder as described herein. For example, an animal model, e.g., a rodent such as a mouse or rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern Genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on mitochondrial metabolism.

A test compound that has been screened by a method described herein and determined to modulate mitochondrial respiration can be considered a candidate compound. A candidate compound that has been screened, e.g., in an in vivo model of a disorder, e.g., a disorder associated with altered mitochondrial respiration or function as described herein, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that modulate mitochondrial respiration) in a first screen can be selected and systematically altered, e.g., using rational design, to optimize binding affinity, avidity, specificity, or other parameter. Such optimization can also be screened for using the methods described herein. Thus, In some embodiments, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with altered mitochondrial respiration or function, e.g., as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with altered mitochondrial respiration or function as described herein. The animal can be monitored for a change in the disorder, e.g., for an improvement in a parameter of the disorder, e.g., a parameter related to clinical outcome.

Modulators of Mitochondrial Metabolism

The compositions and methods described herein include compounds that are modulators of mitochondrial metabolism as described herein. In some embodiments, the compound is an OXPHOS inhibitor. In some embodiments, the compound is a glycolysis inhibitor. In some embodiments, the compound is meclizine or an enantiomer or analog thereof, or a pharmaceutically acceptable salt thereof, e.g., meclizine hydrochloride, or S-meclizine hydrochloride. In some embodiments, the compound is another inhibitor of OXPHOS as described herein, e.g., identified in a screen as described herein, e.g., the drugs listed in Table 1. In some embodiments, the compound is an anti-histamine, a diphenypiperazine, a diphenylalkyl (alkoxyl)-based, or a tricyclic ring structure.

As described herein, a library of 3695 compounds comprising two commercially available compound collections that include nearly half of the FDA-approved drugs and other numerous bioactive and natural products was screened using one method of present invention. This library was then screened blindly with the aim of ascertaining which structural class or chemotypes were effective as cytoprotective agents, i.e., protecting against mitochondrial oxidative phosphorylation.

In the initial screen, an $S_{glu/gal}$ score, which is the log fold-change of normalized cell number in glucose versus normalized cell in galactose, was used to differentiate the compounds' ability to redirect cellular metabolic reliance from OXPHOS to glycolysis. Compounds that are selectively lethal or growth inhibitory in galactose will have a high $S_{glu/gal}$ score and are likely to include inhibitors of OXPHOS.

About 90% of the compounds didn't significantly affect cell viability and proliferation in glucose after treatment (with an average FcGlu value ≥0.8). Among them, about 124 compounds exhibited a high $S_{glu/gal}$ score of ≥0.08, potentially as the result of selective inhibition of cell growth in galactose. This included 25 FDA approved drugs (See Table 1). For example, screened clinically used drugs that were identified to selectively retard cell growth in galactose, and therefore are suspected OXPHOS inhibitors include, but are not limited to: alpha-toxicarol, benzethonium chloride, antimycin A, beta-dihydrorotenone, beta-toxicarol, totarol-19-carboxylic acid, methyl benzethonium chloride, isorotenone, deguelin, mundoserone, berberine chloride, mundulone, nonoxynol-9, alexidine dihydrochloride, dequalinium dichloride, clofilium tosylate, thonzonium bromide, psoromic acid, nifuroxazide, rotenonic acid methyl ether, rotenonic acid, pyrvinium pamoate, papaverine hydrochloride, pararosaniline pamoate, ethaverine hydrochloride, menadione, triptophenolide, diffratic acid, isogedunin, phenformin hydrochloride, sappanone a trimethyl ether, pentamidine isethionate, niloticin, vinpocetine, clomiphene citrate, aminopterin, mefloquine, thiostrepton, naftifine hydrochloride, chlorprothixene hydrochloride, clemastine fumarate, sertaconazole nitrate, palmatine chloride, florfenicol, pimozide, dequalinium chloride, deoxysappanone b trimethyl ether, bisacodyl, merbromin, coralyne chloride hydrate, artemisinin, dihydrorotenone, 3-deshydroxysappanol trimethyl ether, dorzolamide hydrochloride, rotenone, chlorhexidine, clofoctol, palmatine chloride, meclizine hydrochloride, fluvastatin sodium salt, and ascorbic acid. More specific analysis was conducted on 16 of those approved drugs, selected for a lack of previously reported activity on energy metabolism.

Structural inspection and SAR (structure-activity relationship) analysis of the entire library suggested that the formula A may represent a structural class that is capable of selectively inhibiting cell growth in galactose versus in glucose.

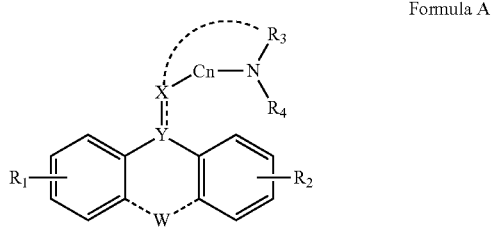

Formula A

Therefore, Formula A may give rise to therapeutically useful agent to protect cell death by blunting mitochondrial OXPHOS and redirecting cell's energy metabolism to glycolysis thus to minimize oxidative damage and suppress apoptosis.

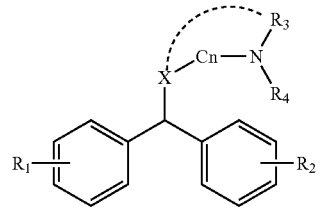

Subclass I

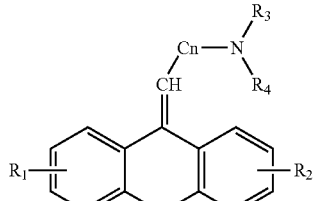

Subclass II

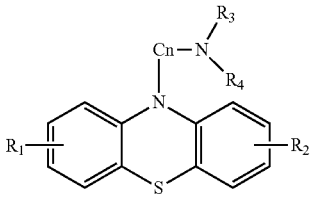

Subclass III

Formula A comprises at least three subclasses (I-III). For example, meclizine is structurally related to Formula A. It represents, in particular, Subclass I.

Briefly, molecules predicted by Formula A comprise a lipophilic aromatic moiety, a basic amino group (—NR3R4) and a linker —XCn-, wherein R3 and R4 are independently selected from a diverse groups including, but not limited to, H, C1-6alkyl, 3-hydroxyethoxyethyl, phenylallyl, C1-4-alkylenephenyl, benzyl and 3-methylbenzyl, 4-terbutylbenzyl. In addition, —NR3R4 together form cycloamino, such as piperidinyl derivative (e.g. Cloperastine) or piperazine derivatives (e.g. thiethylperazine). The linker is represented by a formula of —X(CH2)n-. The value for n is an integer of from 1 to 3. X is absent in Subclass III, while X could be N or O for Subclass I and CH for Subclass II. The lipophilic moiety of Subclass I comprises two aromatic phenyl rings linked by a —CH— (Y is CH) to form benzhydryl derivatives, whereas in Subclass II, two phenyl rings are linked by an alkenyl (YX is C=C) and a sulfur atom (W is —S—) or ethylene (W is —CH2-CH2-) to form a tricyclic moiety. In Subclass III, the lipophilic moiety phenothiazine (Y is —N—) and X is absent.

Figure 26:
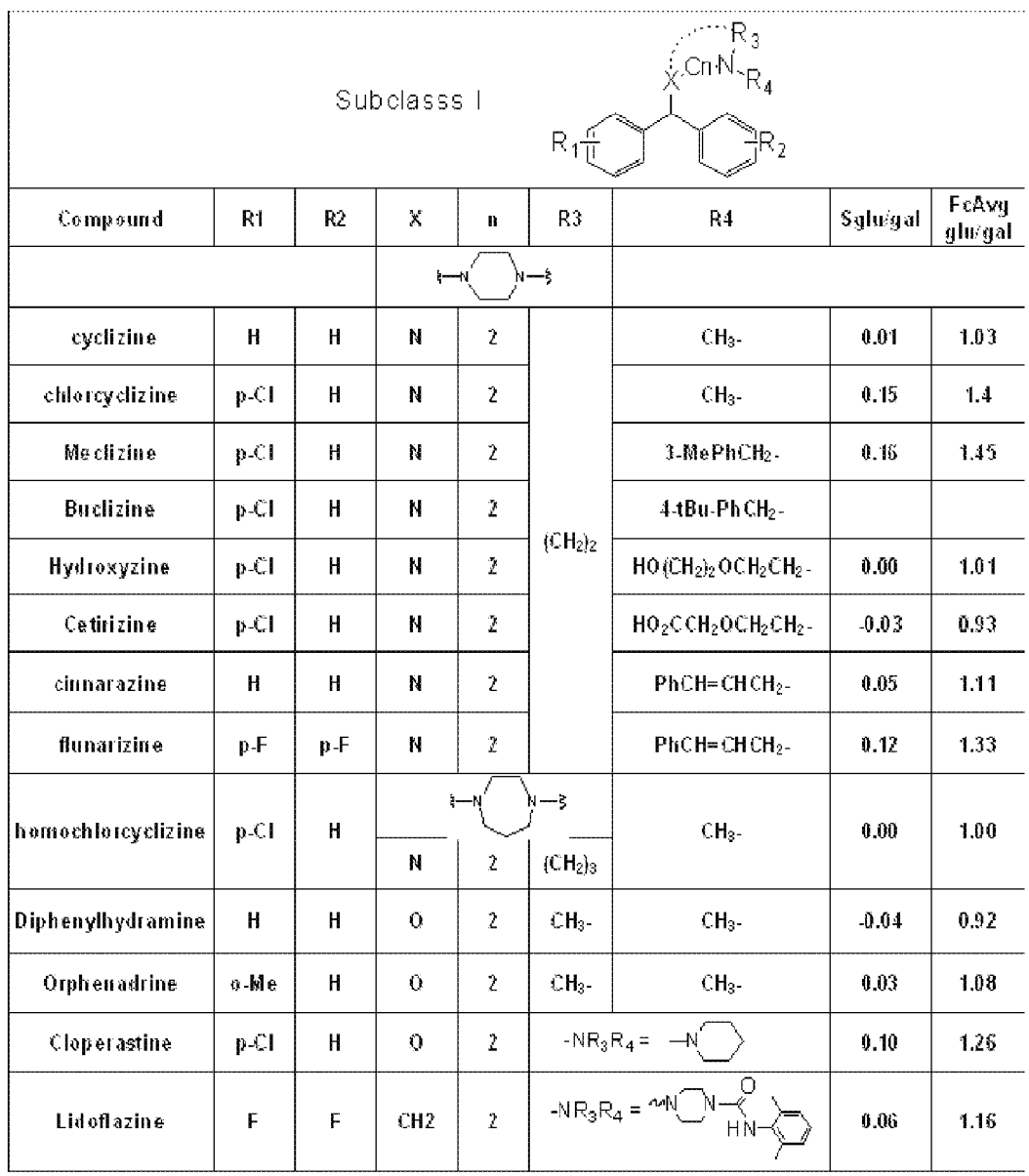
FIG. 26 presents exemplary representative compounds of Subclass I benzhydrylamine derivative structures.

SAR analysis of Subclass I revealed that substitution at phenyl ring of benzyhydryl with halogen, such as Cl or F, in particular at para position, results in more potent compounds. See FIG. 26. When benzhydryl moiety is attached to a nitrogen (X=N), together with nitrogen of —NR3R4, two nitrogen atoms could be cyclized through R3 to piperazine or homopiperazine derivatives, herein $R_3$ is a C2-3alkylene. The inhibitory activity of benzhydrylpiperazine derivative (e.g chlorcyclizine) is more potent than that of homopiperazine analogue (e.g homocyclizine). Although it is not necessary to understand the mechanism of an invention, it is believed that compounds with a lipophilic amino group are more active than those with a hydrophilic amino group, such as hydroxyzine and cetirizine. The methylene carbon of benzhydryl moiety could be a chiral center when $R_1$ is not equal to $R_2$. As a result, the compound could be a racemic mixture or an enantiomer with either R or S configuration.

Figure 27A:
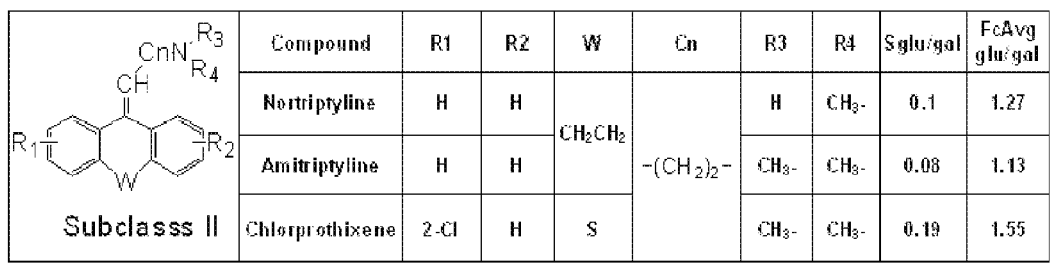
FIG. 27A presents exemplary representative compounds of Subclass II tricyclic structures.

For Subclass II, tricyclic derivatives comprising an ethylene (W is —CH2CH2-) in the middle ring (e.g., nortriptyline or amitriptyline) exhibit moderate inhibitory activity against cell growth in galactose, while activity could be improved when W is a sulfur atom to give thioxanthene derivative (e.g. chlorprothixene). Additionally, substitution on aromatic ring with Cl is well tolerated. See FIG. 27A.

Subclass III is mainly phenothiazine derivatives, in which the linker Cn could be a straight or branched alkylene group and the linker length is about 2-3 carbon atoms (n=2-3). Thiethylperazine having ethylthiyl substituent is more active than flufenazine, which has a trifluorormethyl substituent at the same position of phenothiazine core. See FIG. 27B.

Figure 28:
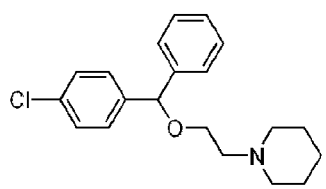
FIG. 28 presents exemplary representative compounds of an antihistamine structure.
Figure 28:
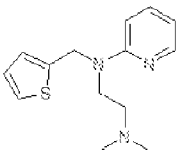
Figure 28:
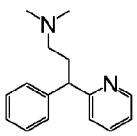
Figure 28:
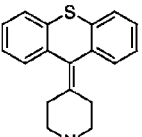
Figure 28:
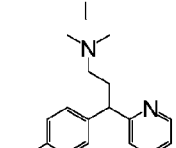
Figure 28:
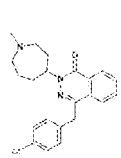
Figure 28:
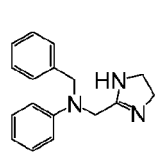
Figure 28:
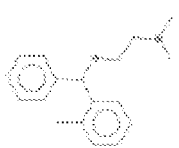
Figure 28:
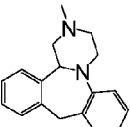
Figure 28:
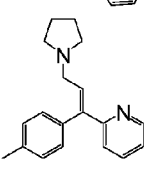
Figure 28:
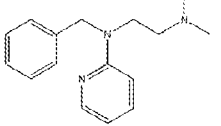
Figure 28:
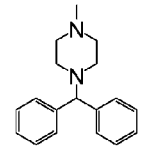
Figure 28:
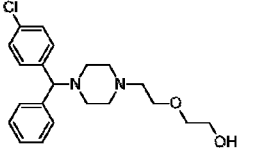
Figure 28:
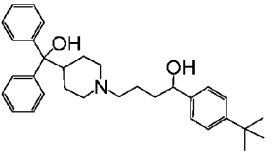
Figure 28:
Figure 28:
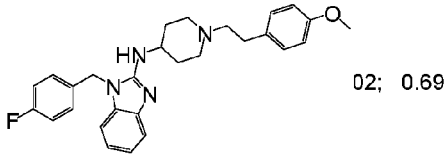
Figure 28:
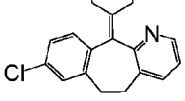
Figure 28:
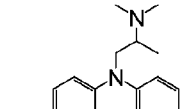
Figure 28:
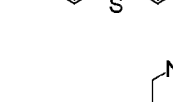
Figure 28:
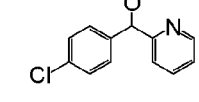
Figure 28:
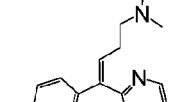
Figure 28:
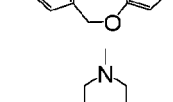
Figure 28:
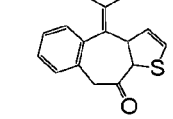
Figure 28:
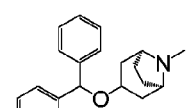
Figure 28:
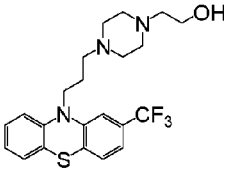
Figure 28:
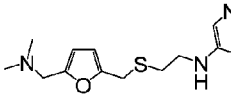
Figure 28:
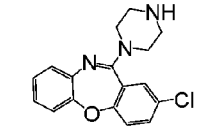
Figure 28:
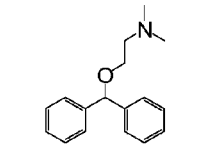
Figure 28:
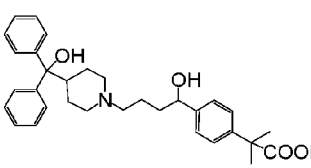
Figure 28:
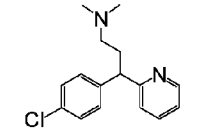
Figure 28:
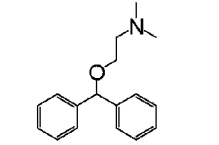
Figure 28:
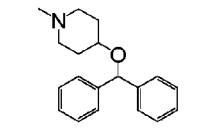
Figure 28:
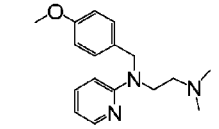

Other antihistamines identified by the methods described in the present invention are provided, wherein at least some have structures represented by those including, but not limited to Subclass I, Subclass II, or Subclass III. In some embodiments, the antihistamine-based structure comprises a compound selected including, but not limited to, those listed in FIG. 28.

Benzhydrylamine-Based Structures

In some embodiments, the present invention contemplates a composition comprising an benzhydrylamine-based structure. In some embodiments, the Benzhydrylamine-based structure comprises a Substructure A1 (diphenylpiperazine) or A2, e.g., a compound shown in FIG. 29. In some embodiments, the diphenylpiperazine-based structure comprises meclizine.

In some embodiments, the diphenylpiperazine-based structure comprises a compound including, but not limited to, those listed in FIG. 29.

Substructure A

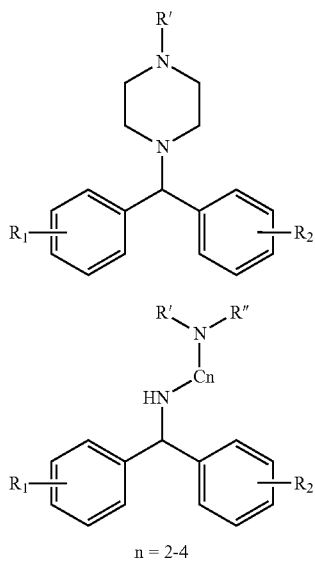

n = 2-4

Diphenylalkyl-Based Structures

Figure 30:
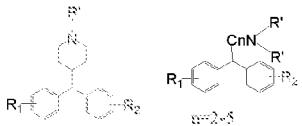
FIG. 30 presents exemplary representative compounds of a diphenylalkyl structure.
Figure 30:
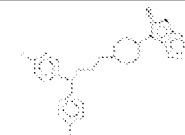
Figure 30:
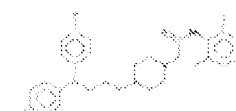
Figure 30:
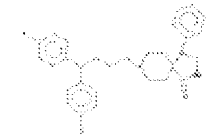
Figure 30:
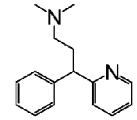
Figure 30:
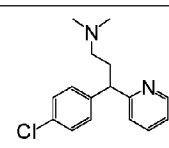
Figure 30:
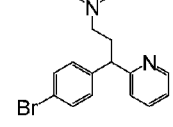
Figure 30:
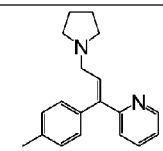
Figure 30:
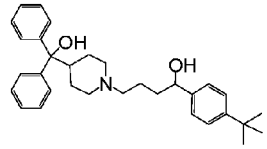
Figure 30:
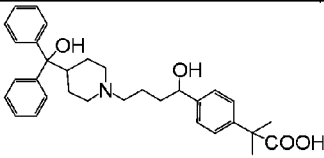
Figure 30:
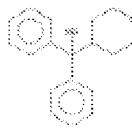
Figure 30:
Figure 30:

In some embodiments, the present invention contemplates a composition comprising an diphenylalkyl-based structure. In some embodiments, the diphenylalkyl-based structure comprises pimozide. In some embodiments, the diphenylalkyl-based structure comprises a compound including, but not limited to, those listed in FIG. 30.

Diphenylalkoxyl-Based Structures

Figure 31:
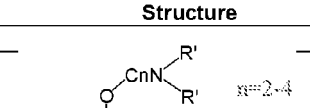
FIG. 31 presents exemplary representative compounds of diphenyl(alkoxyl) structure.
Figure 31:
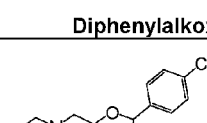

In some embodiments, the present invention contemplates a composition comprising an diphenylalkoxyl-based structure. In some embodiments, the diphenylpiperazine-based structure comprises cloperastine. In some embodiments, the diphenylalkoxyl-based structure comprises a compound including, but not limited to, those listed in FIG. 31.

Tricyclic Ring-Based Structures

In some embodiments, the present invention contemplates a composition comprising a tricyclic ring-based structure. In some embodiments, the tricyclic ring-based structure comprises Substructure E1 or E2, e.g., compounds 1 or 2 shown in FIG. 32.

Substructure E

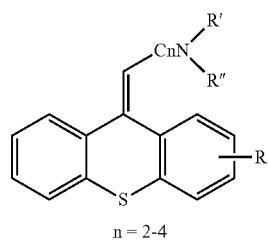

n = 2-4

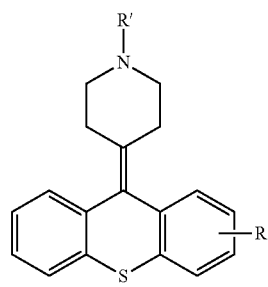

In some embodiments, the tricyclic ring-based structure comprises Substructure F1 or F2, e.g., compounds 3-5 shown in FIG. 32.

Substructure F

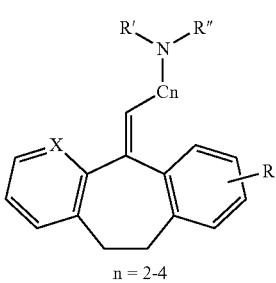

n = 2-4

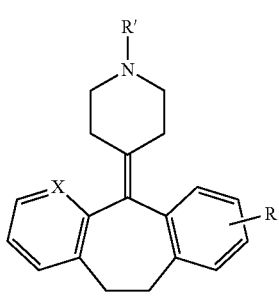

In some embodiments, the tricyclic ring-based structure comprises Substructure G1. In some embodiments, the tricyclic ring-based structure comprises Substructure G2, e.g., compounds 7-10 as shown in FIG. 32.

Substructure G

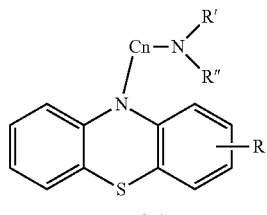

n = 2-4

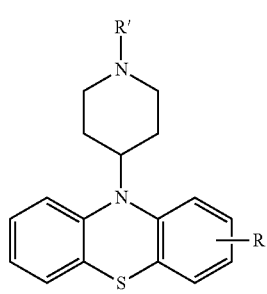

In some embodiments, the tricyclic ring-based structure comprises thiethylperazine. In some embodiments, the tricyclic ring-based structure comprises a compound including, but not limited to, those listed in FIG. 32.

Meclizine

Meclizine has been used for decades in humans for nausea and vertigo, is well tolerated, with the primary side effect being drowsiness. Food And Drug Administration, Federal Register 52:15866 (1987); and F. P. P. Jerrold B. Leikin, Poisoning and Toxicology Handbook (Tnforma Health Care, 2008), pp. 1331.

Meclizine hydrochloride is presently sold under the following commercial names: DRAMAMINE II®; DRAMAMINE LESS DROWSY®; ANTIVERT®; BONINE®; BONAMINE®; BONIKRAFT®; EMETOSTOP®; MEDIVERT®; SEA-LEGS®; AGYRAX®; and POSTAFEN® (SWEDEN).

The data presented herein demonstrates that even low micromolar concentrations of meclizine can induce significant shifts in energy metabolism and neuroprotection against polyQ toxicity, and is cytoprotective in cellular and animal models of heart attack/cardiac ischemic injury, stroke, renal ischemic injury, and diabetes. Also, the data presented herein demonstrate that the S-enantiomer of meclizine ("S-meclizine") does not bind to the $H_1$ receptor with high affinity and is thus not expected to have the side effects of drowsiness and/or sedation.

1. Oxidative Injury

Human SH-SY5Y neuroblastoma cells were previously used to screen for drugs that protect against oxidative injury, see Sarang, Physiol. Genomics, 11:45-52, 2002. Oxidative injury is a pathological factor in many neurodegenerative diseases. Sarang identified 26 drugs as providing neuroprotection; of those, six were examined in detail, including meclizine. The Sarang reference provided genomic profiling data showing that the mechanism of meclizine's oxidative protective effect may be due to an upregulation of the neuropeptide, galanin. The reference does not teach comparing cell growth between glucose and galactose media to identify non-toxic inhibitors of oxidative phosphorylation (i.e., compounds having an $S_{glu/gal}$ score between 0-1.00) as neuroprotective agents.

A cell-based bioassay for screening drug compounds for protecting against oxidative stress in diabetic neuropathy was reported in Vincent et al., Antioxidants & Redox Signaling, 10(2):387-393, 2008. Twenty-five out of 1,040 compounds screened decreased both mitochondrial superoxide and subsequent neuronal injury. A list of potential neuroprotective compounds provided by Vincent et al. included meclizine hydrochloride. Vincent et al. did not teach comparing cell growth between glucose versus galactose media to identify non-toxic inhibitors of either oxidative phosphorylation or glycolysis.

2. Mitochondrial Toxicity

A cell-based assay for screening drugs for mitochondrial toxicity was reported in Marroquin et al., Tox. Sciences, 97(2):539-547, (2007). The reference compares cell growth between cells grown in glucose versus galactose. The results showed that cells grown in galactose were more sensitive (lower $LD_{50}$) to the toxic effects of oxidative phosphorylation inhibitors than cells grown in glucose. Use of glucose versus galactose media, therefore, differentiated between mitochondrial dysfunction and provided a comprehensive toxicity screen. The reference does not teach the calculation of a glucose/galactose cell growth ratio to identify non-toxic inhibitors of either oxidative phosphorylation or glycolysis.

Enantiomers of Meclizine

The methods described herein can include the use of an enantiomerically pure form of meclizine, e.g., S-meclizine. As described herein, S-meclizine retains the ability to shift mitochondrial metabolism that is present in the racemate, but lacks the ability to bind the H1 receptor, and therefore is expected to substantially lack the side effects associated with activation of the histamine system. Thus S-meclizine or a pharmaceutically acceptable salt thereof, e.g., S-meclizine hydrochloride, can be used in the methods described herein.

S-meclizine can be obtained using methods known in the art. The following is an exemplary scheme for synthesising a substantially pure composition of S-mec.

Scheme 1

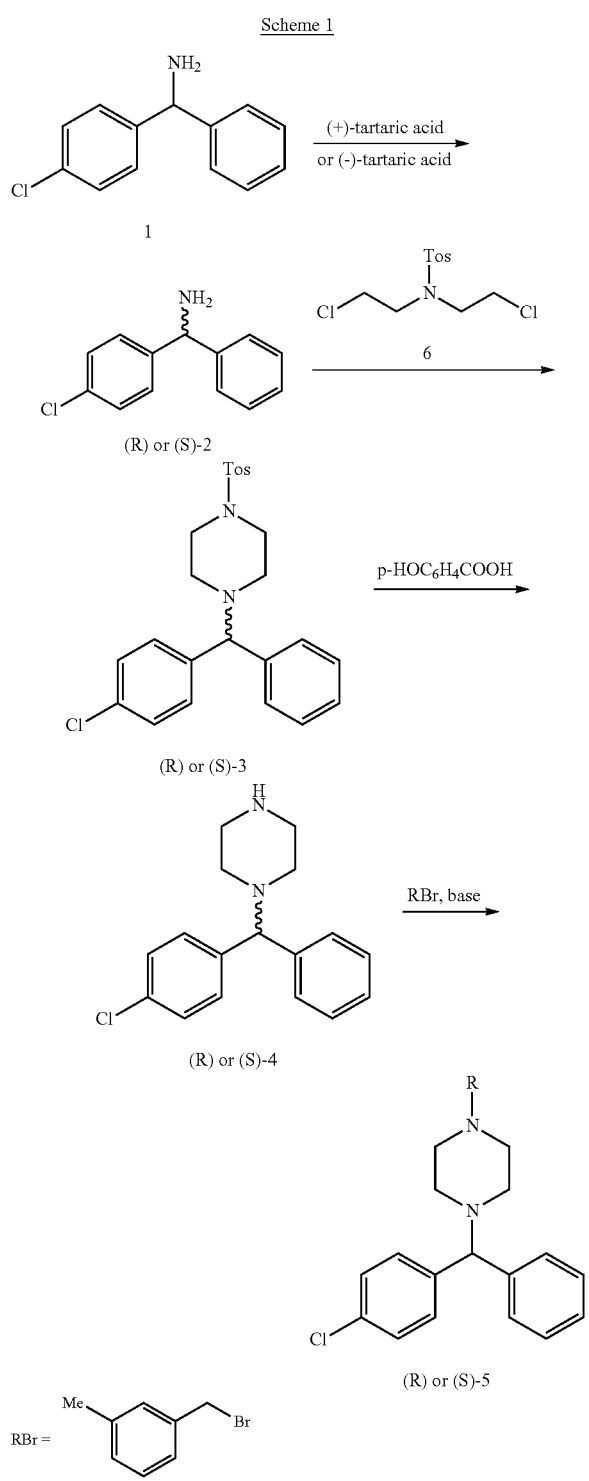

The (R) and (S) enantiomers of Meclizine were synthesized as shown in Scheme 1. The racemic 4-chlorobenzhydrylamine was treated with either D-tartaric acid or L-tartaric acid. The obtained salt was fractional recrystallization from water to provide the >98% pure enantiomers. The separated enantiomers were then individually treated with the bisalkylating agent 6 to provide the piperazine ring in 3. The tosyl group was deprotected with p-hydroxylbenzoic acid in HBr-acetic acid to provide the free amine. Treatment of the free amine with the 3-methylbenzyl bromide in refluxing methanol provided the enantiomerically pure (R) and (S)-Meclizines.

Other methods could also be used; for example one could resolve meclizine itself (the racemate) into its enantiomers rather than resolving the compound 1 in the scheme above, e.g., by resolution with a chiral acid such as tartaric acid. One could use a different chiral acid other (e.g., lactic acid or chiral camphorsulfonic acid) than tartaric acid. Alternatively, one could treat a chiral benzhydryl alcohol (will look similar to compound 1 but with a OH in place of NH2), convert it into a mesylate and then react it with piperazine to obtain the compound 4.

Smilkstein (U.S. Pat. App. Pub. No. US 200810194652 A1) (herein incorporated by reference) describes a method of using inactive isomer compositions as drug resistance-reversal agents and in prophylactic treatment includes the steps of selecting an antihistaminically-inactive isomer of a preselected antihistamine, and making stereoselective use of the antihistaminically-inactive isomer for preventing and treating malaria. This reports suggests that while the antihistaminic and sedative activity of most antihistamines result from the same enantiomer, including such drugs such as chlorphenirame (e.g., the (+) isomer. However, this report identifies that the (−) chlorpheniramine isomer improves drug-resistance to some anti-malarial drugs. The reference identifies meclizine as a stereoisomeric antihistamine but fails to identify an antihistaminic inactive enantiomer. Consequently, it does not suggest to one having ordinary skill in the art that meclizine has at least two enantiomers comprising differential biological activity. Other classes of drugs were reported to show in vitro drug resistance-reversal effects of antimalarial agents such as ricyclic antidepressants and phenothiazine antipsychotics. However, no data showing any specific differences in enantiomeric activity for these additional drug classes were discussed. As a result, the disclosure explicitly suggests that an enantiomer-specific action of antihistamines would be successful for chlorpheniramine.

It is believed that one having ordinary skill in the art (e.g., a medicinal chemist) would not consider a single antihistamine enantiomer lacking antihistaminic activity (e.g., not meclizine), to suggest that all R and S enantiomers behave differently. As is true in the chemical arts, such generalizations are unpredictable and rely upon empirical data (i.e., such as that presented herein). Moreover, before this invention there were no reports regarding analysis of the activity of meclizine R or S enantiomers. Therefore, a priori, it is not obvious, even if the respective enantiomers do have different activities, which one will be R or S and/or which one will be active or inactive. It is not obvious that both enantiomers would shift energy metabolism and protect against ischemic or degenerative disease; as noted herein, both enantiomers are active in the metabolic assays, yet only one (the R enantiomer) is active as an anti-histamine. It is further believed that an enantiomeric effectiveness in a parasite disease (e.g., malaria) does not suggest effectiveness in other diseases including, but not limited to, neurodegenerative disorders, ischemic disorders, and type 2 diabetes).

Meclizine was selected as a preferred compound for use in some of the methods and compositions described herein due to its favorable safety profile, high blood-brain barrier penetration and structural features.

Kits

In some embodiments, the present invention contemplates kits for the practice of the methods of this invention. The kits preferably include one or more containers containing reagents for an candidate compound screening method of this invention. The kit may optionally include a solid substrate comprising a cell culture matrix. The kit may optionally include one or more containers containing a plurality of carbon sources. The kit may optionally include a cell culture. The kit may optionally include a set of instructions explaining how to identify a candidate compound as a non-toxic modulator of mitochondrial energy metabolism. The kit may optionally include a solid substrate comprises a plurality of testing wells. The kit may optionally be frozen. The kit may optionally include sugar based carbon sources (e.g., glucose or galactose). The kit may optionally include a set of instructions provide for the determination of a cell growth ratio comparing the first carbon source with the second carbon source. The kits may also optionally include appropriate systems (e.g. opaque containers) or stabilizers (e.g. antioxidants) to prevent degradation of the reagents by light or other adverse conditions.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Pharmaceutical Formulations

The present invention further provides pharmaceutical compositions (e.g., comprising the small molecule or antisense compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which can conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

In some embodiments of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake at the cellular level may also be added to some of the pharmaceutical and other compositions described herein as appropriate. For example, cationic lipids, such as lipofectin (U.S. Pat. No. 5,705,188), cationic glycerol derivatives, and polycationic molecules, such as polylysine (WO 97/30731), enhance cellular uptake.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agent(s) of the formulation. As one example, the methods and compositions described herein can include the co-administration of an acetylated or non-acetylated salicylate, e.g., acetylsalicylic acid or salsalate. For example, in embodiments in which a daily dose of meclizine is administered, a daily dose of about 81 mg acetylsalicylic acid can also be administered. Thus the composition can be formulated for daily administration to deliver a dose of meclizine, e.g., S-meclizine, plus acetylsalicylic acid, in a single dosage form, e.g., an oral dosage form such as a pill or tablet.

Dosing can be dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In some embodiments, the dosage is from about 250 to 1000 mg/day, and may be given once or more daily, weekly, monthly or yearly. The treating physician can estimate repetition rates for dosing based on measured residence times and concentrations of the drug in bodily fluids or tissues; in some embodiments, the dosage is sufficient to achieve a concentration of about 100 nM-1 µM in the plasma of the subject. It may also be desirable to have the subject undergo maintenance therapy to prevent the recurrence of the disease state, wherein the meclizine is administered in maintenance doses, ranging from 0.01 µg to 100 µg per kg of body weight, once or more daily, to once every 20 years.

EXAMPLES

The invention is further described in the following examples, which do not limit the scope of the invention described in the claims.

Example 1

Cell Growth Assay

This Example describes the use of a growth assay capable of screening for inhibitors of the oxidative phosphorylation (OXPHOS) pathway. The assay included monitoring or measuring cell growth in cells that are grown in glucose (which allows the cell to utilize glycolysis) or in galactose (which switches the cell energy production from glycolysis to the OXPHOS pathway). To identify selective OXPHOS pathway modulators, a library of small molecules was screened for compounds and/or agents that selectively influence cell number in galactose but not in glucose. In some embodiments, the differential growth/survival of cells in glucose versus galactose is used as a screening method to identify small molecules that inhibit the OXPHOS pathway. In demonstrating proof of principle, the present inventors successfully screened at least 3695 clinically used drugs and bioactives, and identified some as OXPHOS inhibitors, a heretofore unknown use.

In these experiments, immortalized MCH58 human diploid fibroblasts containing pLKO.1 vector were grown in DMEM High glucose medium (Invitrogen Cat No. 11995) with 10% FBS (Sigma Cat No. F6178), 1× penicillin, streptomycin and glutamine (Invitrogen Cat. No. 10378-016), 2 ul/ml puromycin and 50 ug/ml uridine at 37° C. and 5% CO2. The high glucose medium was replaced with 10 mM glucose or 10 mM galactose wherever indicated. All media contained 1 mM pyruvate and 4 mM glutamine. The murine striatal cells expressing wildtype (STHdhQ7/7) or mutant (STHdhQ111/111) huntingtin protein were grown in DMEM high glucose medium with 10% FBS (Sigma Cat No. 12306C) and 1× penicillin, streptomycin, glutamine, and 200 µg/ml G418 at 33° C. and 5% CO2 (1). MCH58 fibroblasts, HeLa and 293 cells were grown in DMEM high glucose medium with 10% FBS (Sigma Cat No. F6178) at 37° C. and 5% CO2.

Cellular oxygen consumption and extracellular acidification assays were performed as follows. Briefly, MCH58 fibroblasts were seeded in XF24-well cell culture microplates (Seahorse Bioscience) at 30,000 cells/well in 10 mM glucose or 10 mM galactose media and incubated at 37° C./5% CO2 for ~20 hours. Prior to the measurements, the growth medium was replaced with ~925 µL of assay medium. The assay medium consisted of DMEM Base (Sigma Cat No D5030), 2 mM GlutaMax-1 (Gibco Cat No 350350-061), 1 mM Sodium Pyruvate (Sigma Cat No S8636), 10 mM Glucose (Sigma Cat No G8270) or Galactose (Sigma Cat No G5388), (1.85 g/L) Sodium Chloride and (15 mg/L) phenol red. The pH of the assay medium was adjusted to 7.4 with 1 N Sodium Hydroxide. The cells were incubated at 37° C. for 60 min in the assay medium prior to measurements.

The OCR and ECAR measurements on HeLa, 293, and STHdh$^{Q7/7}$ mouse striatal cells were carried out by growing them in XF24 plates at 40,000/well (HeLa) and STHdh$^{Q7/7}$ mouse striatal cells) and 60,000/well (293 cells) for ~20 hours in their regular growth conditions. The assay medium was the same as above except that 25 mM glucose was used as the sugar source. The measurements were performed simultaneously every 7 minutes after a 2 minute mix and 2 minute wait period for MCH fibroblasts and every 6 minutes (with 2 minutes mix and 2 minute wait) for HeLa, 293, and STHdh$^{Q7/7}$ mouse striatal cells. Three baseline measurements were recorded prior to the addition of oligomycin (Biochemika 75352), Antimycin (Sigma A8674), roetnone (Sigma R8875), carbonyl cyanide 3-chlorophenylhydrazone (Sigma C2759) and meclizine hydrochloride (MSDiscovery 01500376). 50 mM stock solution of meclizine was made in DMSO, which was diluted to specified concentration in assay medium and its pH was adjusted to 7.4 by 1N Sodium hydroxide solution. The measurements were carried out at 33° C. for mouse striatal cells but for all other cell types measurement were done at 37° C.

Cell number quantification high throughput assays were performed as follows. MCH58 fibroblasts were seeded at 5000 cells/well using the robotic MultiDrop Combi (ThermoFisher Scientific) dispenser into 96-well plates (PerkinElmer 6005182) at 100 uL per well in DMEM High glucose media. Seeding was demonstrated to have coefficient of variance <10% (data not shown). 24 hours later, cells were washed twice in PBS and media was replaced with either 10 mM glucose or 10 mM galactose containing media.

Approximately 100 nL of each compound was pin-transferred in duplicate into the plates with a steel pin array using the CyBi-Well robot (CyBio). The compound collection of 3695 drugs is described previously (Wagner et al., *Nat Biotechnol* 26:343 (2008)) and includes two commerically available libraries (Spectrum and Prestwick). Compound-treated plates were incubated at 37° C. for 72 hours. Cells were then washed once with PBS, stained with 10 µM Hoechst 33342 (Invitrogen) and fixed in 3.7% formaldehyde solution for 15 minutes. Wells were then washed once and stored in PBS. Cell culture plates were stored at 4° C. until time of imaging, which was at most 24 hours after fixation.

Imaging was performed by Arrayscan VTi automated microscope (ThermoFisher Scientific) with the use of an automated plate stacker. Appropriate filter sets for the detection of the Hoescht fluorescent signal were used. Four non-overlapping images at 5× magnification (NA 0.25) were acquired for a field of view of 1.3 mm×1.3 mm per image. The plate stacker and microscope including an auto-focusing algorithm were controlled entirely with ArrayScan software. Images were captured and stored simultaneously in at least two independent locations. Image analysis was performed using the freely available open-source software package CellProfiler. Carpenter et al., *Genome Biol* 7:R100 (2006). Images were analyzed individually by first identifying nuclei using the Hoescht staining signal.

Total number of nuclei per field were recorded, and the four images per well were totaled to give the cell count per well. Computation was performed using a UNIX computer cluster.

Appropriate masking of each nucleus was ensured by visually monitoring each batch at its onset and intermittently throughout the run.

As a control, classic inhibitors of the electron transport chain (e.g., complex I inhibitor rotenone, complex III inhibitor antimycin, complex V inhibitor oligomycin, and uncoupler carboxyl cyanide m-chlorophen-yehyhydra zone (CCCP)) were tested in MCH58 fibroblasts grown in a glucose-rich media (i.e., herein glucose is the sole sugar source) and a galactose-rich media (i.e, wherein galactose is the sole sugar source). As expected, these classic metabolic inhibitors are toxic in all tested concentrations, but are much more potent when cells are grown in a galactose-rich media.

For example, the $LD_{50}$ for rotenone, antimycin, and oligomycin were at least four orders of magnitude lower in a galactose-rich media as compared to a glucose-rich media. Notably, the difference between $LD_{50}$ for CCCP in a glucose-rich media as compared to a galactose-rich media is more subtle, most likely because mitochondrial membrane potential is important for cell survival. Differential growth between glucose-rich media versus galactose-rich media has previously been used to diagnose human mitochondrial disorders as well as mitochondrial toxicity. Robinson et al., *Biochem Med Metab Biol.* 48:122 (1992); and Marroquin et al., *Toxicol Sci* 97:539 (2007). In a pre-screen developmental study, the sensitivity of fibroblasts to 'metabolic state-dependent lethality' was confirmed by comparing various reported OXPHOS poisons. See FIGS. 1E-1H. Because growth and survival was measured over a three-day period, the disclosed assay is very sensitive and is capable of identifying compounds with potentially subtle or novel mechanisms of action.

Figure 2A:
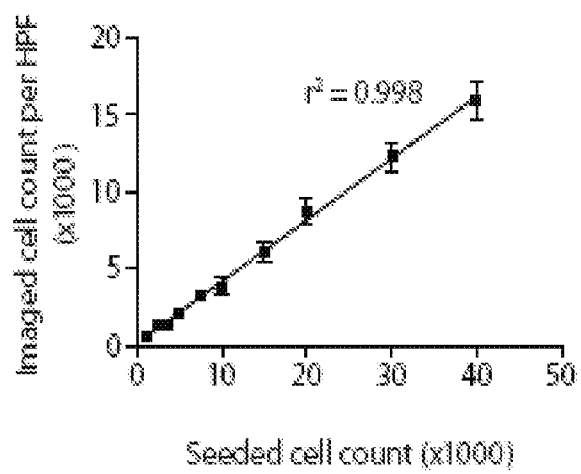
FIG. 2A presents one embodiment of a standardization curve for a high-throughput image-based cell counting technique. Cells were counted by hemocytometer, seeded into 96-well plates by robot, and counted again by the automated imaging method. Solid line represents linear regression with best-fit value shown. Data expressed as mean±SD (n=10).
Figure 2B:
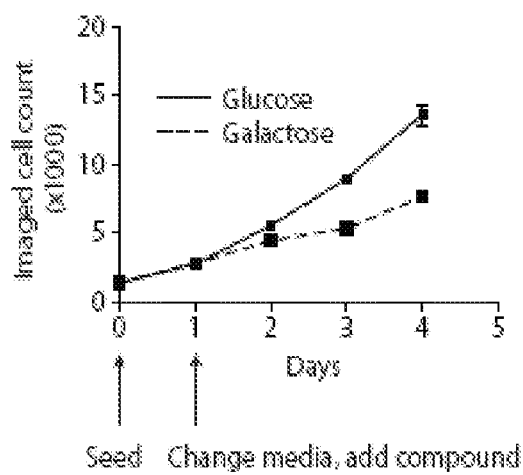
FIG. 2B presents exemplary data showing pre-screening data using an automated seeder, aspirator, fluid dispenser, and imaging method demonstrating high sensitivity to differences in cell number. Cells are seeded in 96-well plates in 25 mM glucose media on Day 0. On Day 1, cells are washed with PBS and their media is replaced with 10 mM glucose or 10 mM galactose, followed by the addition of a drug or dimethyl sulfoxide (DMSO). Data expressed as mean±SD (n=3).

A small molecule screening method as described herein, e.g., based on metabolic state-dependent mortality, can be scaled-up, e.g., using a microscopy-based high-throughput method of quantifying cell number with high reproducibility, e.g., by measuring the correlation between the numbers of cells seeded with the imaged nuclei count. See FIG. 2A. A typical cell growth profile of DMSO treated cells was measured by this high throughput assay in glucose and galactose. See FIG. 2B.

Figure 2C:
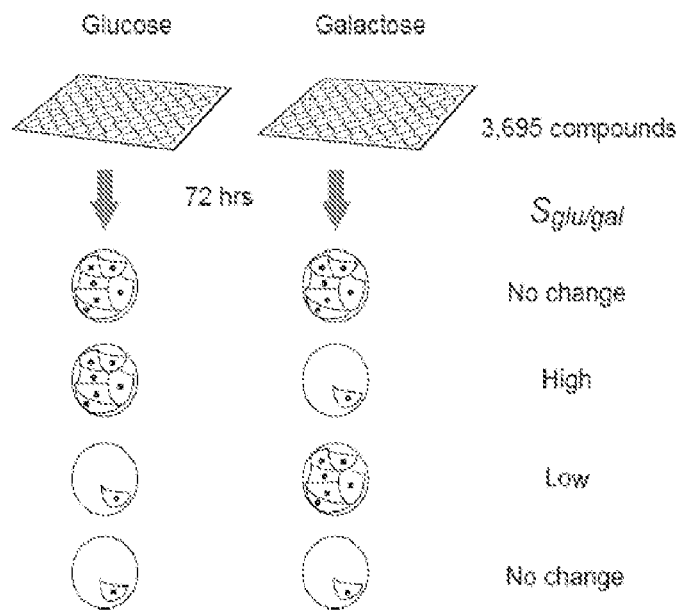
FIG. 2C presents schematic illustrations depicting a screening concept of cells grown in 96 well plates containing either glucose or galactose media that are exposed to a chemical library of test compounds. Analyzing the viability of cells in each well allows for categorization of each compound as non-toxic (no change), toxic (low cell number in both conditions), OXPHOS inhibitor (low cell numbers in Gal only, e.g., High Sglu/gal), or rapid proliferation inhibitor (low cell numbers in Glu only, e.g., Low Sglu/gal).

Next, data was generated to assess 'metabolic state-dependent sensitivity' in duplicate human fibroblast cultures grown in either glucose-rich media or galactose-rich media, by screening a chemical library of three thousand six hundred and ninety-five (3695) compounds. See FIG. 2C. In some embodiments, the chemical library comprises two commercially available compound collections that includes approximately one-half of FDA-approved drugs and other bioactive and natural products. The fibroblast cells were seeded on Day 0 and incubated for 24 hours in standard culture media. On Day 1, the media was changed to contain either glucose (e.g., duplicate 1) or galactose (i.e., duplicate 2) as the sole sugar source, followed by the addition of the compound to be screened at a concentration of approximately 10 µM. Following seventy-two hours of incubation with the compound to be screened, the wells were imaged, cell counts determined and normalized to DMSO control wells.

Cell viability was assayed by calcein acetoxymethyl (AM) ester assay (Invitrogen C34852). MCH58 cells were seeded in 96-well plates at 5000 cells/well in DMEM high glucose medium. After ~20 hours, cells were washed in PBS and the growth medium was replaced with 10 mM glucose or 10 mM galactose media containing different concentration of drugs or DMSO (0.1%). The cells were then grown for 72 hours followed by washing with PBS and addition of 5 µM calcein AM. After 30 minutes of incubation at 37° C., fluorescence was measured at an excitation and emission wavelength (ex/em) of 485 nm and 530 nm in a DTX880 multimode detector (Beckman Coulter).

Total cellular ATP level was measured using the CellTiter-Glo Luminescent Viability assay (Promega, G7571). Cells were grown in 96-well plates at 5000 cells/well for MCH58 and 20,000 cells/well for mouse striatal cells. Meclizine was added after 24 hours and ATP levels were measured after 72 hours for MCH58 cells and 24 hours for striatal cells as per the manufacturer's protocol.

Wherever indicated, mutant ($STHdh^{Q111/111}$) striatal cells were grown in serum free media for ~24 hours before ATP measurement. Luminescence was measured in DTX880 multimode detector. Multiple concentrations (between 100 µM and 0.5 µM) of rotenone, antimycin, oligomycin, meclizine, hydroxyzine (Spectrum chemical), thiethylperazine (Prestwick), cyproheptadine (Sigma), pyrilamine (Spectrum chemical), tripelennamine (Spectrum chemical), diphenhydramine (Spectrum chemical), clemastine (Prestwick), bromopheniramine (Spectrum chemical), pheniramine (Spectrum chemical), promethazine (MSDiscovery 01500510), atropine (Sigma), and scopolamine (Sigma) were tested for their protective effect on $STHdh^{Q111/111}$ cells in serum free media. The dose which conferred maximum protection is shown. Luminescence was measured in DTX880 multimode detector.

Normalized cell counts were computed separately for each 96-well plate by dividing the cell count of each well with the trimmed mean (the average after discarding the largest and smallest value) of the cell counts for the 16 DMSO treated wells. A single 96-well plate that exhibited very low counts in all wells and was discarded. Measurements were removed that failed to replicate by requiring that the ratio of normalized counts was less than 1.5 between replicates; this excluded 49 wells. The remaining replicate measurements were averaged, and fold changes were computed as the ratio between the average normalized counts for the glucose and galactose screens. To evaluate statistical significance, Z-scores were computed for each well against the DMSO (null) distribution and averaged Z-scores across replicates. Wells with average Z-score greater than 2.5 were considered significant.

By jointly analyzing the glucose and galactose results, a glucose-galactose cell growth ratio can be calculated ($S_{glu/gal}$) that represents the $\log_{10}$ fold-change in cell growth in a glucose rich media divided by the $\log_{10}$ fold-change in cell growth in a galactose rich media. Consequently, each screened drug may be described by its effects on cell number selectively comparing growth in glucose-rich media relative to galactose-rich media. As expected, the DMSO growth data in both glucose rich media and galactose rich media were equivalent, therefore the $S_{glu/gal}$ score centered on zero (e.g., ~0.0). Further, the majority of the screened compounds having no effect on cell number, some compounds leading to cell death relative to DMSO, and no compounds increasing cell numbers (data not shown). Drugs that are selectively lethal or growth inhibitory in galactose-rich media should have relatively higher $S_{glu/gal}$ scores (e.g., ranging between approximately 0.1 to 0.9) and are likely to include OXPHOS inhibitory compounds. Low $S_{glu/gal}$ scores (e.g., ranging between approximately (−) 0.1 to (−) 0.7) may arise from inhibition of glycolysis or from inhibition of proliferation, since cells grown in glucose-rich media divide more rapidly. See FIG. 2B. In some embodiments, compounds with an elevated $S_{glu/gal}$ (i.e., that selectively kill cells in a galactose-rich media) are likely to be oxidative metabolism inhibitors. Compounds with a low $S_{glu/gal}$ are those that inhibit rapid proliferation in glucose-rich conditions; these compounds may be useful as anticancer agents; as they are likely to be potent killers of rapidly dividing cells.

Figure 2D:
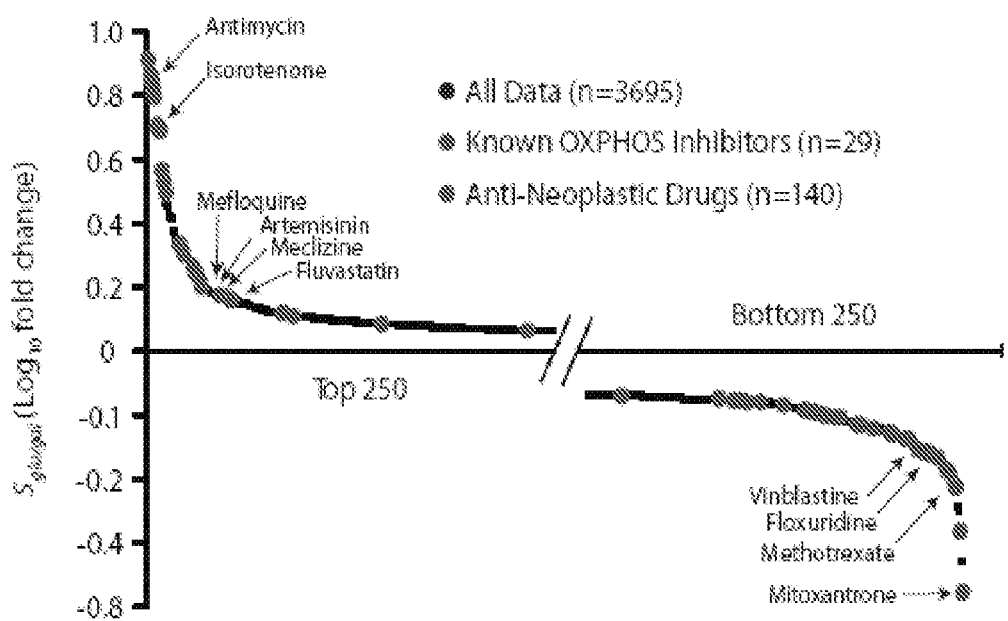
FIG. 2D presents exemplary data of a high through-put library screen of potential mitochondrial metabolic inhibitors and inhibitors of rapid cell proliferation. $Log_{10}$ of fold change in glucose divided by fold change in galactose for all drugs plotted in decreasing order. The distribution curve comprises the most effective OXPHOS inhibitors (i.e., $S_{glu/gal}>0.0$) and inhibitors of rapid cell proliferation (i.e., $S_{glu/gal}<0.0$).

The screened compounds were ranked based on $S_{glu/gal}$. Although it is not necessary to understand the mechanism of an invention, it is believed that drugs having a high $S_{glu/gal}$ may inhibit OXPHOS through a variety of mechanisms including, but not limited to, blocking electron transport at specific complexes, uncoupling respiration, and possibly altering the gene expression of OXPHOS subunits. As expected, the distribution of $S_{glu/gal}$ is centered on 0, with the majority of compounds exhibiting comparable normalized growth and viability in either glucose-rich media or galactose-rich media. See FIG. 2D. Nonetheless, the data show that the upper tail of the $S_{glu/gal}$ distribution is enriched with known respiratory chain poisons (e.g., OXPHOS inhibitors). See, Table 1. For example, the top twenty-five (25) scoring compounds include twenty (20) poisons previously reported to disrupt respiration by directly interrupting or uncoupling electron transport from ATP synthesis.

TABLE 1

Top Twenty-Five Compounds With Highest $S_{glu/gal}$ ($\log_{10}$ fold change) Score

| Rank | Compound | $S_{glu/gal}$ | Inhibition Mechanism |
|---|---|---|---|
| 1 | Alpha-toxicarol | 0.91 | Complex I inhibitor |
| 2 | Benzethonium chloride | 0.90 | Induces loss of Ψ |
| 3 | Antimycin A | 0.87 | Complex III inhibitor |
| 4 | Beta-dihydrorotenone | 0.85 | Complex I inhibitor |
| 5 | Beta-toxicarol | 0.82 | Complex I inhibitor |
| 6 | Totarol-19-carboxylic acid | 0.80 | Uncoupler |
| 7 | Methyl benzethonium chloride | 0.80 | Induces loss of Ψ |
| 8 | Isorotenone | 0.71 | Complex I inhibitor |
| 9 | Antimycin a | 0.70 | Complex III inhibitor |
| 10 | Deguelin(-) | 0.69 | Complex I inhibitor |
| 11 | Mundoserone | 0.57 | Complex I inhibitor |
| 12 | Benzethonium chloride | 0.54 | Induces loss of Ψ |
| 13 | Berberine chloride | 0.53 | Complex I inhibitor |
| 14 | Mundulone | 0.50 | Complex I inhibitor |
| 15 | Methylbenzethonium chloride | 0.46 | Induces loss of Ψ |
| 16 | Nonoxynol-9 | 0.46 | Unknown |
| 17 | Alexidine dihydrochloride | 0.44 | Induces loss of Ψ |
| 18 | Dequalinium dichloride | 0.42 | Complex I inhibitor |
| 19 | Clofilium tosylate | 0.42 | Unknown |
| 20 | Berberine chloride | 0.41 | Complex I inhibitor |
| 21 | Thonzonium bromide | 0.38 | Unknown |
| 22 | Psoromic acid | 0.35 | Unknown |
| 23 | Nifuroxazide | 0.34 | Unknown |
| 24 | Rotenonic acid, methyl ether | 0.34 | Complex I inhibitor |
| 25 | Rotenonic acid | 0.33 | Complex I inhibitor |

Further, the lower tail of the $S_{glu/gal}$ distribution is enriched with known anti-neoplastic compounds (e.g., drugs that are known to kill rapidly dividing cells). See FIG. 2D. For example, twenty-six (26) of the fifty (50) lowest $S_{glu/gal}$ scores correspond to known chemotherapeutic agents that are likely selectively toxic to cells rapidly proliferating in a glucose rich media. See, Table 2.

TABLE 2

Bottom Fifty Compounds With Lowest $S_{glu/gal}$ ($\log_{10}$ fold change) Score.

| Rank | Compound | $S_{glu/gal}$ | Drug Class |
|---|---|---|---|
| 1 | mitoxanthrone hydrochloride | −0.73 | Antineoplastic |
| 2 | tomatine | −0.64 | Antifungal |
| 3 | homidium bromide | −0.54 | Trypanocidal |
| 4 | andrographolide | −0.46 | Antineoplastic |
| 5 | pristimerol | −0.45 | Antineoplastic |
| 6 | Methotrexate; methotrexate | −0.39 | Antineoplastic |
| 7 | pristimerin | −0.37 | Antineoplastic |
| 8 | acrisorcin | −0.36 | Antifungal |
| 9 | crassin acetate | −0.35 | Antineoplastic |
| 10 | gambogic acid | −0.34 | Antineoplastic |
| 11 | parthenolide | −0.34 | Antineoplastic |
| 12 | cantharidin | −0.33 | Anti wart |
| 13 | aklavine hydrochloride | −0.33 | Antineoplastic |
| 14 | dihydrogambogic acid | −0.32 | Antineoplastic |
| 15 | nigericin sodium | −0.31 | Antimicrobial |
| 16 | dihydrocelastrol | −0.31 | Antineoplastic |
| 17 | anthothecol | −0.30 | Antimalarial |
| 18 | quinacrine hydrochloride | −0.30 | Antiprotozoal Antirheumatic |
| 19 | pyrromycin | −0.30 | Antineoplastic |
| 20 | celastrol | −0.29 | Antineoplastic |
| 21 | 15-norcaryophyllen-3-one | −0.29 | |
| 22 | acriflavinium hydrochloride | −0.29 | Antimicrobial |
| 23 | aminacrine | −0.29 | Anti-infective |
| 24 | phenylmercuric acetate | −0.29 | Antifungal |
| 25 | floxuridine | −0.28 | Antineoplastic |
| 26 | Podophyllotoxin | −0.27 | Antineoplastic |
| 27 | podofilox | −0.27 | Antineoplastic |
| 28 | vinblastine sulfate | −0.27 | Antineoplastic |
| 29 | methotrexate | −0.27 | Antineoplastic |
| 30 | Amethopterin | −0.26 | Antineoplastic |
| 31 | propachlor | −0.26 | Herbicide |
| 32 | Trifluridine | −0.26 | Antiviral |
| 33 | DMSO | −0.26 | |
| 34 | camptothecin | −0.26 | Antineoplastic |
| 35 | Colchicine | −0.26 | Antineoplastic |
| 36 | pyrithione zinc | −0.25 | Antibacterial |
| 37 | picropodophyllotoxin acetate | −0.24 | Antineoplastic |
| 38 | Parbendazole | −0.24 | Antihelminth |
| 39 | anisomycin | −0.24 | Antibiotic |
| 40 | chloroxine | −0.23 | Antibacterial |
| 41 | helenine | −0.22 | Antiviral |
| 42 | paclitaxel | −0.22 | Antineoplastic |
| 43 | 7-desacetoxy-6,7-dehydrogedunin | −0.22 | |
| 44 | crinamine | −0.22 | HIF-1alpha inhibitor |
| 45 | cedrelone | −0.22 | Antimicrobial |
| 46 | emetine | −0.22 | Protein synthesis inhibitor |
| 47 | thimerosal | −0.22 | Antiseptic |
| 48 | neriifolin | −0.21 | Antineoplastic |
| 49 | gitoxigenin diacetate | −0.21 | Antineoplastic |
| 50 | sarmentogenin | −0.21 | Antineoplastic |

Amongst the top eighty-three compounds having the highest $S_{glu/gal}$ scores (83; top 2% of the distribution), twenty-five (25) agents having FDA approval for clinical use were identified. See, Table 3. These compounds were observed to exhibit lower $S_{glu/gal}$ scores than classical OXPHOS inhibitors as used in the validation studies (supra).

TABLE 3

Top Twenty-Five Clinically Used Compounds Having High $S_{glu/gal}$
($\log_{10}$ fold change) Scores

| Rank | Compound | $S_{glu/gal}$ | Clinical Use | Effect On OXPHOS |
|---|---|---|---|---|
| 16 | Nonoxynol-9 | 0.46 | Topical spermicide | Unknown |
| 23 | Nifuroxazide | 0.34 | Antibiotic | Unknown |
| 27 | Papaverine hydrochloride | 0.30 | Vasodialator | Complex I Inhibitor |
| 34 | Phenformin hydrochloride | 0.27 | Hypoglycemic Agent | Complex I Inhibitor |
| 36 | Pentamidine isethionate | 0.24 | Trypanocidal | Unknown |
| 38 | Vinpocetine | 0.23 | Vasodilator | Unknown |
| 40 | Clomiphene citrate | 0.21 | Selective estrogen receptor modifier | Modulates Ψ |
| 42 | Mefloquine | 0.20 | Anti-malarial | Unknown |
| 45 | Naftifine hydrochloride | 0.19 | Topical anti-fungal | Unknown |
| 47 | Clemastine fumarate | 0.19 | Anti-histamine | Unknown |
| 48 | Sertaconazole nitrate | 0.19 | Topical anti-fungal | Unknown |
| 52 | Pimozide | 0.18 | Anti-psychotic | Complex V Inhibitor |
| 55 | Bisacodyl | 0.18 | Laxative | Unknown |
| 58 | Artemisinin | 0.17 | Anti-malarial | Induces loss of Ψ |
| 61 | Dorzolamide hydrochloride | 0.17 | Carbonic Anhydrase Inhibitor | Unknown |
| 63 | Chlorhexidine | 0.16 | Topical antiseptic | Unknown |
| 66 | Meclizine hydrochloride | 0.16 | Anti-emetic | Unknown |
| 67 | Fluvastatin sodium salt | 0.16 | HMG CoA-reductase inhibitor | Induces loss of Ψ |
| 68 | Ascorbic acid | 0.15 | Vitamin | Unknown |
| 69 | Niclosamide | 0.15 | Anti-nematodal | Uncoupler |
| 70 | Sertraline hydrochloride | 0.15 | Selective Serotonin Reuptake Inihibitor | Unkown |
| 71 | Thiethylperazine malate | 0.15 | Anti-emetic | Unkown |
| 72 | Carvedilol | 0.15 | Non-selective adrenergic blocker | Complex I inhibitor |
| 75 | Ethynodiol diacetate | 0.15 | Contraceptive | Unknown |
| 83 | Cyclobenzaprine hydrochloride | 0.13 | Muscle relaxant | Unknown |

It had been previously reported that nine of these twenty-five compounds (i.e., papaverine, phenformin, artemisinin, pentamidine, clomiphene, pimozide, niclosamide, fluvastatin, carvedilol) inhibited or uncoupled mitochondrial respiration. Interestingly, this list includes two anti-malarial drugs (e.g., artemisinin or mefloquine), consistent with reports that artemisinin requires respiration in the parasite for activity. Golenser et al., *Int J Parasitol* 36: 1427 (2006). The remaining sixteen clinically used agents span a broad range of clinical indications and diverse mechanisms of action. These drugs may be useful for treating diseases associated with modulations in energy metabolism.

Example 2

Evaluation of Meclizine Activity

To study the potential therapeutic benefit for neurodegenerative diseases of screened candidate drugs identified in Table 3, an agent having a favorable therapeutic index and ability to cross the blood brain barrier was desired. Meclizine (Rank #66), was selected as a representative test compound. Meclizine exhibits a favorable toxicity profile in humans and acts as an anti-emetic and anti-vertigo agent. Further, meclizine is available over the counter and is believed to have good central nervous system penetration. Food And Drug Administration, *Federal Register* 52:15866 (1987); and In: *Canada Gazette* Vol. 134 (2000).

Figure 3A:
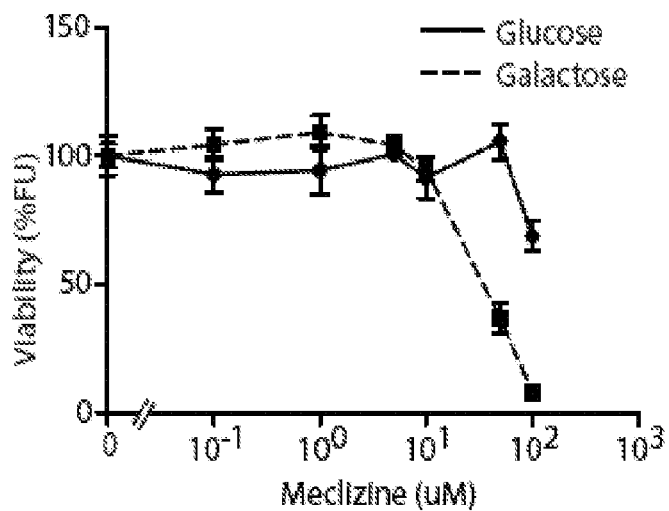
FIG. 3A presents exemplary data showing cell viability (Calcein AM® dye) at range of meclizine concentrations on MCH58 cells after three (3) days of incubation. Solid line: Glucose rich media. Dashed line: Galactose rich media. Data expressed as mean+/−SD (n=5).
Figure 3B:
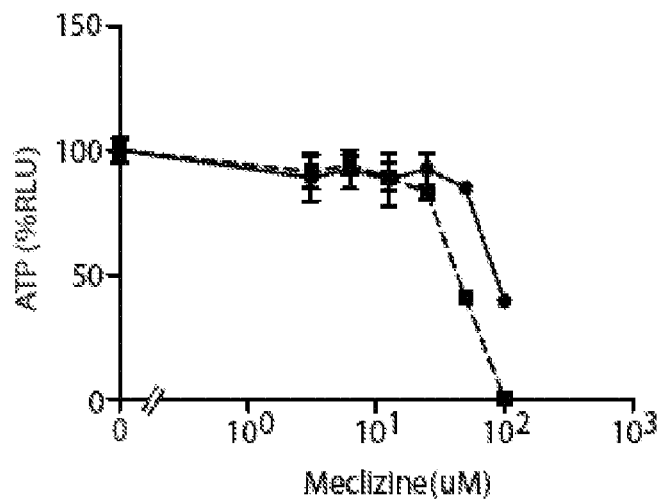
FIG. 3B presents exemplary data showing cellular ATP levels (CellTiter-Glo®) at range of meclizine concentrations in MCH58 cells after three (3) days of incubation. Solid line: Glucose rich media. Dashed line: Galactose rich media. Data expressed as mean+/−SD (n=5).
Figure 3C:
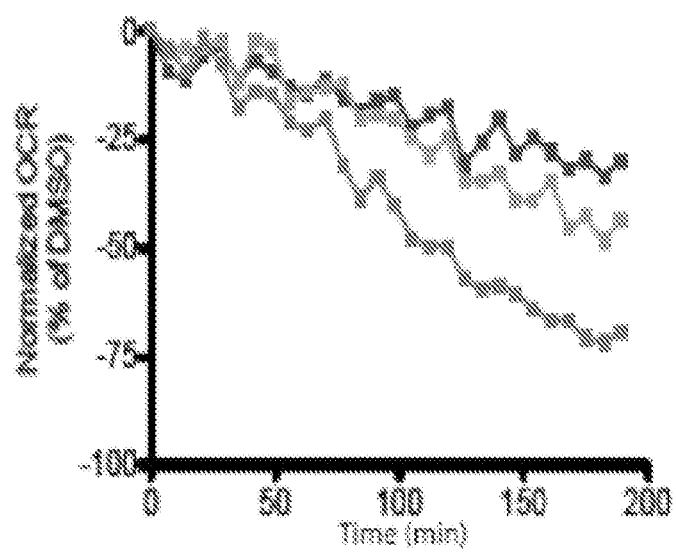
FIG. 3C presents exemplary data showing changes in OCR from a DMSO baseline in MCH58 cells exposed to different concentration of meclizine over a three hour timeframe. Measurements are taken every seven minutes. Average of 5 replicates are shown.
Figure 3D:
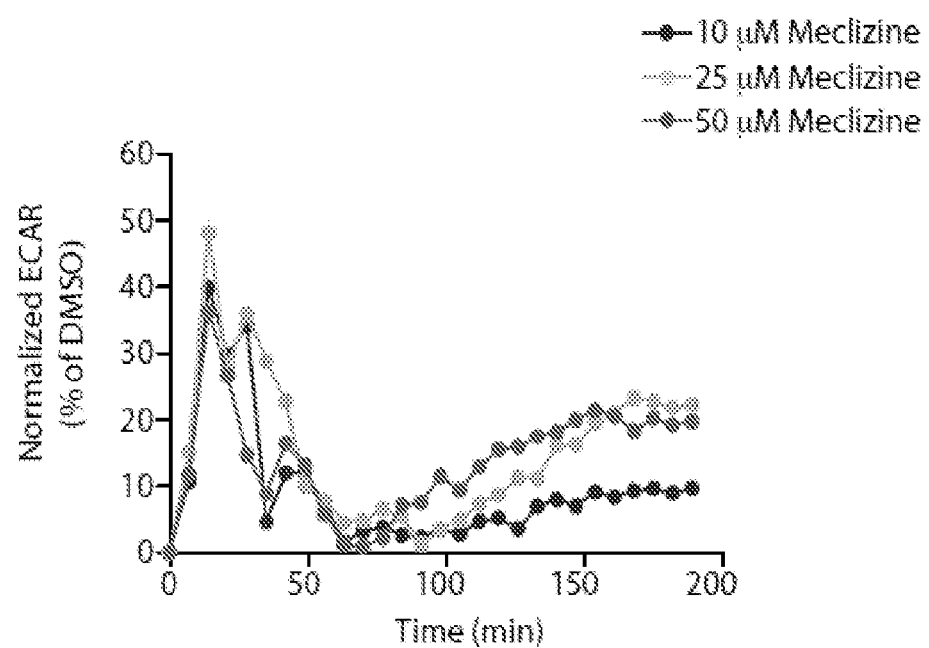
FIG. 3D presents exemplary data showing changes in ECAR from a DMSO baseline in MCH58 cells exposed to different concentration of meclizine over a three hour timeframe. Measurements are taken every seven minutes. Average of 5 replicates are shown.
Figure 3E:
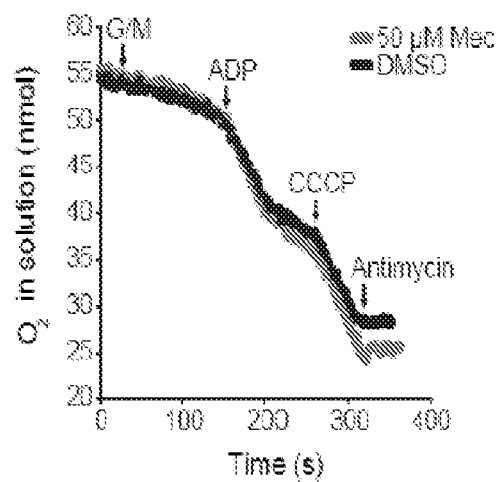
FIGS. 3E-I are line graphs showing the acute effect of meclizine on mitochondrial bioenergetic parameters in isolated mitochondria, including oxygen consumption, using glutamate/malate (3E), succinate (3F) or pyruvate/malate (3G) as substrates. Traces are representative of five independent measurements. (3H) Acute effect of meclizine on mitochondrial membrane potential measured with tetramethyl rhodamine methyl ester (TMRM) in isolated mitochondria. Traces are representative of five independent measurements. (3I) Acute effect of meclizine on mitochondrial NADH in isolated mitochondria. Traces are representative of five independent measurements. Mitochondria (Mito), glutamate and malate (G/M), succinate (S), pyruvate/malate (P/M), meclizine (Mec) or DMSO, ADP and carbonyl cyanide m-chlorophenyl hydrazone (CCCP) were added at indicated time points.
Figure 3F:
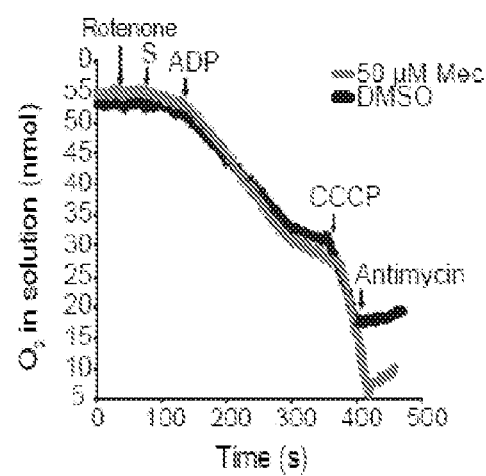
Figure 3G:
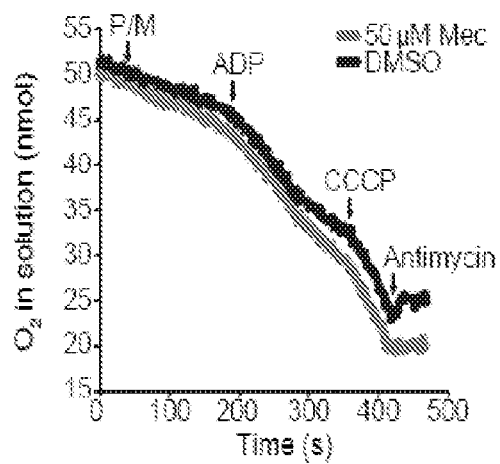
Figure 3H:
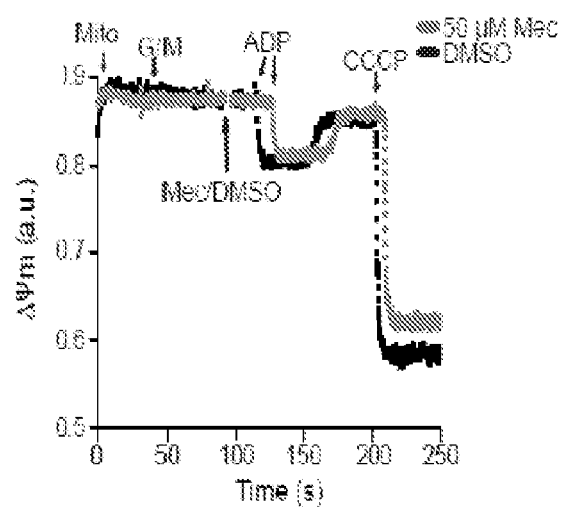
Figure 3I:
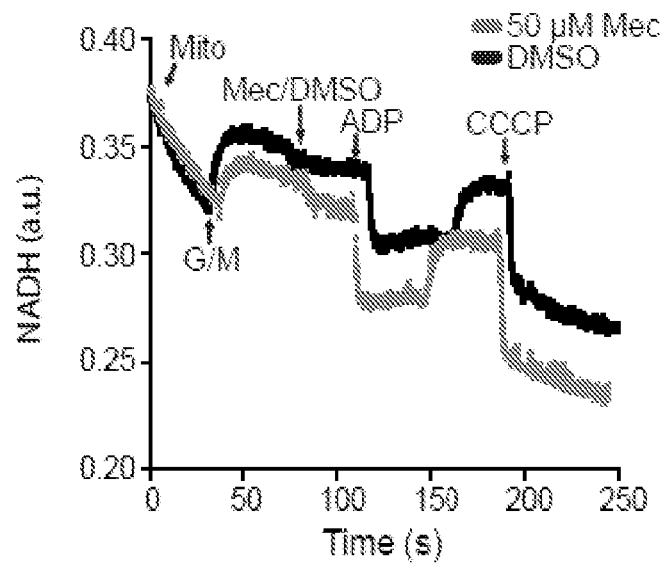
Figure 3J:
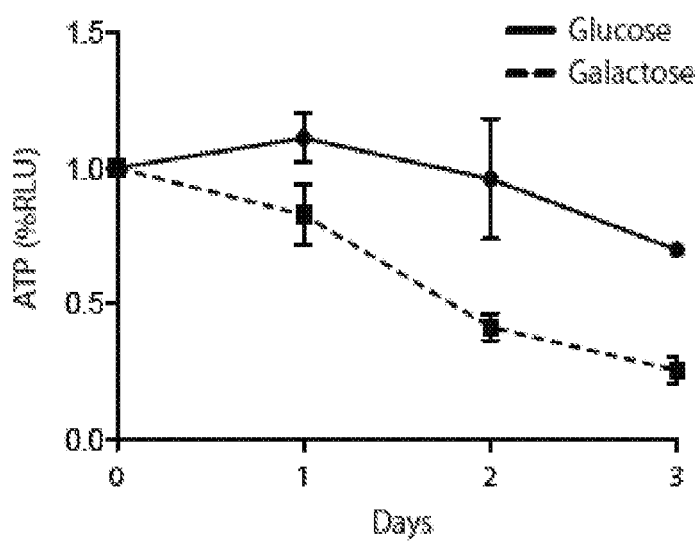
FIG. 3J presents exemplary data showing a time course of meclizine's effect on viability in glucose-rich versus galactose-rich media. MCH58 fibroblasts grown in 10 mM glucose or 10 mM galactose were treated with 50 µM meclizine for up to three days. Cellular ATP levels were calculated at each time point using the CellTiter-Glo relative luminescence (RLU) assay. Data are expressed as mean fold change over DMSO control±SD (n=5).

The first step in validating meclizine as a potential therapeutic drug was to confirm the primary screening results by using two different assays assessing both cell growth and cell viability. In preliminary screening, meclizine was found to retard the growth of fibroblasts in a dose dependent manner and over a three-day period. For example, MCH58 fibroblast cells grown in a galactose-rich media were observed to be more sensitive (i.e., exhibited decreased cell viability) to meclizine treatment than when grown in glucose-rich media. For example, an at least two-fold difference in the $LD_{50}$ values was identified, that was still less than $LD_{50}$ values observed for the classical OXPHOS inhibitors. Further, cellular ATP levels were also more sensitive to meclizine when grown in a galactose-rich media relative to a glucose-rich media. See FIGS. 3A, 3B, & 3J.

Figure 3K:
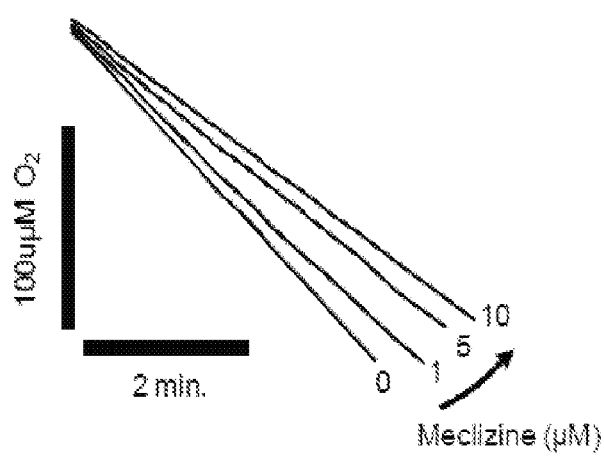
FIG. 3K is a line graph showing that Meclizine inhibits respiration in primary cardiomyocytes isolated from rat heart. Cardiomyocytes were exposed to the indicated concentration of meclizine for 20 min followed by oxygen measurement in the respiration chamber. Typical respiration traces are shown.
Figure 3L:
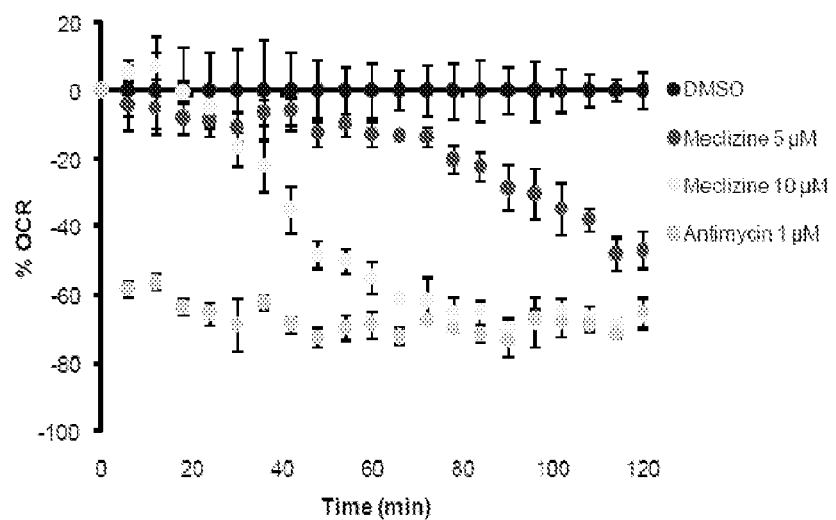
FIG. 3L is a line graph showing that Meclizine inhibits respiration in primary cortical neurons isolated from mouse embryos. Oxygen consumption rate (OCR) measurements following meclizine (5 and 10 μM) or antimycin (1 μM) addition at time 0 (min) in mouse primary cortical neurons obtained from day E14-15 embryos. Data are expressed as mean+/−SD (n≥3).
Figure 6A:
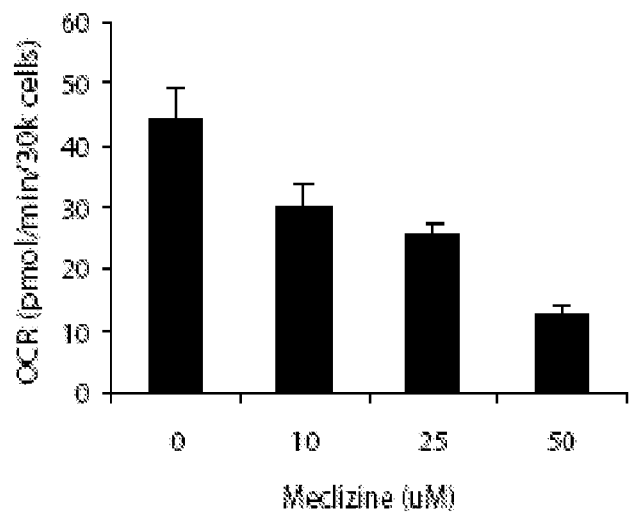
FIG. 6A presents exemplary data showing changes in oxygen consumption rates (OCR) in MCH58 fibroblasts exposed to different concentration of meclizine for 200 minutes. Data expressed as mean+/−SD (n=3).

Meclizine was confirmed to shift a cell's relative reliance on OXPHOS versus glycolysis by whole cell bioenergetic kinetic assays. For example, meclizine reduced oxygen consumption rates. See FIGS. 3C and 6A. This was true in primary cardiomyocytes isolated from rat heart (FIG. 3K) and primary cortical neurons isolated from mouse embryos (FIG. 3L). Cardiomyocytes were exposed to the indicated concentration of meclizine for 20 min followed by oxygen measurement in a respiration chamber. Oxygen consumption rate (OCR) measurements were made following meclizine (5 and 10 µM) or antimycin (1 µM) addition at time 0 (min) in mouse primary cortical neurons obtained from day E14-15 embryos.

Figure 6B:
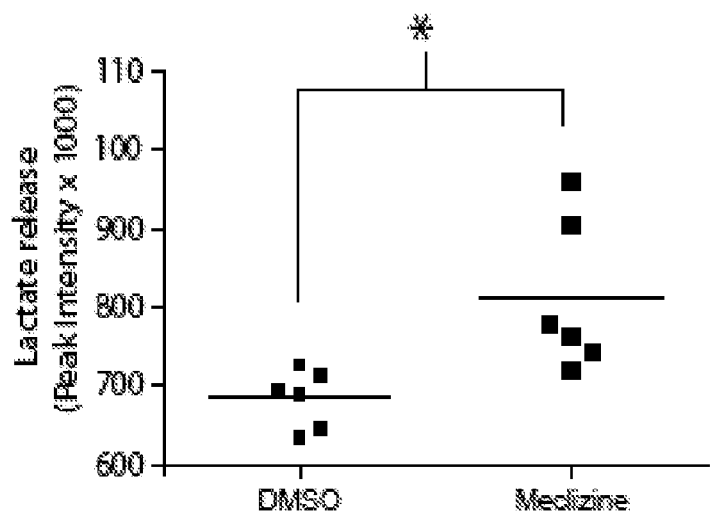
FIG. 6B presents exemplary data showing changes in lactic acid production rates by MCH58 fibroblasts after exposure to 50 μM meclizine for six hours. n=6; * indicates p<0.01.

Further, meclizine increased lactic acid production in a dose-dependent manner requiring several hours to develop. See FIG. 3D & FIG. 6B. Cells treated with meclizine accumulate lactic acid in their media over time, consistent with an increased reliance on glycolysis).

These meclizine-induced reductions in oxygen consumption and concomitant increase in extracellular acidification rate were also observed in other cell types including human skin fibroblasts, mouse striatal cells, human embryonic kidney cells, and Hela cells. See FIG. 7A, FIG. 7B, and FIGS. 8A-F. Meclizine is classified as a histamine receptor ($H_1$) antagonist and as a weak cholinergic receptor antagonist. Brunton and Parker, *Goodman and Gilman's The Pharmaco-* logical Basis of Therapeutics, The Mcgraw-Hill Companies, ed. 11, pg. 1889 (2006). However, the other sixty-four annotated $H_1$ receptor antagonists and thirty-three annotated antimuscarinic antagonists that were screened did not exhibit elevated $S_{glu/gal}$ scores (Anti-cholinergics: Mann-Whitney rank sum P=0.26; Anti-$H_1$s: Mann-Whitney rank sum P=0.77). These results suggest that meclizine may impact cellular energy metabolism via a mechanism distinct from blockade of cholinergic or histamine receptors.

Meclizine's suppression of oxygen consumption occurs at a slower time-scale relative to canonical inhibitors of OXPHOS. See FIG. 9. In fact, addition of meclizine to isolated mitochondria had no effect on mitochondrial oxygen consumption. See FIGS. 3E-3G. These observations suggested that meclizine may have a novel mechanism of action.

Additional experiments were performed to determine if the inhibitory effects of oxidative phosphorylation of meclizine were present in isolated mitochondrial preparations. For example, kinetic measurements of mitochondrial membrane potential and redox potential during mitochondrial respiratory state transitions were performed as follows.

Mitochondria were isolated from C57BL/6 mouse kidneys by differential centrifugation and resuspended in experimental buffer to a final concentration of 0.15 mg/ml. Mootha et al., Am J Physiol 272:H769 (1997). State 2 respiration was initiated with the addition of 2.5 mM glutamate and 2.5 mM malate. State 3 respiration was initiated with the addition of 50 nmoles ADP. Uncoupled respiration was initiated with the addition of 5 μM CCCP (Sigma Cat No C2759). $O_2$ consumption was monitored with a Fiber Optic Oxygen sensor probe from Ocean Optics, and NADH (endogenous, 370±7 nm excitation, 440±4 nm emission) and membrane potential (1.25 μM TMRM, 546±7 nm excitation, 590±4 nm emission) were measured with a Perkin-Elmer LS50B fluorimeter. A representative trace is shown from 6 independent experiments. 1M stock of phosphoethanolamine (Sigma P0503) was made in sterile water and pH was adjusted to 7.4 by 1N potassium hydroxide solution.

Figure 3M:
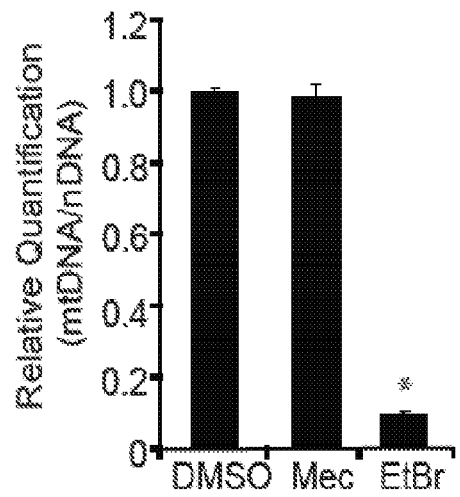
FIGS. 3M-N are bar graphs showing that meclizine does not alter mitochondrial DNA copy number (3M) or mitochondrial mRNA expression (3N). *P<0.001; two-sided t-test (n=3 for each).
Figure 3N:
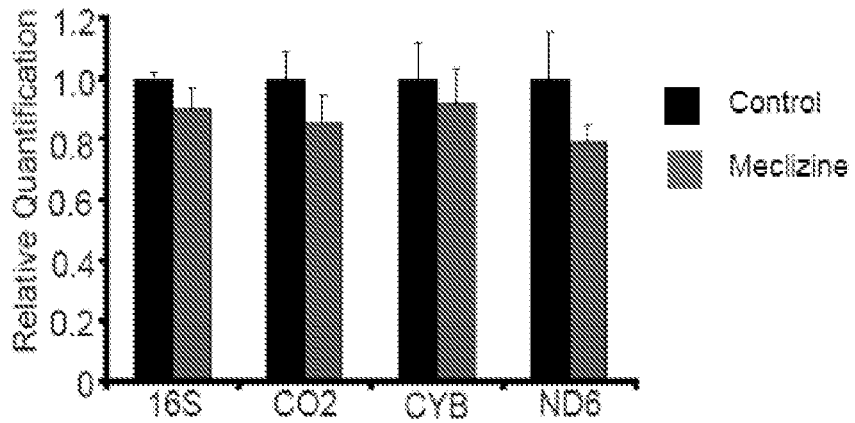

The results were substantially identical in the presence or absence of meclizine, indicating that it is not a direct inhibitor of the electron transport chain or of oxidative phosphorylation. See FIGS. 3E-3I. In addition, as shown in FIGS. 3M-N, meclizine does not alter mitochondrial DNA copy number or mitochondrial mRNA expression. HeLa cells were exposed to 50 μM meclizine (Mec) for 6 hours or 50 ng/ml ethidium bromide (EtBr) for 3 days followed by total genomic DNA extraction. Mitochondrial DNA copy number was measured by quantitative real-time PCR with Taqman assays for a nuclear and a mitochondrial gene. Total RNA was extracted from HeLa cells treated with 50 μM meclizine for 6 hours. Mitochondrial DNA encoded transcripts were measured by quantitative real-time PCR with gene specific Taqman assays.

These data suggest that meclizine does not itself directly inhibit the OXPHOS machinery. These data are consistent with the observed slow kinetics (i.e., over a few hours) of meclizine's effect on oxygen consumption in whole cells. See FIG. 3C.

The above studies reveal that meclizine is capable of shifting cellular energy metabolism from oxidative phosphorylation (OXPHOS) to glycolysis in all cell types tested. This action of meclizine was not previously known. Moreover, an ability for meclizine to shift cells from OXPHOS to glycolysis may be responsible for its ability to confer cytoprotection against oxygen-glucose deprivation in cultured neurons, as well as protection against polyglutamine toxicity in cellular models of Huntington's disease, and against ischemic injury.

Example 3

S-Meclizine Affects Cellular Energy Metabolism

Commercially available meclizine is a racemic mixture, comprising R-meclizine and S-meclizine. Consequently, meclizine enantiomers were prepared and assessed for their respective ability to reduce cellular oxygen consumption rates and/or stereoselectivity.

First, the two enantiomers were synthesized as shown in Scheme I, above, using the following methods.

Step 1 (R) and (S)-4-chlorobenzhydrylamine

The racemic 4-chlorobenzhydrylamine was treated with D-tartaric acid, and then sequentially recrystallized ten times from water (as described by Clemo, et al., J. Chem. Soc., (1939), 1958-1960) to provide (S)-4-chlorobenzhydrylamine of high optical purity (ee>98%, according to chiral HPLC).

In a similar manner, treatment of racemic 4-chlorobenzhydrylamine with L-tartaric acid provided (R)-4-chlorobenzhydrylamine of high optical purity (ee>98%, according to chiral HPLC)

Step 2: (R) and (S)1-((4-chlorophenyl)(phenyl)methyl)piperazine 1-((4-chlorophenyl)(phenyl)methyl)piperazine was prepared as described in Opalka, et al., Synthesis 1995, 766-768.

Step 4: (R)-Meclizine and (S)-Meclizine

A mixture containing (S)-1-[(-4-chlorophenyl)phenylmethyl]piperazine (50 mg, 0.18 mmol), 3-methylphenylmethyl bromide (0.025 ml, 0.19 ml), potassium carbonate (80 mg) and methanol (3 ml) was stirred under reflux for overnight. The mixture was then cooled to room temperature and filtered. The filtrate was concentrated and then purified by chromatography over silica-gel to afford 10 mg of S-Meclizine as a yellow oil, which was further converted to its hydrochloride salt. MS: 391 (M+1); ee: >99% (retention time=22.6 min; CHIRALPAK OD-H column; Mobile phase: Hexanes (0.1% diethyl amine (DEA)).

Oxygen consumption rate (OCR) measurements were performed as described above. Briefly, HEK 293 cells were seeded in XF24 cell culture microplates (Seahorse Bioscience) at 50,000 cells/well in DMEM High glucose media, supplemented with 10% fetal bovine serum. The cells were incubated overnight at 37° C. with 5% CO2. Prior to the measurements, the growth medium was replaced with ~925 μL of assay medium devoid of serum. The cells were incubated at 37° C. for 30 min in the assay medium prior to measurements. The measurements were performed every 6 minutes after a 2 minute mix and 2 minute wait period. Three baseline measurements were recorded prior to the addition of R-meclizine, S-meclizine, or racemic meclizine. The stock solution of all the above compounds were made in 100% DMSO, which was diluted to specified concentration in assay medium and its pH was adjusted to 7.4 by 1N Sodium Hydroxide solution.

The data demonstrates that S-meclizine and R-meclizine are capable of suppressing oxygen consumption. S-meclizine and R-meclizine inhibit cellular oxygen consumption rate (OCR) in a dose dependent manner. Both enantiomers inhibit OCR between 60-80% at dosages ranging between 25-50 µM, see FIGS. 24A-B.

The ability of meclizine, S-meclizine and R-meclizine to activate AMPK in C2C12 myotubes was also evaluated using Western blot detection of AMPK phosphorylation in C2C12 myotubes following 24 hours of treatment with R-meclizine (R-Mec), S-meclizine (S-Mec) and the racemic mixture (Rac-Mec). The results, shown in FIG. 24C, demonstrate that meclizine, S-meclizine and R-meclizine all activate AMPK in C2C12 myotubes.

The ability of each enantiomer to bind to the $H_1$ receptor was evaluated using a competitive binding experiment with the racemate. In vitro binding of R-meclizine (R-Mec) and S-meclizine (S-Mec) to human H 1 receptor was determined by competitive binding assays in the presence of 3 nM [3H] pyrilamine. Non-specific binding was determined in the presence of excess (1 µM) unlabeled Pyrilamine. IC50 were determined by non-linear regression analysis of the competition curves.

Figure 24C:
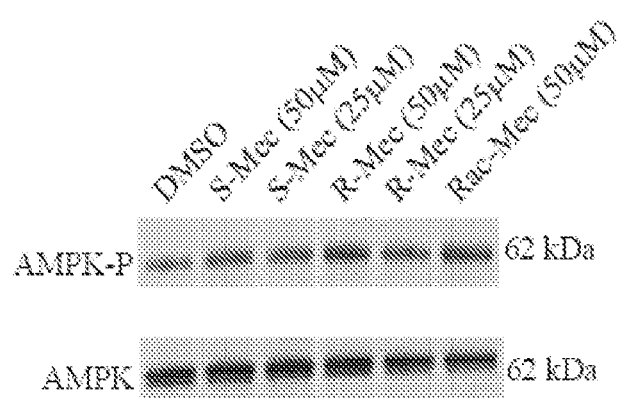
FIG. 24C is a Western blot showing that Meclizine, S-meclizine and R-meclizine activate AMPK in C2C12 myotubes.
Figure 24D:
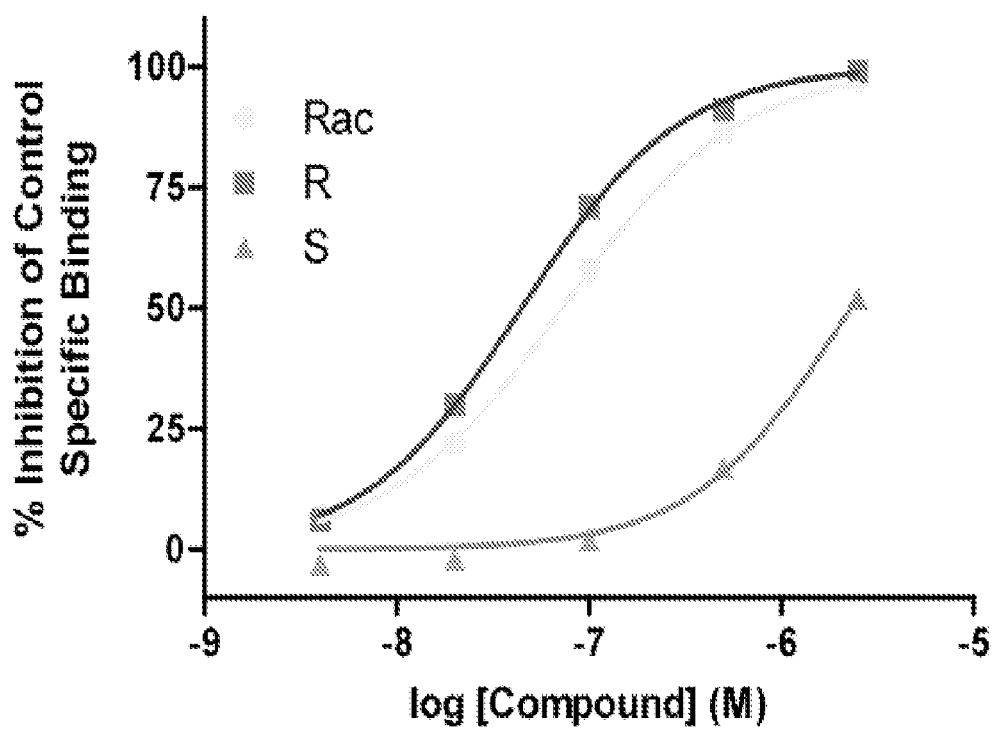
FIG. 24D is a line graph showing that R-mec, but not S-mec, binds to the $H_1$ receptor.
Figure 24E:
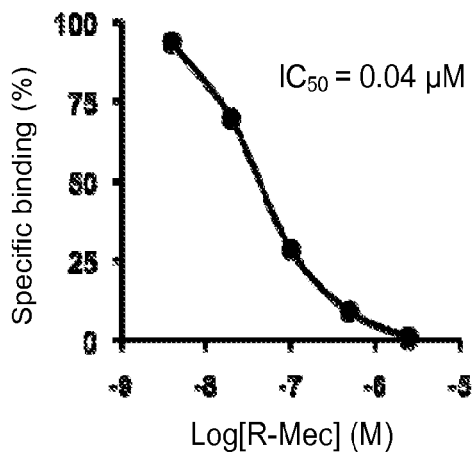
FIGS. 24E-F are line graphs showing that R-meclizine (24E) is much more potent against the histamine receptor than is S-meclizine (24F).
Figure 24F:
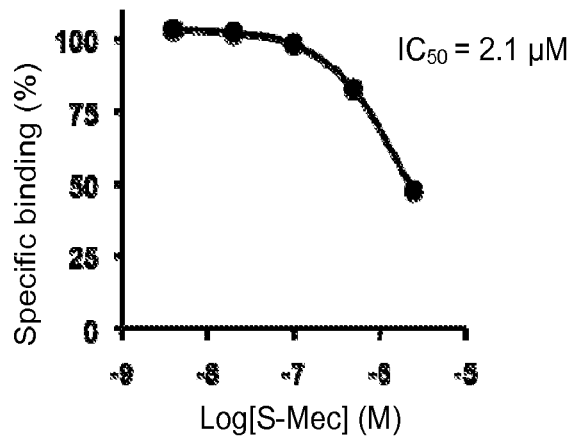

Surprisingly, as shown in FIGS. 24D-F, R-mec bound to the $H_1$ receptor with high affinity, while S-mec exhibited much weaker affinity on the $H_1$ receptor. This indicates that in a living subject, the side effects of meclizine administration that are associated with antihistamine activity (such as drowsiness and/or sedation) are not likely to be associated with administration of the S-enantiomer.

Example 4

Mechanism of Meclizine Action

The above data shows that meclizine: i) induces a slow kinetic switch from OXPHOS to glycolysis; and ii) does not directly inhibit respiration. One explanation for these data might be that meclizine is capable of switching cellular energy metabolism via a metabolic or transcriptional rewiring mechanism.

A. Gene Expression Profiling

Figure 10A:
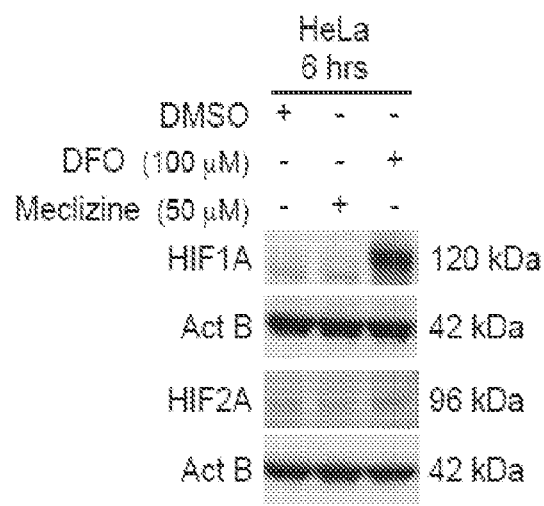
FIGS. 10A-10B present exemplary data showing the effect of meclizine on HIF-1α stabilization. 10A, HIF-1α and HIF-2α detection by western blot analysis of protein extract from HeLa cells after 6-h treatment with 0.1% DMSO, 100 μM deferoxamine (DFO) or 50 meclizine. 10B, a bar graph showing HIF reporter activity measured in transiently transfected HeLa cells following 6 hours treatment with DMSO, 100 μM DFO or 50 μM Mec. NTC refers to non-transfected control. Data is representative of 2 independent experiments done in triplicate. (*P<0.05; two sided t-test).
Figure 10B:
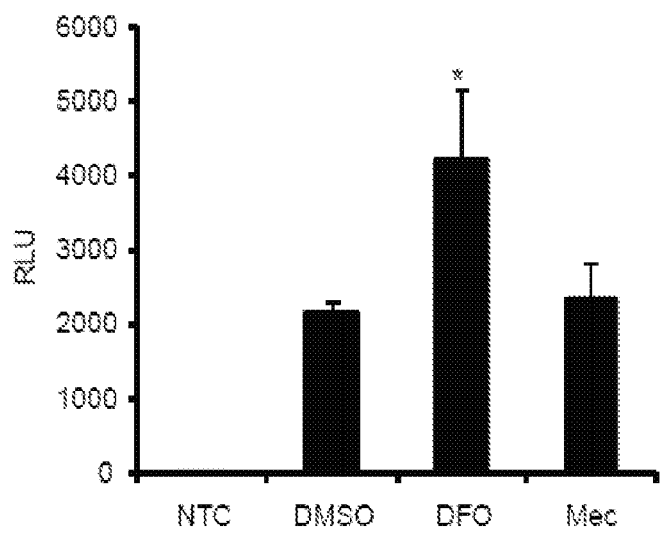

To explore this hypothesis, activation of glycolysis via hypoxia inducible factor (HIF), a known transcriptional activator of glycolysis, was tested. HIF1-α and HIF2-α stabilization was assessed in HeLa cells by carrying out Western blot analysis using anti-HIF1-α antibody (Cell Signaling Cat. No. 3716) and anti-HIF2-α antibody (Novus Biologicals). Protein was extracted from cells pre-treated with either 0.1% DMSO, 50 µM meclizine or 100 µM deferoxamine (Sigma Cat. No. D9533). Western detection of Glutaminase (GLS) was carried out on protein extracts from 293 cells using anti-GLS antibodies (gift from Dr. Javier Marquez, University of Malaga, Spain). No HIF stabilization following meclizine treatment was observed. See FIGS. 10A-B.

Next, a global gene expression profile was performed on fibroblasts following a six hour meclizine treatment (i.e., a time point having maximal OXPHOS inhibition). Oligonucleotide microarray experiments were conducted as follows. Total RNA was extracted from ~2 million MCH58 cells with RNeasy mini kit (Qiagen). Cells were either grown in 10 mM glucose or 10 mM galactose for 3 passages and for the drug treated samples, and treated with either 0.1% DMSO or 50 µM meclizine for 6 hours. 10 ug of RNA was used to synthesize cDNA with a T7-(dT)$_{24}$ primer and the SuperScript one-cycle cDNA synthesis kit (Affymetrix). cRNA labeling, hybridization to human U133 plus 2.0 oligonucleotide array (Affymetrix, CA), washing and staining were performed as recommended by Affymetrix. For each condition, 3 biological replicates were used for the total of 6 arrays. GLS expression was confirmed by quantitative RT-PCR using TaqMan assay (Applied Biosystems).

Figures 11A, 11B:
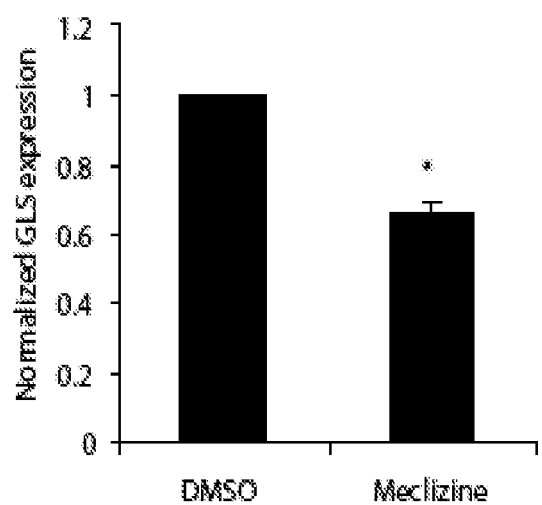
FIG. 11A presents exemplary data identifying differentially expressed genes (with FDR<0.175) in MCH58 fibroblasts following 6 hours of exposure to 50 μM meclizine in glucose-rich media where mRNA levels measured using Affymetrix U133 plus2.0 gene expression arrays (n=3).
FIG. 11B presents exemplary data showing GLS expression as measured by qRT-PCR (n=3, *P<0.005).

At the most stringent false-discovery rate (FDR=0.174), the data set comprised fourteen (14) genes whose expression were increased or decreased relative to vehicle treatment. See, e.g., Hochberg et al., Stat Med 9:811 (1990). The data demonstrated that the one downregulated gene is GLS, which encodes glutaminase, was downregulated by ~40% ($p<10^{-4}$). See FIGS. 11A and 11B. Glutaminase is believed to be the enzyme responsible for converting glutamine into glutamate within mitochondria.

In addition, the global gene expression profiling data also revealed that meclizine upregulated a number of glycolytic enzymes (e.g., HK2; showing a 1.5 fold change, $p<10^{-3}$). On the other hand, a negative regulator of cellular glucose uptake (e.g., TXNIP) was downregulated by 35%. Parikh et al., PLoS Medicine 4:e158 (2007).

A motifADE was performed to determine whether these meclizine-induced global gene expression changes are associated with over-represented cis-regulatory motifs. Mootha et al., PNAS USA 101:6570 (2004). An E-box binding site (e.g., 5'-CACGTG-3') was identified (Bonferroni corrected; $p<10^{-5}$). The E-box binding site has been identified to be involved in a variety of transcriptional regulators, including the glucose responsive transcription factors such as ChREBP and MONDO.

B. GLS Transcription Analysis

RNAi and c-DNA overexpression expression experiments to evaluate GLS were performed as follows. Lentiviral particles either containing empty vector (pLKO.1) or with vector expressing shRNA against GLS (GCACAGACATGGTTG-GTATAT) (SEQ ID NO:1). Following transduction with the lentiviral particles, MCH58 fibroblasts were selected in puromycin (2 µg/ml) and expanded to make stable knockdown. GLS knockdown was confirmed by quantitative RT-PCR using TaqMan assay. These cells were used to carry out metabolic state dependent sensitivity and OCR and ECAR assays.

Figure 14A:
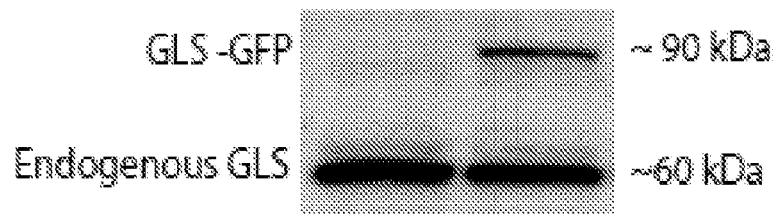
FIG. 14A presents exemplary data showing constitutive expression of GLS-GFP fusion protein from a CMV promoter. Western blot analysis using anti-GLS antibodies.
Figure 14B:
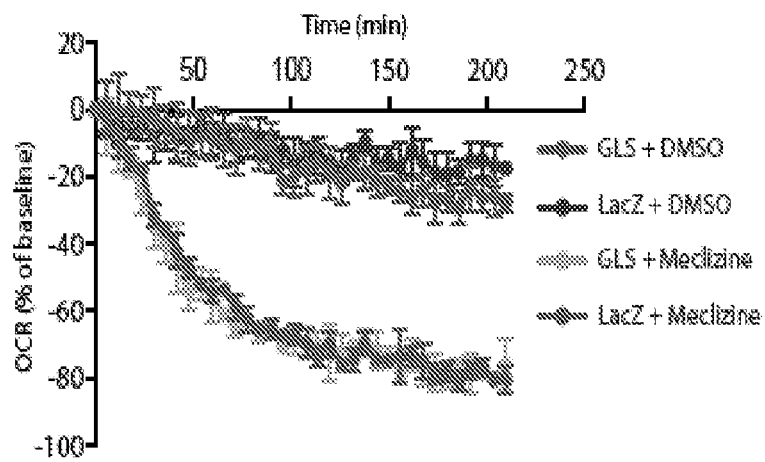
FIG. 14B presents exemplary data showing OCR measurements on FACS sorted control (LacZ) or GLS expressing cells following DMSO or 50 μM meclizine addition at time 0 min (n=4).

Glutaminase full length cDNA (Open Biosystems, Accession #BCO38507) was amplified using proof-reading TAQ polymerase (Accuprime, Invitrogen) with primers which included attb1 and attb2 sites for subsequent subcloning into pDONR 221 vector (Invitrogen). Partial Kozak sequence was included in the 5' primer and stop codon was eliminated in the 3' primer. The sequences of forward (F) and reverse primers (R) are—5'-GGG GAC AAG TTT GTA CAA AAA AGC AGG CTC CAC CAT GAT GCG GCT GCG AGG CTC-3' (SEQ ID NO: 2); and 5'-GGG GAC CAC TTT GTA CAA GAA AGC TGG GTC CAA CAA TCC ATC AAG ATT CT-3' (SEQ ID NO: 3), respectively. Resulting PCR fragment was cloned into Gateway entry vector pDONR 221 (Invitrogen) with BP clonase using STBL2 E. coli competent cells (Invitrogen). Subsequently, it was subcloned into destination vector pcDNA6.2-EMGFP-DEST with LR clonase and was sequenced verified. The 293 cells were transfected with the pcDNA6.2-GLS-GFP and the control vector pcDNA6.2-LacZ-GFP using Fugene (Roche) reagent. GLS expression was confirmed by Western blot using anti-GLS antibody. See FIG. 14A. FACS sorted transfected cells were subjected to meclizine treatment followed by OCR and ECAR measurements. See FIG. 14B.

GLS is a mitochondrial enzyme and converts glutamine into glutamate, which is a critical anaplerotic substrate for the TCA cycle and serves as a precursor for ATP synthesis. See FIGS. 1A & 1B. In galactose rich media, cells are observed to rapidly consume glutamine and GLS is upregulated by ~30% relative to glucose conditions.

Figure 4A:
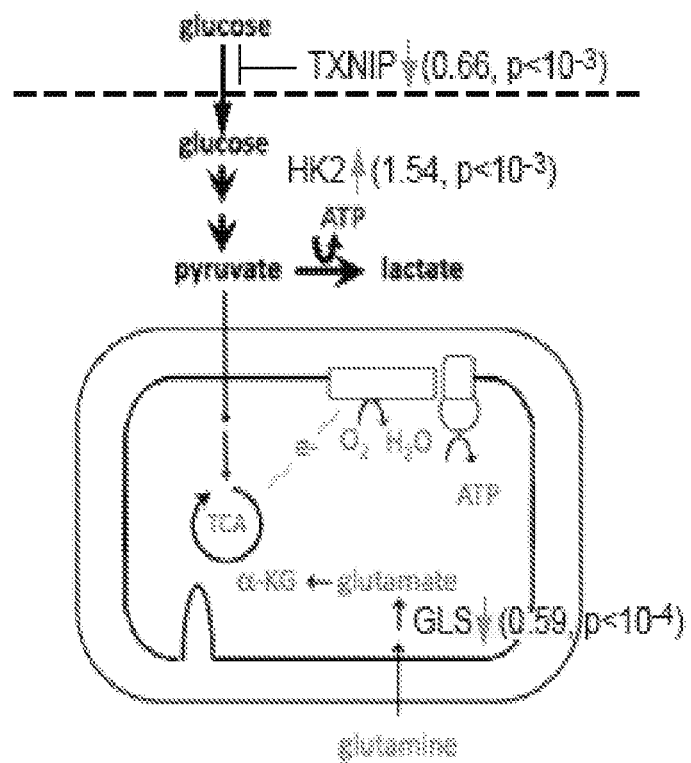
FIG. 4A presents exemplary genomewide RNA profiling data showing mRNA levels for: i) glutaminase (GLS); ii) Hexokinase (HK2); and iii) Thioredoxin interacting protein (TXNIP) in cells grown in glucose treated with 50 μM meclizine or DMSO. Data are expressed as mean±SE; * represents p-value <0.05 by two-sided t-test (n=3).
Figure 4B:
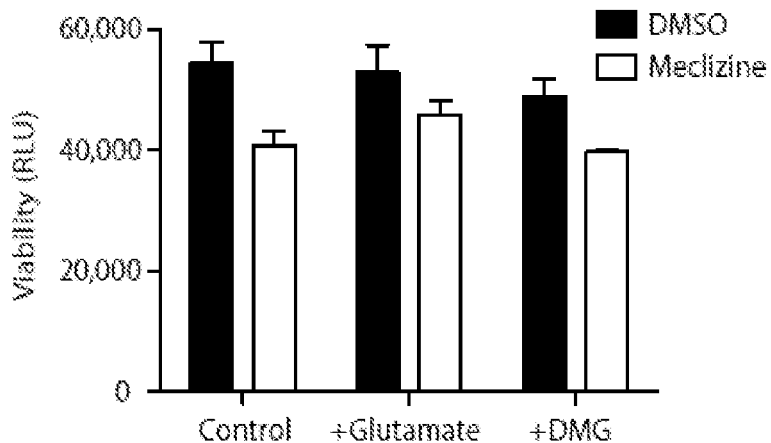
FIG. 4B presents exemplary data showing cellular viability (Cell titer-Glo®) for cells grown in glucose medium in the presence of DMSO or 50 μM meclizine, as well as treatment with 20 mM glutamate and 2.5 mM dimethyl glutamate. DMSO—Solid Bars. Meclizine—Open Bars.
Figure 4C:
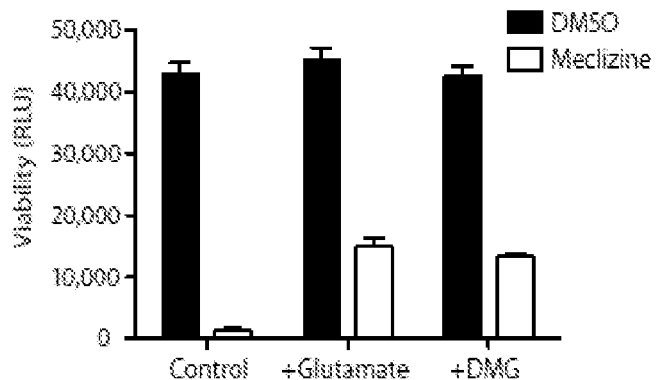
FIG. 4C presents exemplary data showing cellular viability (Cell titer-Glo®) for cells grown in galactose medium in the presence of DMSO or 50 μM meclizine as well as treatment with 20 mM glutamate and 2.5 mM dimethyl glutamate. DMSO—Solid Bars. Meclizine—Open Bars.

If reduced GLS expression is related to metabolic state-dependent lethality, then meclizine treated cells grown in galactose should be rescued by the addition of glutamate (e.g., a product of mitochondrial glutaminase activity). Consequently, meclizine treated cells in a galactose rich media were incubated with glutamate as well as the cell permeant ester dimethylglutamate. Although it is not necessary to understand the mechanism of an invention, it is believed that both of these metabolites should get taken up into the cells, transported into mitochondria, and converted via glutamate dehydrogenase to oxoglutarate to serve as an anaplerotic precursor in the TCA cycle. However, a rescue of meclizine-induced inhibition of cell viability was not observed. See FIGS. 4B & 4C. Later findings indicate that GLS transcriptional changes are play ra role in glutamine-mediated respiration, but are not likely to be the primary primary drivers of the metabolic changes that occur after meclizine treatment.

Figure 12A:
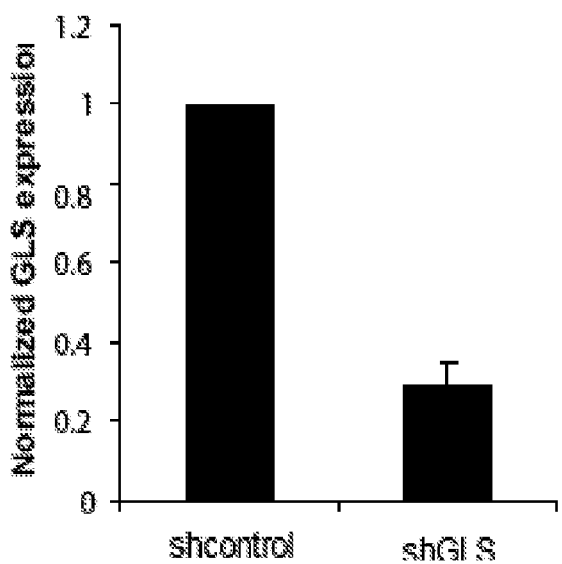
FIG. 12A presents the exemplary data showing that GLS expression was reduced by shRNA targeting GLS.
Figure 12B:
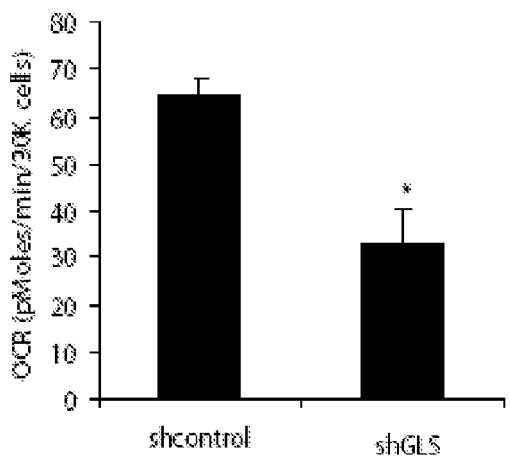
FIG. 12B presents exemplary data showing that cellular OCR was reduced by shRNA targeting GLS in stably transduced shGLS cells (n=5, *P<10$^{-4}$).
Figure 13:
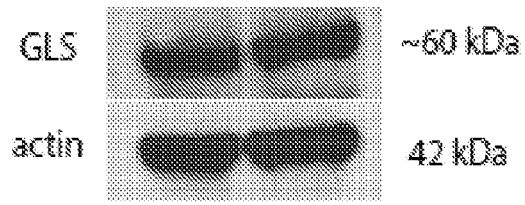
FIG. 13 presents exemplary data of a Western blot analysis of meclizine's effect on GLS protein level.

Further experiments confirmed: i) a 50% reduction in GLS transcript by quantitative real-time PCR following 6 hours of meclizine treatment; and ii) shRNA mediated silencing of GLS expression resulted in the selective loss of viability of galactose grown cells. For example, RNAi against GLS diminished oxygen consumption and gave rise to metabolic state dependent lethality. See FIGS. 12A and 12B. However, the GLS protein was not reduced following meclizine treatment. See FIG. 13. Further, meclizine continued to suppress oxygen consumption even in cells where a constitutive promoter forced GLS expression. See FIGS. 14A and 14B. Collectively, these data suggest the drop in GLS transcript levels might be secondary to an energetic effect of meclizine.

C. Evaluation of Metabolites

To gain further insights on the mechanism of action of meclizine in reducing oxidative metabolism, mass spectrometry-based metabolic profiling was performed on cells treated with meclizine.

Metabolite profiling was performed on MCH58 fibroblasts following treatment with 50 µM meclizine or vehicle control for six hours, using methods similar to those previously described, see Shaham et al., Mol Syst Biol 4:214 (2008). Briefly, low passage MCH58 cells were cultured on 6 cm tissue culture dishes in 4 mL of culture media to 90% confluency and a final yield of $1 \times 10^6$ cells. For assessment of media metabolites, 500 µl of spent media or baseline media (prior to addition to cells) were sampled from the culture dish and immediately added to 500 µl of pre-cooled (−80° C.) methanol extraction solution (80% methanol, 20% $H_2O$) to allow for rapid quenching of metabolism and extraction of metabolites. After 20 minutes at 4° C., samples were centrifuged at 14,000 g for 10 minutes. 50 µl of the supernatant was collected, re-diluted 1:20 with methanol extraction solution, and 100 µl of the final solution evaporated under nitrogen. Samples were reconstituted in 60 µl of HPLC-grade water and metabolite levels determined, as described below. For assessment of intracellular metabolites, media was aspirated from the above tissue culture plates and cells gently washed with 4 mL of PBS, to ensure complete removal of residual media metabolites. The PBS was removed and cellular metabolism quenched with immediate addition of 1 mL of pre-cooled (−80° C.) methanol extraction solution (80% methanol, 20% $H_2O$). Cells were scraped, collected in extraction solution, vortexed and the samples centrifuged as described above for preparation of media samples. 100 µl of the supernatant was collected, re-diluted 1:1 with methanol extraction solution, and 100 µl of the final solution evaporated under nitrogen. Samples were reconstituted in 60 µl of HPLC-grade water and metabolites assessed. Six biological replicates were assessed for each group.

Analyses of endogenous metabolites were performed using a liquid chromatography tandem mass spectrometry (LC-MS) system composed of a 4000 QTRAP triple quadrupole mass spectrometer (Applied Biosystems/SCIEX) coupled to three Agilent 1100 binary HPLC pumps (Agilent Technologies) and an HTS PAL autosampler (LEAP Technologies) equipped with three injection ports and a column selector valve. Three multiplexed chromatographic methods were configured for the analyses of each sample: LC method 1 used a Luna Phenyl-Hexyl column (Phenomenex) eluted with a linear gradient of water/acetonitrile/acetic acid (initial proportions 100/0/0.001, final proportions 10/90/0.001); LC method 2 used a Luna NH2 column with normal phase, gradient elution using acetonitrile/water mobile phases containing 0.25% ammonium hydroxide and 10 mM ammonium acetate (acetonitrile/water proportions were 80/20 at the beginning of the gradient and 20/80 at its conclusion); LC method 3 used a Synergi Polar-RP column (Phenomenex) with reversed phase, gradient elution using 5% acetonitrile/5 mM ammonium acetate (mobile phase A) and 95% acetonitrile/5 mM ammonium acetate (mobile phase B). MS data were acquired using multiple reaction monitoring (MRM) in both the positive (LC method 1) and negative (LC methods 2 and 3) ion modes. During the development of this method, authentic reference compounds were used to determine LC retention times and to tune MRM transitions. Metabolite quantification was performed by integrating peak areas for specific MRM transitions using MultiQuant software (version 1.1; Applied Biosystems/SCIEX) and all integrated peaks were manually reviewed for quality.

Extraction and quantification procedures were optimized prior to assessment of samples in this study to ensure measured intracellular and media metabolites were within the linear range of detection. Confirmation of the phosphoethanolamine peak was performed using an exogenous phosphoethanolamine standard (Sigma P0503).

Of the approximate one hundred and twenty-five (~125) measured metabolites, a total of six (6) showed significantly altered intracellular levels after correcting for multiple hypothesis testing ($P_{adj}$<0.05). See Table 4.

TABLE 4

Representative listing of metabolites following meclizine treatment

| Sample Name | Fold Change | $P_{adj}$ Value |
| --- | --- | --- |
| P1_M0014_Asparagine | 2.43 | 0.00 |
| P1_M0008_Alanine | 1.40 | 0.00 |
| P1_M0054_Phosphoethanolamine | 38.21 | 0.00 |
| P4_M0090_Cystathionine | 1.53 | 0.01 |
| P1_M0062_Taurine | 1.59 | 0.03 |
| P1_M0015_Aspartate | 1.25 | 0.04 |
| P1_M0027_Cytidine | 1.28 | 0.08 |
| P4_M0159_CDP | 1.52 | 0.13 |

TABLE 4-continued

Representative listing of metabolites following meclizine treatment

| Sample Name | Fold Change | $P_{adj}$ Value |
|---|---|---|
| P3_M0127_Lactose | 0.42 | 0.15 |
| P4_M0187_SuccinicAcid | 0.83 | 0.15 |
| P1_M0022_Creatine | 1.47 | 0.31 |
| P1_M0055_Proline | 1.28 | 0.34 |
| P4_M0161/M0172_CitricAcid/IsocitricAcid | 0.66 | 0.40 |
| P1_M0046_Metanephrine_p2 | 0.87 | 0.74 |
| P1_M0067_Tyrosine | 1.18 | 0.82 |
| P4_M0180_OH-PhenylPyruvate | 0.86 | 0.85 |
| P4_M0191_Xanthosine-5'-monophosphate | 1.75 | 0.86 |
| P4_M0184_PantothenicAcid | 1.29 | 0.95 |
| P1_M0034_GlutamicAcid_p2 | 1.16 | 0.99 |
| P1_M0041_Hydroxyproline | 1.17 | 1.00 |
| P1_M0040_Homoserine | 1.14 | 1.00 |
| P4_NM002-M109_Glucose-13C6-d7 | 1.15 | 1.00 |
| P1_M0063_Threonine | 1.14 | 1.00 |
| P3_M0154_Methylmalonate | 0.86 | 1.00 |
| P4_M0083_ATP_D159 | 1.27 | 1.00 |
| P4_M0108_GDP_p1 | 1.38 | 1.00 |
| P1_M0058_Serine | 1.11 | 1.00 |
| P4_M0121_Hypoxanthine | 0.76 | 1.00 |
| P3_M0100_FolicAcid | 0.63 | 1.00 |
| P4_M0089_CTP | 1.32 | 1.00 |
| P4_M0166_Glucuronate | 0.77 | 1.00 |
| P4_M0188_TaurochenodeoxycholicAcid | 0.76 | 1.00 |
| P3_M0145/M0146_UDP-Glucose/UDP-Galactose_p2 | 1.33 | 1.00 |
| P4_M0206_Acetyl-CoA_P404 | 1.22 | 1.00 |
| P4_M0144_UDP | 1.21 | 1.00 |
| P1_M0066_Tryptophan | 1.13 | 1.00 |
| P3_M0147_UDP-GlucuronicAcid | 1.45 | 1.00 |
| P4_M0116_GTP | 1.24 | 1.00 |
| P3_M0195_3-PhosphoglycericAcid | 1.45 | 1.00 |
| P3_M0081_ADP_p2 | 1.43 | 1.00 |
| P1_M0042/M0044_Ile/Leu | 0.91 | 1.00 |
| P4_M0205_PhosphoTyrosine | 1.23 | 1.00 |
| P1_M0200_L-NMMA | 0.59 | 1.00 |
| P1_M0038_Histidine | 1.07 | 1.00 |
| P1_M0068/M0037_Valine/GuanidinoaceticAcid | 0.94 | 1.00 |
| P3_M0150_Uridine | 0.88 | 1.00 |
| P3_M0109-M0110_Glucose/Galactose | 0.94 | 1.00 |
| P1_M0035_Glutamine | 1.05 | 1.00 |
| P4_M0088_CMP | 1.27 | 1.00 |
| P4_M0190_UricAcid | 0.87 | 1.00 |
| P4_CAP193_Met-165 | 0.90 | 1.00 |
| P3_M0112_GlutathioneReduced | 1.74 | 1.00 |
| P3_M0139_Sorbitol | 0.92 | 1.00 |
| P4_M0210_Pyruvate | 1.08 | 1.00 |
| P4_M0162_Citrulline | 0.87 | 1.00 |
| P1_M0053_Phenylalanine | 1.09 | 1.00 |
| P4_M0100_FolicAcid | 0.84 | 1.00 |
| P1_M0019_Choline | 0.90 | 1.00 |
| P4_M0169_GlycocholicAcid | 0.68 | 1.00 |
| P1_M0009_Allantoin | 0.91 | 1.00 |
| P4_M0207_Malonyl-CoA_p1 | 1.16 | 1.00 |
| P1_M0016_Betaine | 1.08 | 1.00 |
| P3_M0152_Xanthine | 0.85 | 1.00 |
| P3_M0102/M0103/M0196_F16DiP/F26DiP/G16DiP_D79_p2 | 1.32 | 1.00 |
| P4_M0168_GlycochenodeoxycholicAcid | 0.83 | 1.00 |
| P4_M0126_LacticAcid | 0.96 | 1.00 |
| P3_M0111_GlutathioneOxidized | 1.20 | 1.00 |
| P1_M0045_Lysine | 1.08 | 1.00 |
| P4_M0170_HippuricAcid | 0.86 | 1.00 |
| P4_M0198_AconiticAcid(CAP203)_D129 | 0.55 | 1.00 |
| P1_M0026_Cysteine | 1.38 | 1.00 |
| P4_M0092_DCMP | 1.17 | 1.00 |
| P4_M0164/M0175_FumaricAcid/MaleicAcid | 0.94 | 1.00 |
| P1_M0050_Niacinamide | 1.08 | 1.00 |
| P3_M0121_Hypoxanthine | 1.17 | 1.00 |
| P4_M0183_Oxaloacetate | 0.92 | 1.00 |
| P4_M0102/M0103/M0196_F16DiP/F26DiP/G16DiP_D79_p1 | 1.14 | 1.00 |
| P3_M0082_AMP | 1.31 | 1.00 |
| P1_M0003_2'-deoxycytidine | 1.13 | 1.00 |
| P3_M0114_Glycerol-3-P | 1.21 | 1.00 |
| P3_M0164/M0175_FumaricAcid/MaleicAcid | 1.07 | 1.00 |
| P1_M0070_Xanthosine | 1.21 | 1.00 |
| P4_M0123_Inosine_p2 | 1.18 | 1.00 |
| P3_M0129_NAD | 1.11 | 1.00 |

TABLE 4-continued

Representative listing of metabolites following meclizine treatment

| Sample Name | Fold Change | $P_{adj.}$ Value |
|---|---|---|
| P3_M0130_NADP | 1.24 | 1.00 |
| P3_M0149_Uracil | 0.90 | 1.00 |
| P1_M0047_Methionine | 1.06 | 1.00 |
| P4_M0151_UTP | 1.09 | 1.00 |
| P3_M0077_Acetoacetate | 1.07 | 1.00 |
| P3_M0140_Sucrose | 1.18 | 1.00 |
| P4_M0137/M0138_Ribose-5-P/Ribulose-5-P_D97 | 1.07 | 1.00 |
| P1_M0204_Glycerol | 0.94 | 1.00 |
| P4_M0167_Glycerate-2-P_p1_Met-185 | 1.09 | 1.00 |
| P3_NM003-M161_CitricAcid-d4 | 0.97 | 1.00 |
| P3_NM002-M109_Glucose-13C6-d7 | 1.02 | 1.00 |
| P4_M0176_MalicAcid | 0.96 | 1.00 |
| P1_M0056_Pyridoxine | 1.15 | 1.00 |
| P4_M0148_UMP_p1 | 0.83 | 1.00 |
| P4_M0091_DCDP | 1.09 | 1.00 |
| P4_M0165_GeranylPyrophosphate | 1.18 | 1.00 |
| P4_M0097_DUMP | 0.88 | 1.00 |
| P4_M0157/M0156_Alpha-Keto-Glutarate/AdipicAcid | 1.06 | 1.00 |
| P4_NM003-M161_CitricAcid-d4_p1 | 1.02 | 1.00 |
| P4_M0140_Sucrose | 1.10 | 1.00 |
| P4_M0102/M0103/M0196_F16DiP/F26DiP/G16DiP_D241 | 1.07 | 1.00 |
| P1_M0007_Acetylcholine_p2_Met-146 | 1.06 | 1.00 |
| P1_M0013_Argininosuccinate | 1.08 | 1.00 |
| P4_M0158_AscorbicAcid | 0.96 | 1.00 |
| P1_M0052_Ornithine | 1.01 | 1.00 |
| P1_M0023_Creatinine | 1.03 | 1.00 |
| P3_M0126_LacticAcid | 0.99 | 1.00 |
| P1_M0012_Arginine | 1.01 | 1.00 |
| P3_M0104-M0107_F1P/F6P/G1P/G6P_D97 | 0.97 | 1.00 |
| P4_M0173_Kynurenine | 0.96 | 1.00 |
| P1_M0030_DimethylGlycine | 0.98 | 1.00 |
| P1_NM001-M68_Valine-d8 | 1.01 | 1.00 |
| P1_M0039_Homocysteine | 0.95 | 1.00 |
| P4_M0163_DHAP | 0.98 | 1.00 |
| P4_M0093_DCTP | 1.02 | 1.00 |
| P1_M0142_Thymidine | 0.97 | 1.00 |
| P1_M0201/M0202_ADMA/SDMA | 0.99 | 1.00 |
| P3_M0113_Glyceraldehyde | 1.00 | 1.00 |
| P4_M0185_Pyridoxal-5-phosphate_p1 | 1.01 | 1.00 |
| P1_M0018_Carnosine | 1.00 | 1.00 |

Figure 15A:
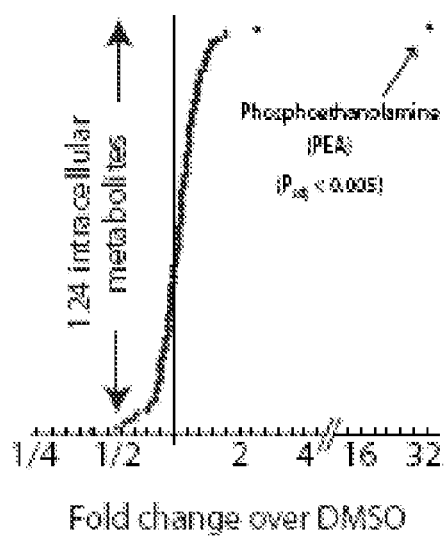
FIG. 15A presents exemplary data showing the fold-change in the intracellular concentration of 124 metabolites in MCH58 fibroblasts after six-hour exposure to 50 μM meclizine. Data expressed as fold change over DMSO treated cells (n=6).
Figure 15B:
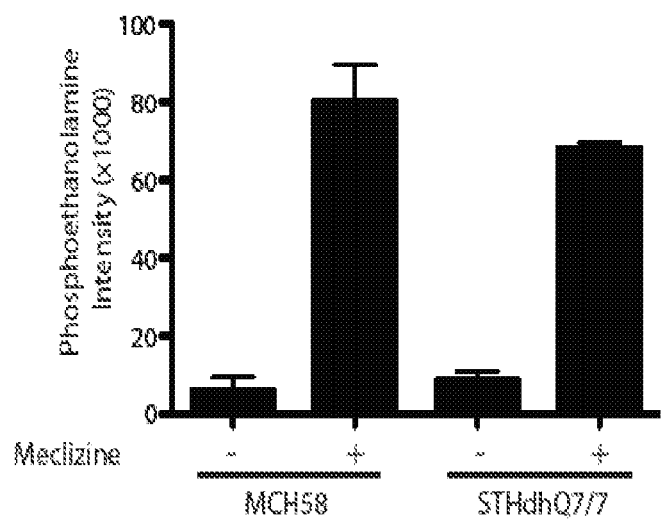
FIG. 15B presents exemplary data showing a relative quantitation of phosphoethanolamine by mass spectrometry. The relative quantitation of phosphoethanolamine (PEA) in MCH58 fibroblasts or mouse striatal cells (STHdhQ$^{7/7}$) treated with DMSO or 50 μM meclizine was carried out by triple quadrupole mass spectrometer. The metabolites from the cell extract were separated by HILIC, HPLC column and the PEA peak was verified by running PEA standard (Sigma P0503). (n=6 for fibroblasts; n=3 for striatal cells).
Figure 16A:
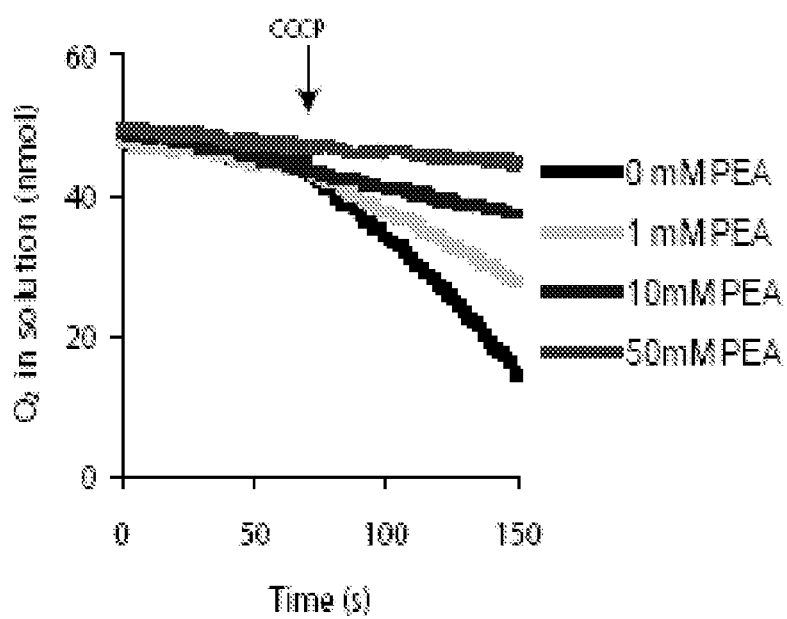
FIG. 16A presents exemplary data demonstrating that PEA suppresses uncoupled respiration in isolated mitochondria in a dose-dependent manner. The acute effect on oxygen consumption in isolated mitochondria were measured before and after CCCP administration, indicated by the arrow. Traces are representative of 3 independent measurements.
Figure 16B:
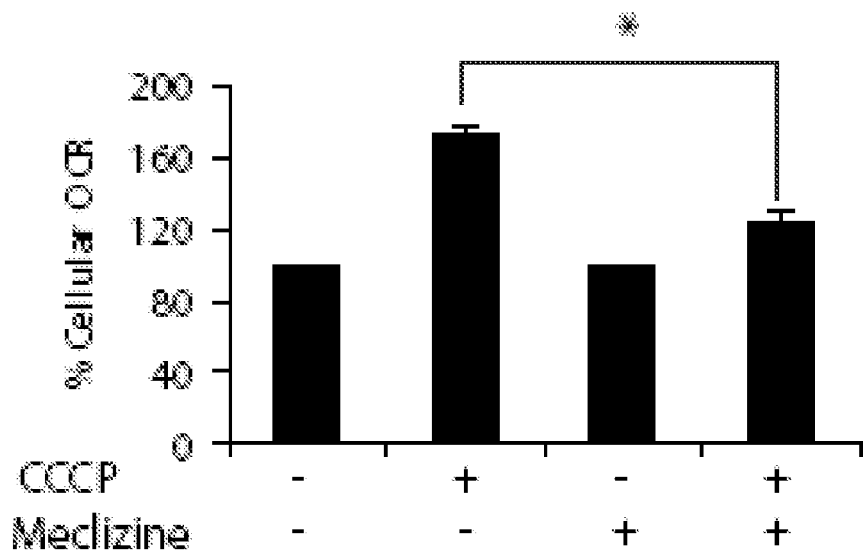
FIG. 16B presents exemplary data demonstrating that meclizine suppresses the increase in respiration in response to the uncoupler CCCP. 293 cells pre-treated with 25 μM meclizine for 6 hours fail to stimulate oxygen consumption to the same extent as DMSO treated controls after treatment with CCCP. Data expressed as mean±SD (n=3; *p value<0.01).

The most upregulated intracellular metabolite was phosphoethanolamine, which increased nearly 35-fold just six hours after treatment with meclizine. See FIG. 15A. The upregulation of phosphoethanolamine was confirmed by orthogonal chromatography, as well as via $^{31}$P-NMR. The upregulation of PEA was observed in multiple cell types. See FIG. 15B. Previous studies have shown that phosphoethanolamine can be elevated in tumor cells, and that ethanolamine and PEA can directly silence mitochondrial OXPHOS. Zhu et al., *J Lipid Res* 49: 2197 (2008); and Modica-Napolitano et al., *Biol Psychiatry* 55:273 (2004). To test the effect of phosphoethanolamine (PEA) on mitochondrial respiration, mitochondria were incubated with varying concentration of phosphoethanolamine for ~1 min prior to the addition of 2.5 mM glutamate and 2.5 mM malate followed by the addition of 1 µM CCCP. Consistent with these reports, PEA blocks uncoupler-stimulated respiration, and, in intact cells, meclizine treatment blunts uncoupler-stimulated respiration. See FIGS. 16A and 16B, respectively.

Figure 16C:
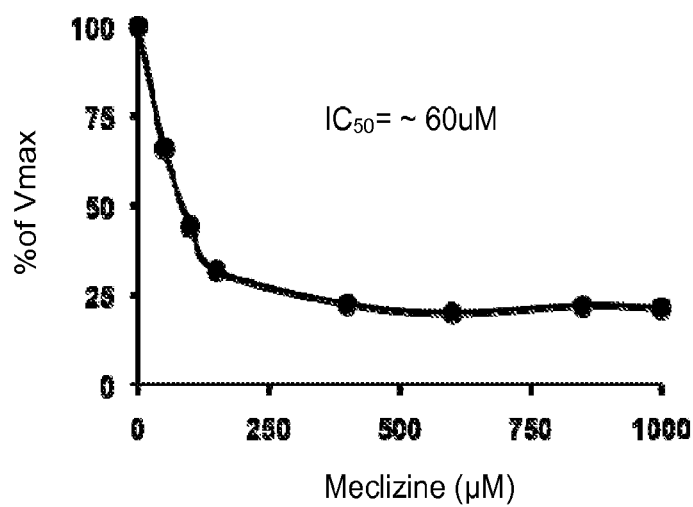
FIGS. 16 C-D are line graphs showing that PCYT2 (CTP: phosphoethanolamine cytidylyltransferase 2) is a target of meclizine (16C) and S-meclizine (16D). PCYT2 enzyme assays were carried out in vitro with purified recombinant PCYT2 in the presence of 50-1000 μM meclizine or 50-600 μM of S-meclizine.
Figure 16D:
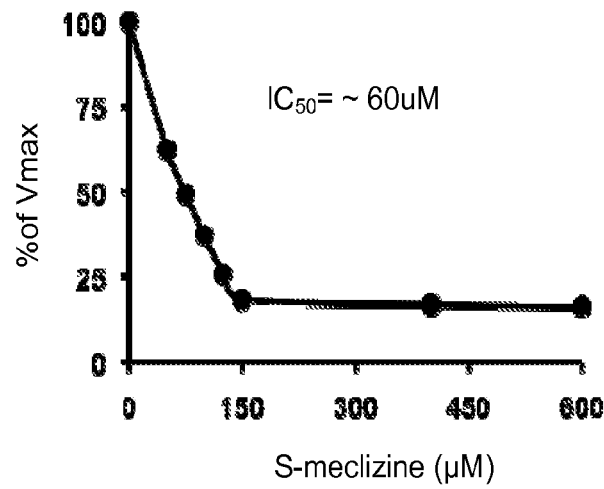

Phosphatidylethanolamine, an important inner membrane phospholipid mostly synthesized de novo via the PE-Kennedy pathway and by the decarboxylation of phosphatidylserine, is the most upregulated intracellular metabolite by meclizine, increasing nearly 35-fold just six hours after treatment with meclizine. CTP:Phosphoethanolamine Cytidylyltransferase (PCYT2) catalyzes the formation of CDP-ethanolamine, which is often the rate regulatory step in the PE-Kennedy pathway. See, e.g., Fullerton et al., J Biol Chem 18; 284(38):25704-13 (2009). To determine whether meclizine affects PCYT2 activity, PCYT2 (CTP:phosphoethanolamine cytidylyltransferase 2) enzyme assays were carried out in vitro with purified recombinant PCYT2 in the presence of 50-1000 µM meclizine or 50-600 µM of S-meclizine. For additional details see Zhu et al., J Lipid Res 49: 2197 (2008). As shown in FIGS. 16C-16D, meclizine and S-meclizine binD to, and inhibit, PCYT2, to cause an elevation in phosphoethanolamine and perhaps even ethanolamine.

Figure 17A:
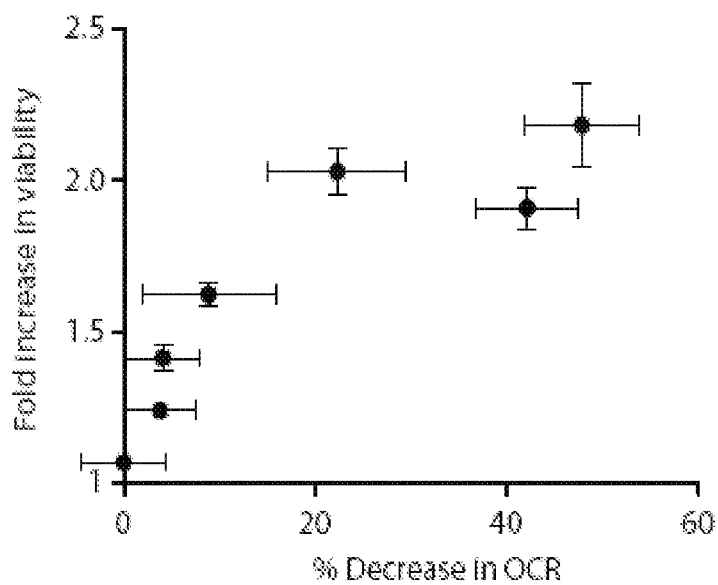
FIG. 17A presents exemplary data showing meclizine rescue of STHdh$^{Q111/111}$ viability is correlated with its effect on OXPHOS. The fold change in viability of STHdh$^{Q111/111}$ cells and the corresponding decrease in OCR for increasing concentration of meclizine is plotted (0, 5, 10, 12.5, 25, 37.5 and 50 μM). Data expressed as mean+/−SD (n≥3).
Figure 17B:
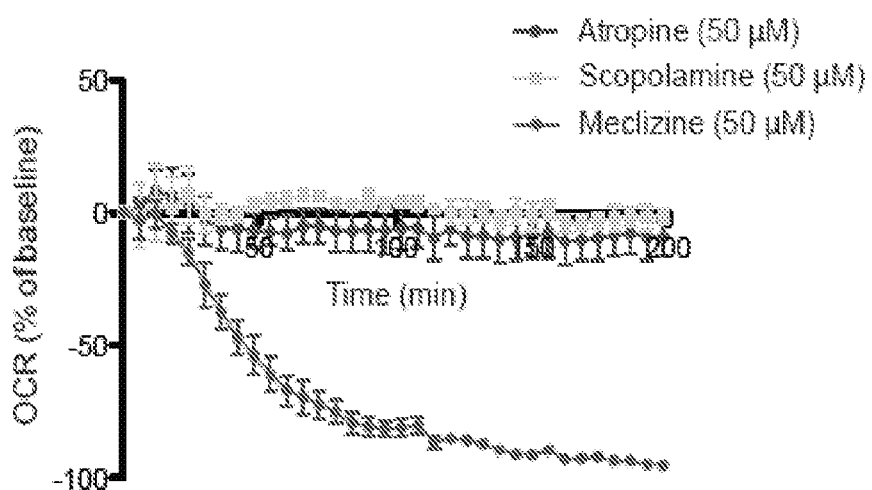
FIGS. 17B-C are line graphs showing the results of oxygen consumption rate (OCR) measurements carried out on 293 cells following the addition of 50 μM meclizine, 50 μM atropine, or 50 μM scopolamine (17B) and 50 μM meclizine, 50 μM pyrilamine, or 50 μM pheniramine (17C). Data are expressed as mean+/−SD (n≥3).
Figure 17C:
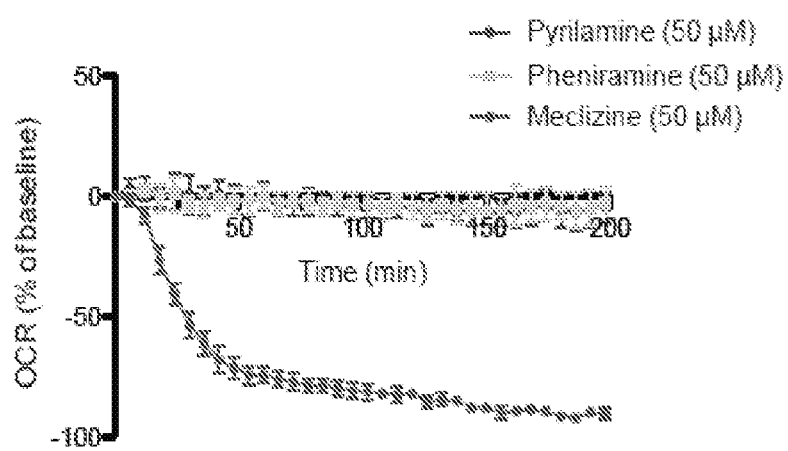

In contrast to canonical mitochondrial respiration inhibitors, meclizine has been shown herein to be an indirect inhibitor OXPHOS. For example, meclizine's effect can be titrated over a broad range of concentrations to achieve inhibition of cellular oxygen consumption rate by 10 to 60%. See FIG. 6A and FIG. 17A. Although it is not necessary to understand the mechanism of an invention, it is believed that the data herein suggests that meclizine is acting independent of the muscarinic or histamine receptor since drugs affecting these two receptor types did not influence energy metabolism; see FIGS. 17B-C.

Previous studies have shown that ethanolamine and phosphoethanolamine can serve as endogenous inhibitors of mitochondrial OXPHOS, and that these two metabolites are elevated in cancer. Modica-Napolitano et al., *Biol Psychiatry* 55:273 (2004); and Zhu et al., *J Lipid Res* 49:2197 (2008), respectively. Interestingly, both meclizine metabolites have been reported reduced in the brains of patients with Alzheimer's disease and Huntington's disease. See, e.g., Ellison et al., *Brain Res* 417:389 (1987). In addition, it is well known that the phospholipid composition of mitochondria influences supercomplex formation. As inhibition of PCYT2 would be expected to influence phospholipid composition within the cell, this may be another mechanism by which OXPHOS may be blunted.

Example 5

In Vivo Evaluation of Meclizine in Neurodegenerative Diseases

This Example describes experiments demonstrating that meclizine is effective in preventing cell death in cell models of neurodegenerative diseases. Several recent studies have shown that genetic or pharmacologic inhibition of mitochondrial respiration may suppress oxidative damage and cell death in neurodegeneration. Buttner et al., JBC 283:7554 (2008); Fukui et al., PNAS USA 104:14163 (2007); and Varma et al., *PNAS USA* 104:14252 (2007). While promising and innovative, a major limitation to translating these findings for therapeutic benefit, especially for CNS disorders, is the lack of OXPHOS inhibitors that cross the blood brain barrier and have a favorable therapeutic index. Classical inhibitors of mitochondrial respiration such as rotenone and oligomycin can suppress polyglutamine (polyQ) toxicity. Varma et al., PNAS USA 104:14252 (2007). However, due to their acute and direct inhibition of OXPHOS these agents are extremely toxic and unsuitable for therapeutic intervention.

Meclizine Protects Against Polyglutamine Toxicity

The above-described screening methods identified several candidate compounds that meet the criteria to be a clinical success in treating various diseases. One such candidate is meclizine. This drug was chosen for further testing as representative of the entire class of potential candidate drugs that may have therapeutic benefit without classic mitochondrial toxic side effects that result from most presently known OXPHOS inhibitors. For example, previous studies have shown that OXPHOS inhibitors including rotenone and oligomycin confer protection in cellular and animal models of Huntington's Disease (HD). Varma et al., *PNAS USA* 104:14252 (2007). However, these OXPHOS inhibitors are extremely toxic, and therefore cannot be used as therapeutics in humans. Meclizine was further explored for therapeutic potential in cellular and animal HD models because the compound has excellent CNS penetration, a broad therapeutic index, and inhibits mitochondrial respiration via gently reducing the OXPHOS substrate availability.

Recent studies in cellular and animal models have shown that genetic suppression of OXPHOS can actually suppress the toxicity of mutant alleles underlying a wide variety of neurodegenerative diseases. Huntington's disease is one such disorder that is due to a polyglutamine (polyQ) expansion in the protein product of the huntingtin gene. Gusella et al., *Nature* 306:234 (1983). One theory for disease pathogenesis is that polyQ interacts with the mitochondrial respiratory chain to increase oxidative damage and impair mitochondrial calcium handling. Previous studies have shown that classical inhibitors of mitochondrial respiration such as rotenone and oligomycin can suppress polyQ toxicity, though the agents used in these studies are not safe for use in humans. Varma et al., *PNAS USA* 104:14252 (2007).

a. Striatal Cell Culture Model

Conditionally immortalized striatal progenitor cells were obtained from HdhCAG knock-in mouse embryos that express human huntingtin with variable polyglutamine repeat lengths (e.g., 111 polyglutamine repeat lengths (STHdh$^{Q111/111}$), or 7 polyglutamine repeat lengths (STHdh$^{Q7/7}$). Trawl et al., *Hum Mol Genet* 9:2799 (2000). Mice with 111 repeats (STHdh$^{Q111/111}$) exhibit a HD-like phenotype, whereas mice expressing the shorter 7 repeat (Hdh$^{Q7/7}$) serve as a control and do not have this phenotype. Wheeler et al., *Hum Mol Genet*. 1(9):503 (2000). One cellular phenotype in the STHdh$^{Q111/111}$ mice comprises a rapid, apoptotic cell death following serum withdrawal that is much more pronounced than in wild-types cells (~218%). See FIGS. 5A, 5B, and 5D. Meclizine administration to STHdh$^{Q111/111}$ cells significantly increased cell survival (e.g., rescue) in a dose dependent manner (EC$_{50}$~17.3 µM) at 24 hours after removal of serum. See FIGS. 5A-5C. Although it is not necessary to understand the mechanism of an invention, it is believed that the observed cell survival may be due to suppressed apoptosis based on caspase 3 and 7 cleavage. See FIG. 5D. Improved cell viability was confirmed by microscopy. See FIG. 5G.

Because meclizine has multiple potential mechanisms of action (e.g., anti-histaminic, anti-muscarinic, or anti-OXPHOS) within the cell, the cell death mechanism by which meclizine confers striatal cell protection was investigated. Consequently, ten anti-histamines from six different classes, two classic anti-muscarinic compounds, and three OXPHOS inhibitors were evaluated.

Western blot analysis was performed as follows. Murine STH$^{Q111/111}$ striatal cells expressing mutant huntingtin protein were grown to ~75% confluency in 15 cm cell culture plate. Then serum containing medium was replaced with serum free media with either 0.1% DMSO or 50 µM meclizine and total protein was extracted at 0, 4, 10 and 24 hours post serum withdrawal and drug treatment in cell lysis buffer (Cell Signaling Cat No. 9803).

Protein concentration was determined using BCA protein assay kit (Thermo Scientific Cat No. 23227). SDS PAGE was performed using NuPAGE 4-12% Bis-Tris gel from Invitrogen (NP0321). 15 µg of protein was loaded per lane. Western blotting was performed as per the standard procedures. Cleaved Caspase 3 (Cat. No. 9661), Cleaved Caspase 7 (Cat. No. 9491), p-ERK (Thr220/Try204; Cat No. 9803), and AKT (Cat. No. 9803) antibodies were obtained from Cell Signaling. β-Actin antibody was purchased from Sigma (A1978).

The results demonstrate that meclizine prevented serum deprivation-induced activation of caspase 3 and caspase 7 for up to 24 hours after serum withdrawal. See FIG. 5D.

Meclizine's antagonism of H$_1$ and/or muscarinic receptors action were also examined in this striatal cell culture HD model. Meclizine conferred the most protection out of all these compounds, and that as a class, OXPHOS inhibitors provide the most protection, suggesting that meclizine-induced OXPHOS inhibition contributes to its neuroprotective effect. See FIG. 5E.

Moreover, a monotonic relationship in the dose response was observed between meclizine's ability to silence oxygen consumption in intact striatal cells and its ability to confer increased survival to cells expressing the mutant alleles. See FIG. 17A. Although it is not necessary to understand the mechanism of an invention, it is believed that these data suggest that meclizine's ability to protect murine striatal cells may be occurring via an ability to shift energy metabolism.

Figure 18A:
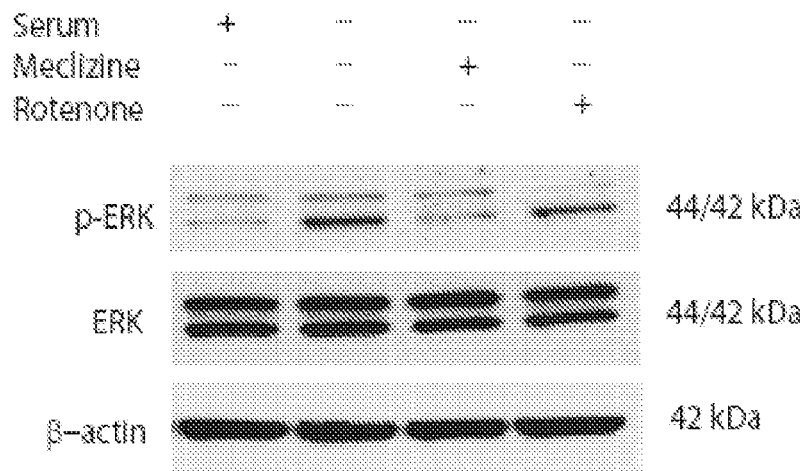
FIGS. 18A-B present exemplary data showing the effect of meclizine on ERK and AKT signaling pathways. Western blot analysis of protein extract from STHdh$^{Q111/111}$ striatal cells at 12 hours after removal of serum and exposure to DMSO, 50 μM meclizine or 33 μM rotenone. Commercially available antibodies were obtained from Cell Signaling that specifically detect phosphorylated ERK or phosphorylated AKT.
Figure 18B:
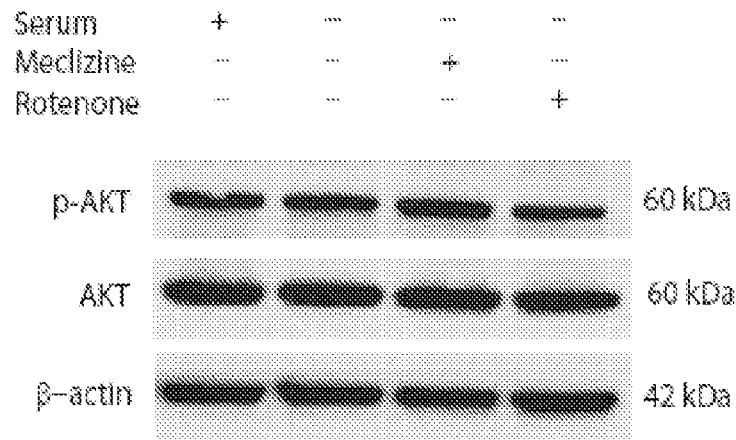

A previously reported study using a rat cell culture model of polyQ toxicity showed that the rescue of cell death by rotenone is partially mediated by the upregulation of pro-survival AKT and ERK signaling pathway. Varma et al., *Proc Natl Acad Sci USA* 104:14525 (2007). The data presented herein demonstrate rotenone rescue of murine STHd$^{Q111/111}$ cells from serum withdrawal induced apoptosis. See FIGS. 5D-5E. However, activation of ERK or AKT pathways with rotenone or meclizine was not demonstrated. See FIG. 18A and FIG. 18B.

Figure 5A:
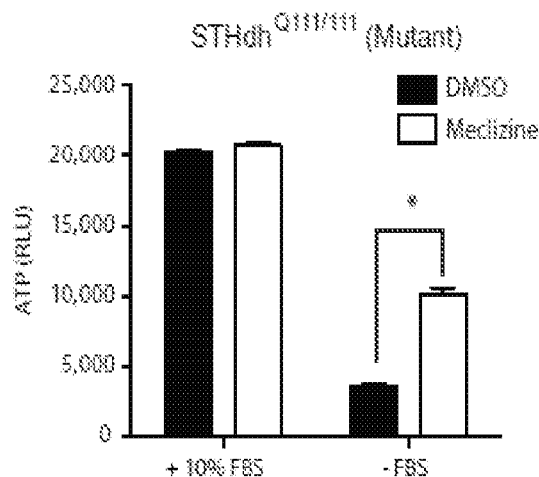
FIG. 5A presents exemplary data showing ATP levels in mutant STHdh$^{Q111/111}$ murine striatal cells expressing mutant huntingtin with and without removal of serum and exposure to 50 μM meclizine. Data expressed as mean±SD. * indicates p<0.01 by two-sided t-test (n=3).
Figure 5B:
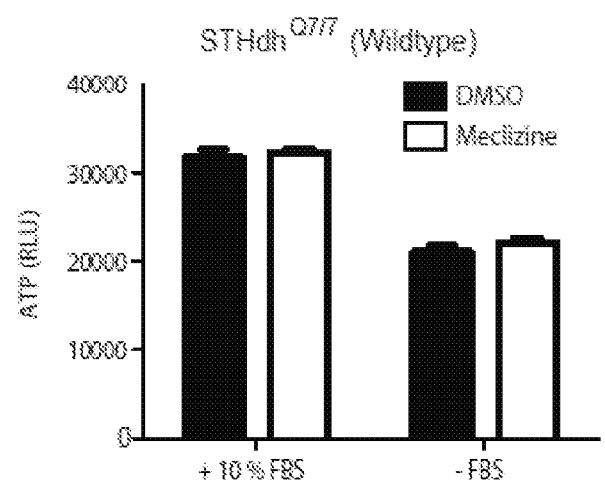
FIG. 5B presents exemplary data showing ATP levels in control STHdh$^{Q7/7}$ murine striatal cells expressing wild type huntingtin with and without removal of serum and exposure to 50 μM meclizine. Data expressed as mean±SD. * indicates p<0.01 by two-sided t-test (n=3).
Figure 5C:
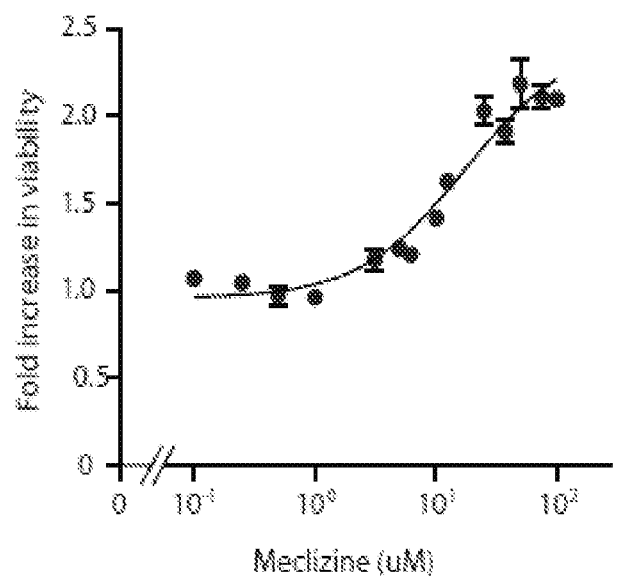
FIG. 5C presents exemplary data showing a meclizine dose-response on mutant HD cells viability. Cell viability was determined by CellTiter-Glo® assay and is expressed as fold change relative to DMSO treated cells. Solid line represents non-linear regression. Data expressed as mean±SD (n=3 per each data point)
Figure 5D:
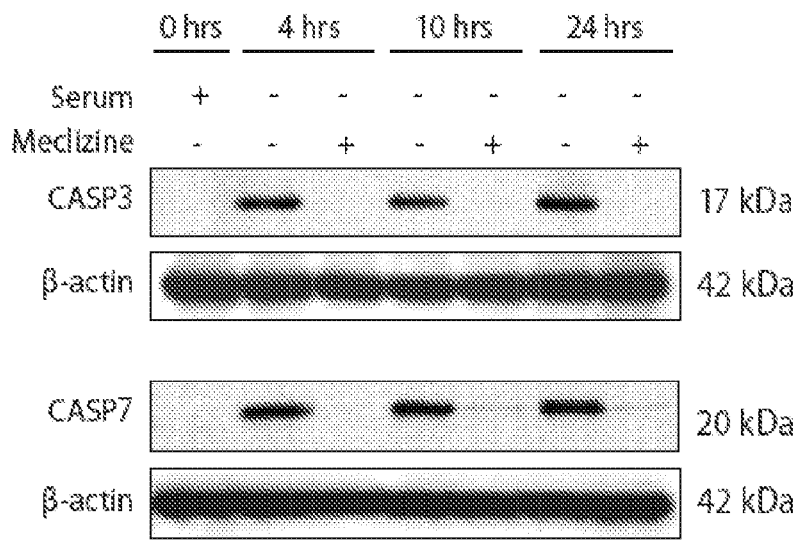
FIG. 5D presents exemplary data showing a Western blot analysis of protein extract from mutant HD cells at three time points after removal of serum and exposure to DMSO or 50 μM meclizine.
Figure 5E:
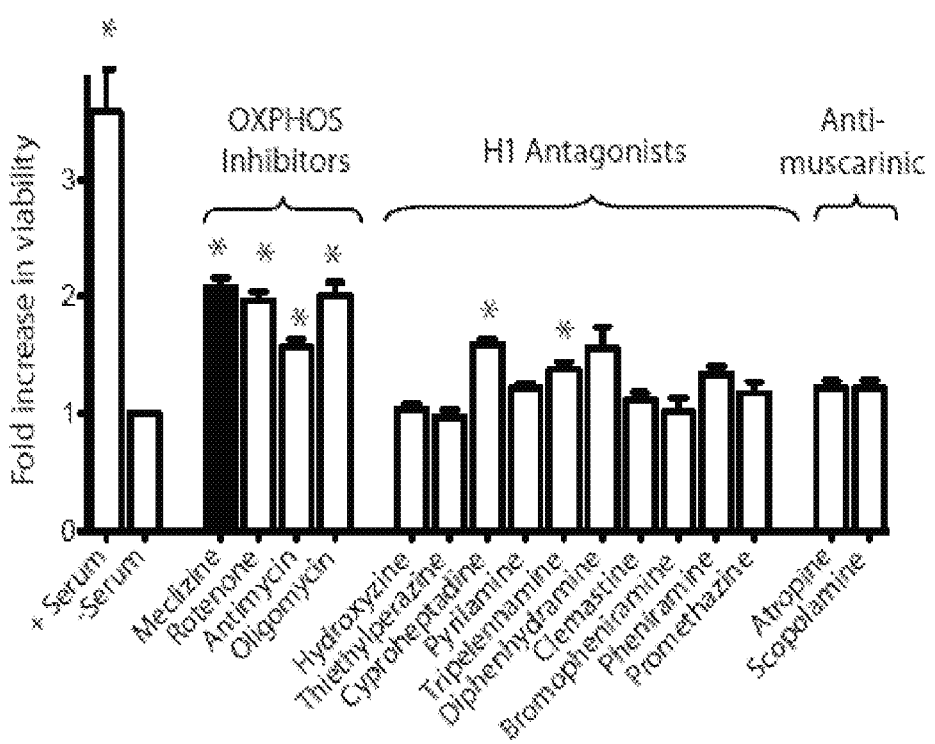
FIG. 5E presents exemplary data showing cell viability (CellTiter-Glo®) after incubation with sixteen (16) drugs versus DMSO. Compounds are organized by pharmacologic target. Serum treatment was used as a positive control. Data expressed as mean±SD (n=3 per drug).

And as shown in FIGS. 5A-B, Meclizine is protective against polyglutamine toxicity in cellular model of Huntington's disease. This protection correlates with its ability to inhibit cellular respiration (see FIG. 17A) and is independent of its anti-histamine and anti-muscarinic activity (see FIG. 5E). This was evaluated by detecting changes in viability of STHdhQ111/111 cells following serum withdrawal and with drug treatments. Compounds are organized by pharmacologic target. Serum treatment was used as a positive control.

Figure 18C:
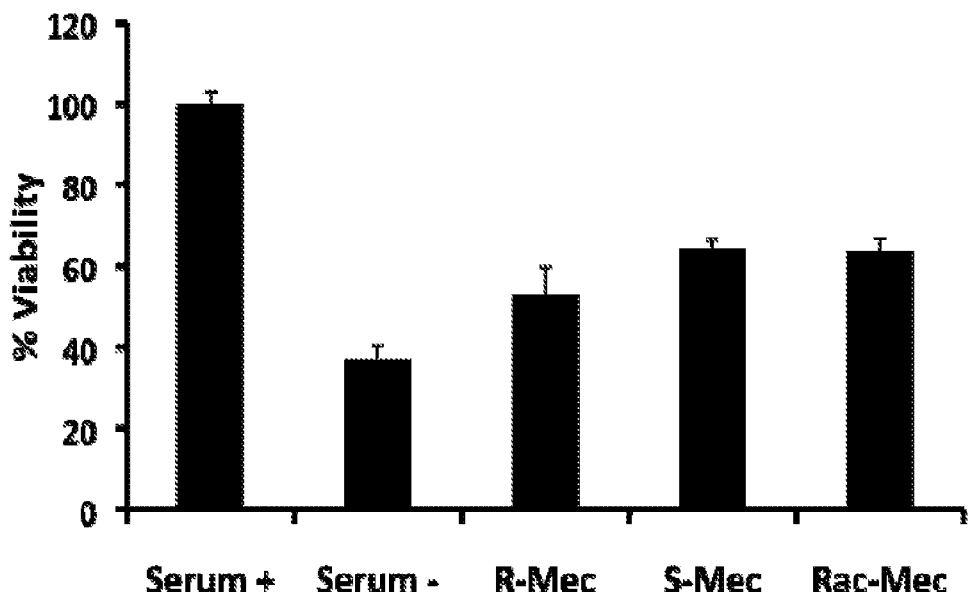
FIG. 18C is a bar graph showing the percent change in viability of STHdhQ111/111 cells following serum withdrawal and with drug treatment. R-meclizine (R-Mec), S-meclizine (S-Mec) and racemic mixture (Rac-Mec) were used at 20 μM. Serum treatment was used as a positive control. Data are expressed as mean+/−SD (n=4 per drug).

The ability of the two enantiomers of meclizine to provide protection was also evaluated. The percent change in viability of STHdhQ111/111 cells was determined following serum withdrawal and with drug treatment. R-meclizine (R-Mec), S-meclizine (S-Mec) and racemic mixture (Rac-Mec) were used at 20 µM. Serum treatment was used as a positive control. As shown in FIG. 18C, S-meclizine is protective in cellular model of Huntington's disease.

The mechanism by which meclizine serves as an anti-emetic or anti-vertigo agent is not precisely known, but it is believed to function via blockade of the histamine and muscarinic receptor. The above cell-based bioenergetic analyses suggest that meclizine switches metabolism from oxidative phosphorylation to glycolysis over a period of hours, likely via a novel post-transcriptional mechanism independent of histamine and muscarinic cell surface receptors. For example, the $K_m$ with which meclizine switches energy metabolism is about a hundred fold higher than the published $K_m$ for blocking $H_1$ receptors.

b. Transgenic *C. elegans* Model

Meclizine was also tested in an animal model of Huntington's disease. Transgenic *C. elegans* touch receptor neurons express an N-terminal fragment of huntingtin (htt) comprising 128 glutamine repeats, as opposed to seventeen glutamine repeats in the wild type protein. These neurons show polyQ-dependent neuronal dysfunction resulting in defective posterior mechanosensation. Parker et al., *Nat Genet* 37:349 (2005) Animals co-expressing YFP and N-terminal htt fused to CFP in touch receptor neurons were used for drug testing. See, eg., Parker et al., *Proc Natl Acad Sci USA* 98:13318 (2001). Synchronized L1 larvae, obtained by hypochlorite extraction, were incubated with drugs in 96 wells plates in 50 µl M9 medium with OP-50 bacteria and 30 mg/ml streptomycin, at 20° C. during 3 days as previously described. Three independent assays were performed and a minimum of 100 worms were tested per dose.

Worms were treated with DMSO or 33 µM meclizine for 3 days. Animals were considered as touch responsive if they reacted after light touch (e.g., by initiating a backward movement). Out of 3 touches, 2 or 3 reactions were regarded as responsive, and 0 or 1 reaction was regarded as unresponsive. Htt aggregation and axonal morphology in PLM neurons were scored using light microscopy as previously described (Parker et al., Proc Natl Acad Sci USA 98:13318 (2001)). Htt aggregation was scored using CFP fluorescence, axonal dystrophy was quantified using YFP fluorescence to detect axonal swelling.

Proteins were extracted using WormBook method separated on 4-15% bis-tris gel, transferred to membrane and the GFP tagged 128Q-htt fragment was probed using anti-GFP antibody (AbCam ab6556). Protein quantity was normalized using an anti-actin antibody (MP Biochemicals 69100).

Figure 5F:
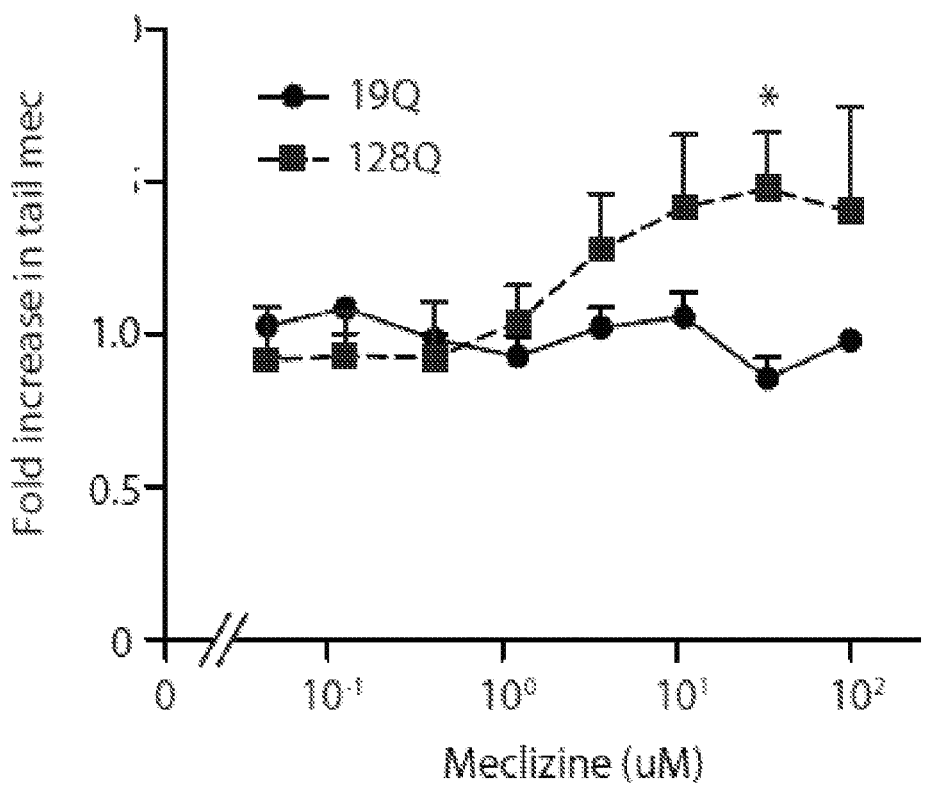
FIG. 5F presents exemplary data showing dose-response curves for percent rescue of tail Mec by meclizine in worms expressing control 19Q or 128Q.
Figure 5G:
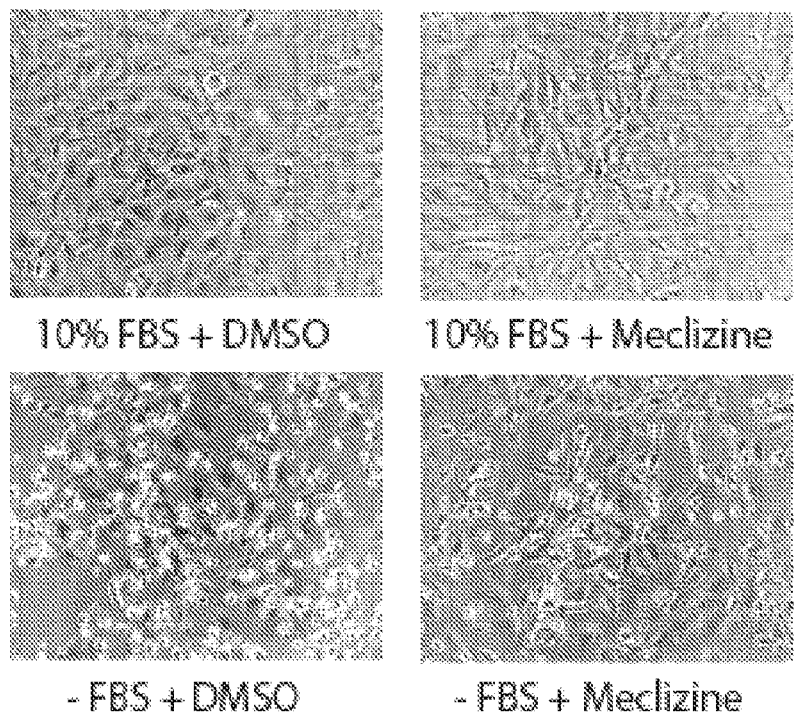
FIG. 5G presents exemplary photomicrograph (20×) brightfield images of mutant STHdh$^{Q111/111}$ striatal cells with and without serum and co-treatment with 50 μM meclizine for 24 hours.
Figure 19A:
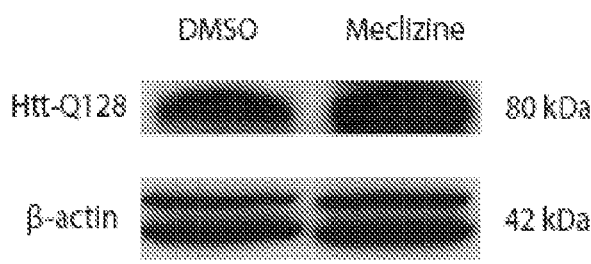
FIGS. 19A-B present exemplary data showing the effect of meclizine (33 μM) on Htt-Q128 protein expression in two Huntington Disease models. Htt-Q128 was detected using mouse anti-human HD antibodies. Control: DMSO.
Figure 20:
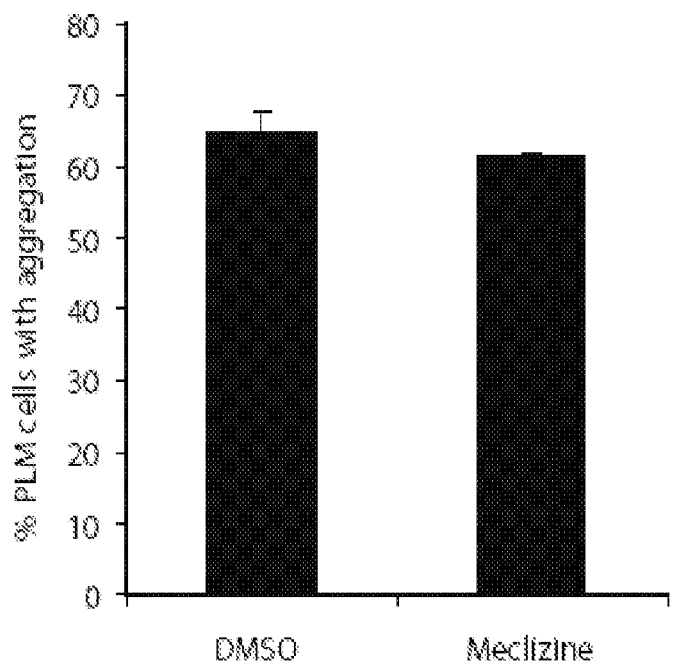
FIG. 20 presents exemplary data showing the effect of meclizine on protein aggregation in PLM neurons of Q128 expressing *C. elegans*. Htt-Q128 aggregates formation was detected by light microscopy following 33 μM meclizine treatment. At least 180 PLM neurons were scored in 80 worms (n=3).
Figure 21A:
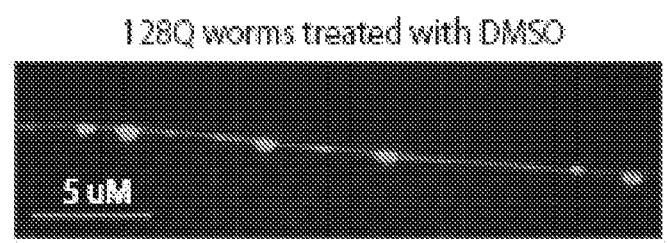
FIG. 21A presents exemplary data showing fluorescent images of the effect of DMSO or 33 μM meclizine on axonal dystrophy of 128Q *C. elegans*. Scale bars indicate 5 μm.
Figure 21A:
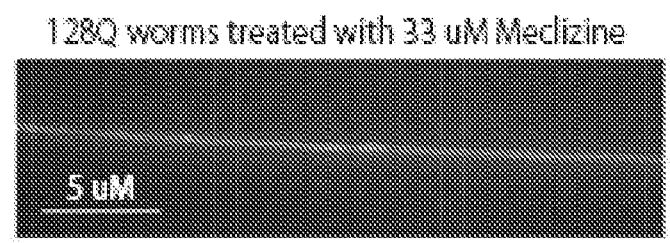
Figure 21B:
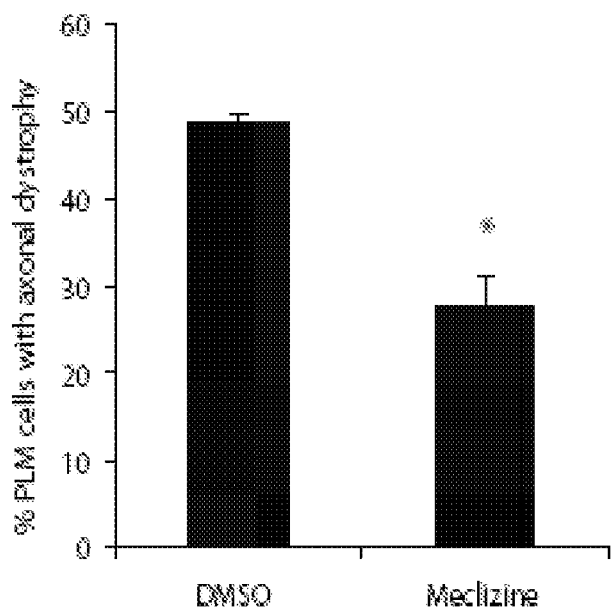
FIG. 21B presents exemplary data showing the effect of meclizine on axonal swelling in PLM neurons of 128Q expressing *C. elegans*. Axonal swelling in PLM neurons of Htt-Q128 expressing worms is observed by light microscopy following DMSO or 33 μM meclizine treatment. At least 180 PLM neurons were scored in 80 worms (n=3, *P<0.01).

Meclizine improved the sensory response to tail poke in a dose dependent manner in mutant PolyQ animals with no effect detected in control animals. See FIG. 5F. An optimal response of 33.33 µM concentration was observed, which is comparable to cell viability studies in murine STHdh$^{Q111/111}$ cells. See FIG. 5C. At the 33.33 µM dose, no changes were observed in transgenic protein expression. See FIG. 19A. Similarly, no effects on PolyQ protein aggregation were detected. See FIG. 20. However, axonal swelling was reduced. See FIG. 21A and FIG. 21B. This data is consistent with previous reports that in PolyQ-expressing worms, axonal dystrophy is a stronger correlate of neuronal dysfunction. Parker et al., *Proc Natl Acad Sci USA* 98:13318 (2001).

Meclizine did not produce any toxicity at 33.33 µM, although 100 µM resulting in a mild developmental delay. In contrast, rotenone has been shown to cause strong developmental delay with severe toxicity at even lower doses. Varma et al., *Proc Natl Acad Sci USA* 104:14525 (2007).

c. Transgenic *Drosophilia melanogaster* Model

Meclizine was also tested in a transgenic insect model of Huntington's disease in which the first 548 amino acids of human Htt (containing 128 glutamines) was expressed in the eyes of *Drosophila melanogaster*. The UAS-Htt-Q0 and UAS-Htt-Q128 lines encoding the first 548 amino acids of human Htt containing either 0 or 128 glutamines, respectively (7), were gifts from Troy Littleton. The elav-GAL4 driver was from the Bloomington Stock Center (#8765). The UAS-Htt-Q128 line was crossed to elav-GAL4/CyO to obtain UASHtt-Q128/elav-GAL4 flies.

Figure 22A:
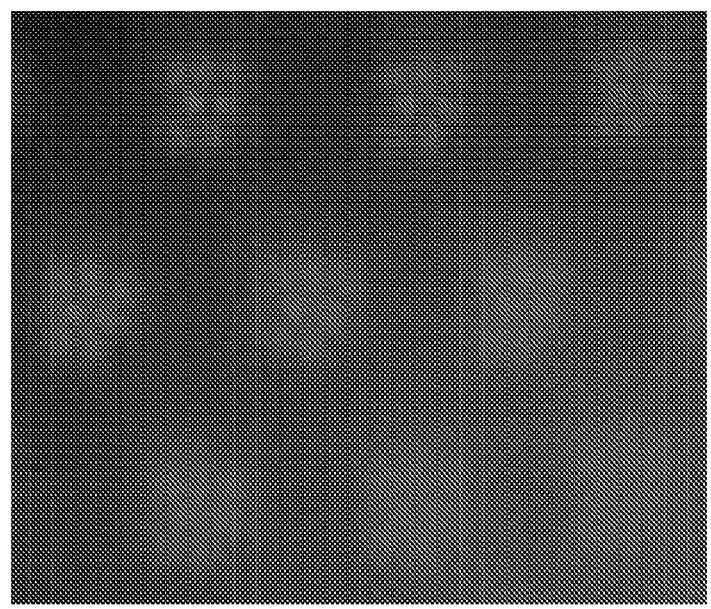
FIG. 22A shows flies expressing mutant Htt-Q128 (elav-GAL4>UAS-Htt-Q128) having a normal complement of seven visible light collecting units (rhabdomeres) per ommatidium at eclosion.
Figure 22B:
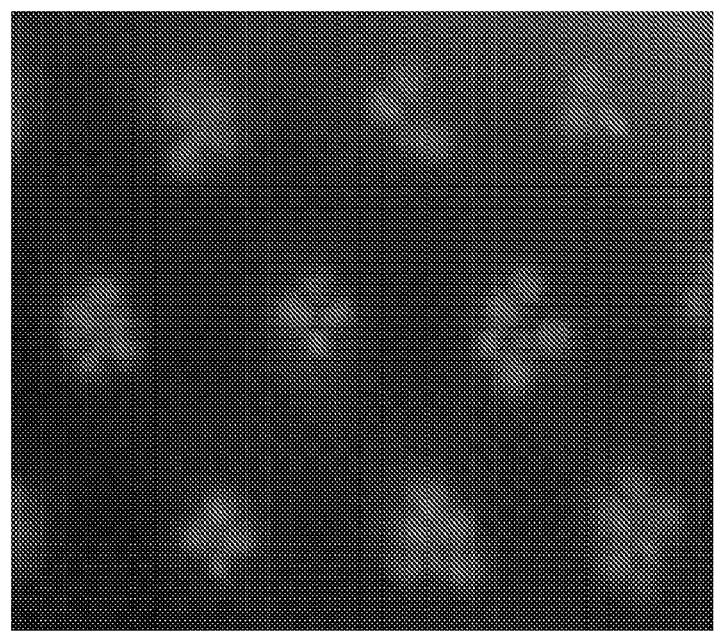
FIG. 22B shows flies expressing mutant Htt-Q128 (elav-GAL4>UAS-Htt-Q128) having progressive degeneration and reduction of the number of rhabdomeres at ten (10) days post-eclosion.

These adults showed no discernable degeneration by pseudopupil analysis upon eclosion, but these rhabdomeres underwent progressive degeneration over the following 10 days. See FIG. 22B. In contrast, UAS-Htt Q0 driven by elav-GAL4 did not show degeneration during this time.

Equal numbers of newly enclosed UAS-Htt-Q128/elav-GAL4 flies were added to vials containing Carolina Biological Instant Fly food that had been freshly made up with water and meclizine or DMSO vehicle at different concentrations (100, 33, 11 or 3 µM). Flies were changed to fresh food and drug every 2 days and were maintained at 25° C. throughout the experiment. Neurodegeneration was assessed using the pseudopupil technique at day 10 by scoring the rhabdomere number/ommatidium from at least 8 animals for each condition; see Jackson et al., Neuron 21:633 (1998). The experiment was performed twice and scoring was conducted in a blinded manner. Western blot analysis using mouse anti-human HD (mAb2216 from Chemicon, Temecula, Calif.) was performed using lysates from UAS-Htt-Q128/elav-GAL4 adult flies that had been fed on either meclizine or DMSO at 33 µM for 10 days.

Figure 19B:
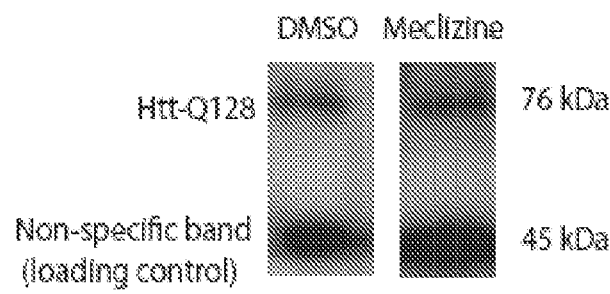
Figure 23:
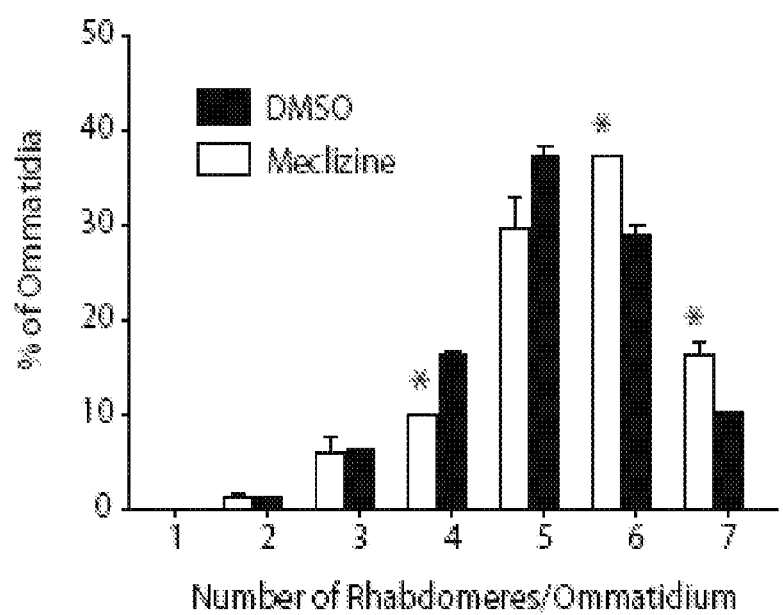
FIG. 23 presents exemplary data showing that meclizine rescues neuronal loss in an in vivo HD model in *Drosophila melanogaster*. Transgenic human HD-Q128 driven in neurons using elav-GAL4 resulted in a time-dependent neurodegeneration as assessed by the number of visible rhabdomeres. Flies were treated with DMSO vehicle or meclizine at 33 μM for 10 days and the average number of rhabdomeres per ommatidium was calculated and is shown as a distribution. Data expressed as mean±SD (n=2, *p<0.05).

The expression of mutant Htt transgene causes a progressive decrease in the number of rhabdomeres per ommatidium. See FIG. 22A and FIG. 22B. Treatment with 33 µM meclizine did not influence transgenic protein expression. See FIG. 19B. However, the same meclizine treatment did protect against rhabdomere loss as compared to DMSO treated controls. See FIG. 23.

Example 6

In Vivo Evaluation of Meclizine in Ischemic Disorders

The data herein shows that meclizine provides protection in an art-accepted cellular model of ischemia and reperfusion.

Figure 25A:
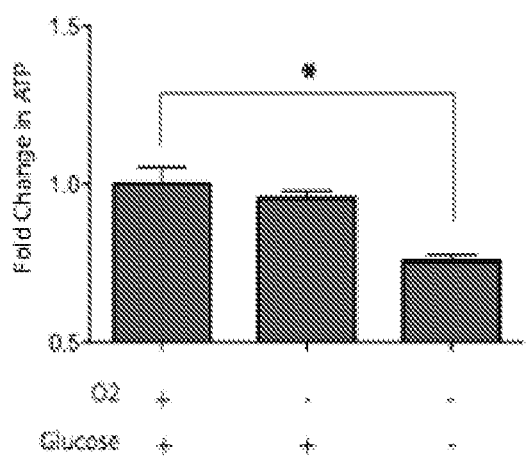
FIGS. 25A-B present exemplary data showing the protective effects of meclizine in in vitro ischemia reperfusion injury in striatal cells. Data are represented as mean+/−SD, n≥3. * indicates p<0.01 by two-sided t-test. Meclizine was dissolved in 10% Cremaphor EL solution (Sigma No. C5135) in PBS and was adjusted to neutral pH with NaOH.
Figure 25B:
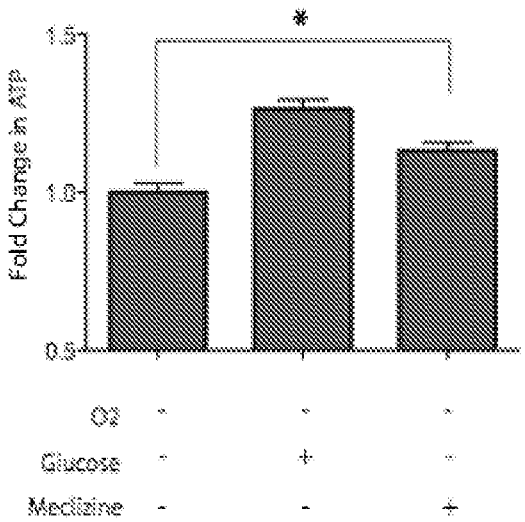
Figure 33A:
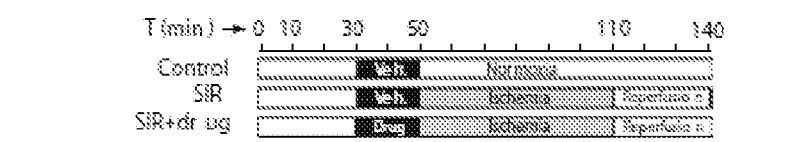
Figure 33A:
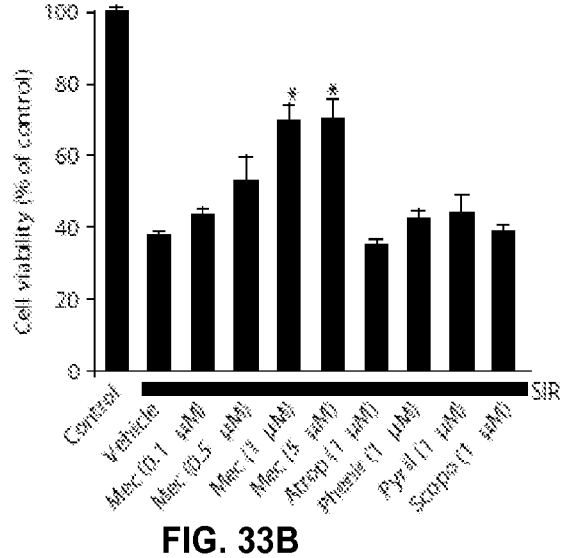
Figure 33A:
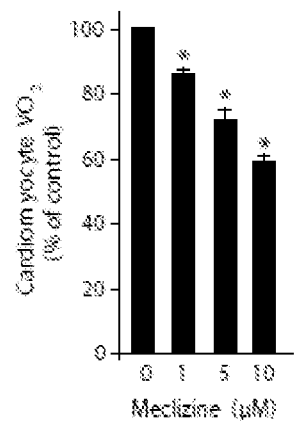

Immortalized mouse striatal 20A5 cells grown in DMEM with 10% dialyzed fetal bovine serum were exposed to oxygen and glucose deprivation for 18 hours followed by 12 hours of recovery in normoxia with full media. This IR model induces roughly 30% decrease in cell viability as measured by the ATP luminescence assay CellTiter-GLO. See FIG. 25A. Cells were then pretreated with 25 µM meclizine for 8 hours prior to oxygen and glucose deprivation, wherein the meclizine pretreatment resulted in a significant improvement in cell viability over corresponding vehicle pre-treated cells. See FIG. 25B The ability of meclizine to protect isolated cardiomyocytes and isolated hearts from ischemic injury was investigated as follows Adult rat ventricular cardiomyocytes were isolated by endotoxin-free collagenase perfusion, and the simulated ischemia-reperfusion injury was performed as previously described (Wojtovich and Brookes, Basic Res. Cardiol., 104: 121-129 (2009)). Isolated cardiomyocytes were cultured before being subjected to the treatments shown in FIG. 33A. Control cells were exposed to DMSO for 20 minutes. Test cells were exposed to either vehicle or doses of meclizine for 20 minutes, which was washed out before being subjected to ischemia for 60 minutes followed by reperfusion for 30 minutes under normoxic conditions in normoxic glucose-replete buffer at pH 7.4. Cell viability was assayed by Trypan blue exclusion. VO2 was assessed by isolating mitochondria and measuring both respirating cells and mitochondria using a Clark oxygen electrode (Wojtovich, supra).

As shown in FIG. 33B, about a 60% decrease in cell viability was observed in DMSO treated cells subjected to ischemia/reperfusion (I/R) whereas meclizine protected cardiomyocytes against I/R at various concentrations. Optimal protection was observed from 0.5 µM-10 µM meclizine. Meclizine protection was not observed at concentrations of 50 µM and 100 µM. Protection was not observed for other antihistamines (pyrilamine and pheniramine) or antimuscarinic agents (scopolamine and atropine).

As shown in FIG. 33C, meclizine treatment promoted a decrease in $VO_2$ compared to DMSO treated cells. These observations support that meclizine can be used to protect against I/R in cardiomyocytes.

Figure 34A:
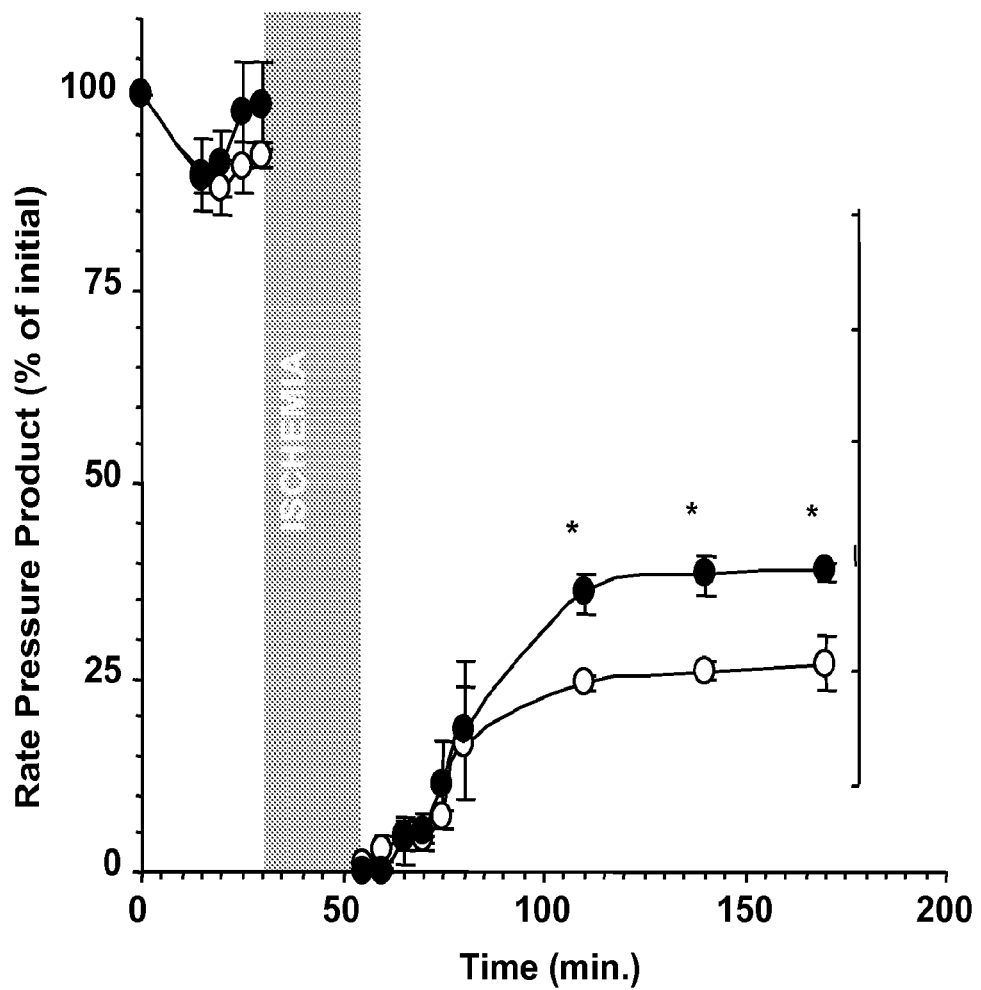
FIGS. 34A-B include data showing the protective effect of meclizine in isolated hearts.
Figure 34B:
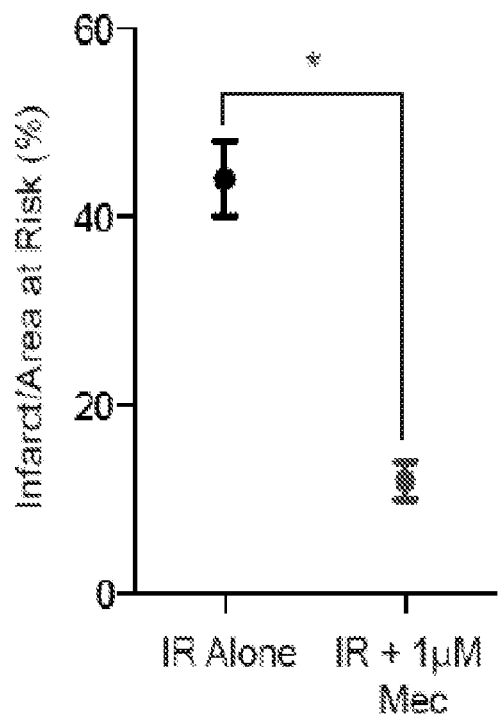

The effect of meclizine in isolated, ex vivo, hearts was assessed using retrograde-perfused hearts and the Langendorf heart (Nadtochiy et al., Biochem. J., 395:611-618 (2006)). Hearts were then subjected to a period of ischemia followed by reperfusion. As shown in FIGS. 34A and 34B, meclizine protected treated hearts against I/R damage compared to the untreated controls as shown by an increase in rate pressure (see FIG. 34A) and smaller infarct size (see FIG. 34B).

These observations further the observation noted in isolated cardiomyocytes and support that meclizine can be used to protect against FR in intact and functioning hearts.

The protective effect of meclizine for stroke was assessed using an art-recognized animal models of stroke, as follows.

Plasma concentrations of meclizine were determined after intraperitoneal injections in C57BL/6 mice. Injections of 100 mg/kg meclizine or vehicle control were followed by cardiac puncture blood draws at 1 h or 6 h. Absolute concentrations of meclizine in plasma were measured using liquid chromatography tandem mass spectrometry against a purified standard. To check the protective effect of the tested compounds, male C57BL/6 mice were treated with two intraperitoneal injections of 100 mg/kg meclizine, 20 mg/kg pyrilamine and 0.5 mg/kg scopolamine or vehicle, at 17 and 3 hours before ischemia. Drug doses for pyrilamine and scopolamine were chosen based on previous literature evidence of in vivo brain bioavailability (see, e.g., Miyazaki et al., Life Sci 57:2137 (1995) and Toyota, et al., Mol. Pharmacol 62:389 (2002)). The experimenter was blinded to treatment groups. Mice were anesthetized with isoflurane (2.5% induction, 1.5% maintenance, in 70% N2O/30% O2), and subjected to 1 h transient middle cerebral artery occlusion using an intraluminal filament inserted through the external carotid artery. Regional cerebral blood flow was monitored using a laser Doppler probe placed over the core middle cerebral artery territory. Rectal temperature was controlled at 37° C. by a servo-controlled heating pad. Total infarct volume was calculated on 2,3,5-triphenyltetrazolium chloride (TTC)-stained 1-mm thick coronal sections by integrating the infarct areas in each of ten slice levels. Infarct volume was calculated using the 'indirect method', that is, contralateral hemisphere minus ipsilateral non-infarcted volume. Data were expressed as mean±s.d. One-way ANOVA followed by Tukey's multiple comparison test was used for analysis of values between groups. Neurological deficit scores were analyzed by Kruskal-Wallis nonparametric ANOVA followed by Dunn's multiple comparisons test. P<0.05 was considered statistically significant.

Figure 35A:
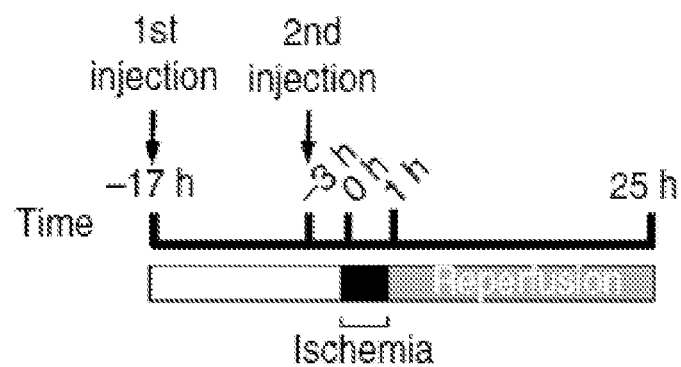
FIGS. 35A-35C include data showing the protective effect of meclizine in a stroke animal model. 35A, Protocol for the murine model of stroke. Male C57BL/6 mice were treated with two intraperitoneal injections of 100 mg/kg meclizine, 20 mg/kg pyrilamine and 0.5 mg/kg scopolamine or vehicle at 17 h and 3 h before 1 h transient middle cerebral artery occlusion followed by 24 h of reperfusion. 35B, Infarct volume measured on TTC-stained 1-mm thick coronal slices obtained from mice treated with meclizine, scopolamine, pyrilamine or vehicle. Data points refer to independent experiments, and the solid line represents their mean. (*$P<0.05$ versus vehicle and scopolamine, $P<0.01$ versus pyrilamine; one-way ANOVA followed by Tukey's multiple comparison test). 35C Cerebral blood flow (CBF) measured at baseline and after occlusion of the common carotid artery (CCA) and middle cerebral artery (MCA) upon treatment with meclizine, scopolamine, pyrilamine or vehicle. Data represent mean±s.d.

Animals were subjected to ischemia for one hour using MCA occlusion followed by 24 hours of reperfusion; meclizine or vehicle control were administered prior to ischemia (see FIG. 35A).

Figure 35B:
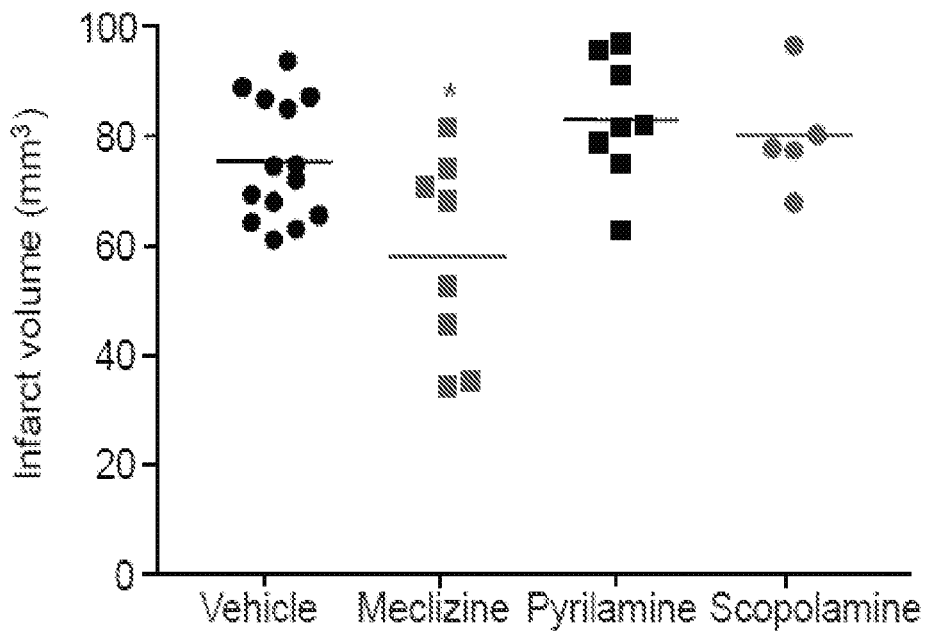
Figure 35C:
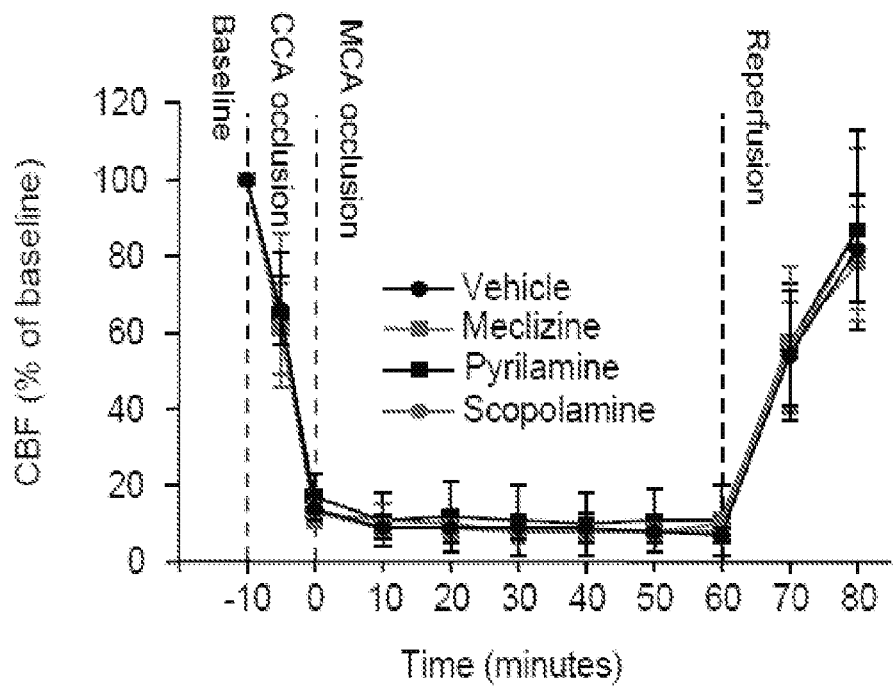
Figure 35D:
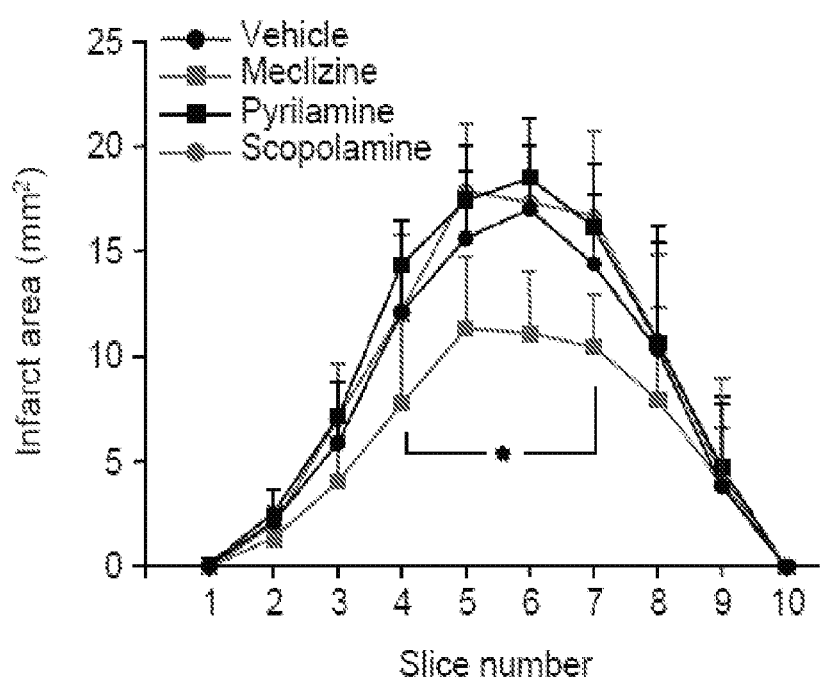
FIG. 35D is a line graph showing changes in infarct area in the rostrocaudal extent of the brain (slice 1-10) upon treatment with meclizine, scopolamine, pyrilamine or vehicle. Data points represent the mean area of infarction in individual slice levels±s.d. in mm2 (n=14 for vehicle, n=8 for meclizine, n=8 for pyrilamine, n=5 for scopolamine, *$P<0.05$).

As shown in FIGS. 35B and 35D, infarct volume was significantly lower in meclizine-treated animals compared to control animals, while CBF did not differ significantly (FIG. 35C).

These observations support that meclizine can be used to protect against stroke.

Together, the results presented herein support that meclizine can be used to protect against cellular injury promoted by ischemia-reperfusion in the heart, brain (central nervous system), and kidneys.

Example 7

Meclizine and Diabetes

The data provided herein shows that meclizine can be used for the treatment of diabetes.

Fully differentiated C2C12 myotubes were subjected to a glucose uptake protocol, as follows. Briefly, C2C12 myotube cells were incubated for four hours in serum-free media containing either 0.1% DMSO as a control, 50 micromolar meclizine, 50 micromolar S-meclizine, or 2 mM metformin. Cells were subsequently incubated for thirty minutes in serum and glucose free buffer and then transitioned to buffer containing [3H]-2-deoxyglucose for five minutes. After multiple wash steps, cells were lysed and the lysate was subjected to scintillation counting to quantify uptake. Data were prepared as raw counts per minute, which is proportional to 2-deoxyglucose uptake.

Figure 36:
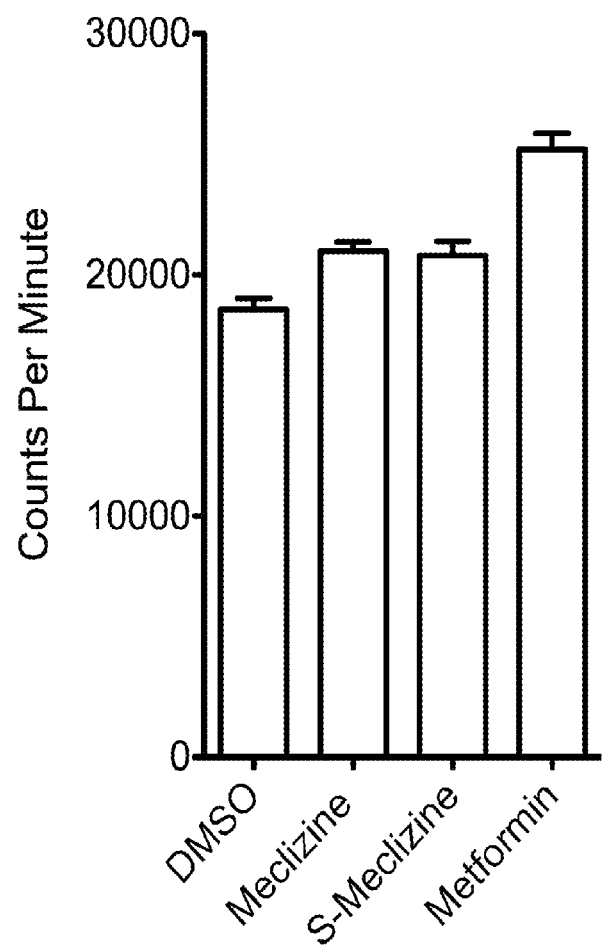
FIG. 36 is a bar graph showing basal glucose uptake measured as counts per minute in vehicle, meclizine, S-meclizine, and metformin treated C2C12 myotubes.

As shown in FIG. 36, meclizine and S-meclizine promoted increased basal glucose uptake in C2C12 myotubes. In addition, meclizine and S-meclizine also activate AMP Kinase, as shown in FIG. 24C.

The cellular studies demonstrate the glucose lowering effects of meclizine and S-meclizine. In addition, meclizine and S-meclizine are capable of activating AMPK. Collectively, these data support the therapeutic potential of meclizine and S-meclizine in diabetes.

Example 8

Meclizine and Parasitic Infections

The data provided herein shows that meclizine can be used for the treatment of infections with certain parasites.

Phosphatidylethanolamine is a major phospholipid class in all eukaryotic cells. Phosphatidylethanolamine can be synthesized by (i) the CDP-ethanolamine branch of the Kennedy pathway; (ii) decarboxylation of phosphatidylserine; or (iii) base exchange with phosphatidylserine. In mammals including humans, all three pathways are available. However, in certain pathogens including *Trypanosoma brucei*, the causative agent of human and animal African Trypanosomiasis (sleeping sickness), *Trypanosoma cruzi*, a parasite that causes Chagas disease, and *Plasmodium falciparum*, the human malaria parasite, phosphatidylethanolamine is predominantly synthesized via the Kennedy pathway. Thus, it was hypothesized that meclizine would be effective in killing these parasites.

As shown in Table 5, Meclizine, R-meclizine and S-meclizine kills *Trypanosoma brucei* with an ED50 in low micro-molar range.

TABLE 5

Effectiveness agains *Trypanosoma brucei*

| Compound | ED50 |
| --- | --- |
| Meclizine | 1.41 ± 0.12 μM |
| R-meclizine | 0.66 ± 0.05 μM |
| S-meclizine | 3.43 ± 0.23 μM |

Other Embodiments

It is to be understood that while the invention has been described in conjunction with the detailed description thereof, the foregoing description is intended to illustrate and not limit the scope of the invention, which is defined by the scope of the appended claims Other aspects, advantages, and modifications are within the scope of the following claims.

---

What is claimed is:

1. A method for reducing organ damage, or the risk of organ damage, resulting from myocardial ischemia, cerebral ischemia, or renal ischemia, the method comprising administering a therapeutically effective amount of an S-enantiomer of meclizine, substantially free of the R-enantiomer of meclizine, to a subject in need thereof.

2. The method of claim 1, wherein the cerebral ischemia is a result of a stroke.

3. The method of claim 1, wherein the S-meclizine is administered in a dose sufficient to produce a serum level of about 1 µM, or a peak serum concentration of at least 1 µM.

4. The method of claim 1, wherein the S-meclizine is formulated for parenteral administration.

5. The method of claim 1, wherein the S-meclizine is administered in a daily dose of about 250 to 1000 mg/day.

6. The method of claim 1, wherein the method reduces organ damage, or the risk of organ damage, resulting from myocardial ischemia.

7. The method of claim 1, wherein the method reduces organ damage, or the risk of organ damage, resulting from cerebral ischemia.

8. The method of claim 1, wherein the method reduces organ damage, or the risk of organ damage, resulting from renal ischemia.

9. The method of claim 1, wherein the S-meclizine is administered for at least several days.

\* \* \* \* \*